(12) United States Patent
Dubey et al.

(10) Patent No.: US 11,865,109 B2
(45) Date of Patent: Jan. 9, 2024

(54) FORMULATIONS OF (S)-3-AMINO-6-METHOXY-N-(3,3,3-TRIFLUORO-2-HYDROXY-2-METHYLPROPYL)-5-(TRIFLUOROMETHYL)PICOLINAMIDE

(71) Applicant: NOVARTIS AG, Basel (CH)

(72) Inventors: Vivek Dubey, Telangana (IN); Rohit Lowalekar, Telangana (IN); Paulo G. Santos, Binningen (CH); Hubert Thoma, Pfaffenweiler (DE); Xianbin Tian, Lincoln Park, NJ (US)

(73) Assignee: NOVARTIS AG, Basel (CH)

( * ) Notice: Subject to any disclaimer, the term of this patent is extended or adjusted under 35 U.S.C. 154(b) by 560 days.

(21) Appl. No.: 16/929,472

(22) Filed: Jul. 15, 2020

(65) Prior Publication Data

US 2021/0015804 A1    Jan. 21, 2021

(30) Foreign Application Priority Data

Jul. 15, 2019 (IN) .............................. 201911028435
Jun. 3, 2020 (IN) .............................. 202011023329

(51) Int. Cl.
*A61K 31/44* (2006.01)
*A61K 9/20* (2006.01)
*A61K 9/28* (2006.01)

(52) U.S. Cl.
CPC ............ *A61K 31/44* (2013.01); *A61K 9/2013* (2013.01); *A61K 9/2059* (2013.01); *A61K 9/2095* (2013.01); *A61K 9/28* (2013.01)

(58) Field of Classification Search
CPC ....................................................... A61K 31/44
See application file for complete search history.

(56) References Cited

U.S. PATENT DOCUMENTS

| 9,365,552 B2 | 6/2016 | Baettig et al. |
| 2011/0230483 A1 | 9/2011 | Baettig et al. |
| 2018/0141954 A1 | 5/2018 | Strohbach et al. |
| 2018/0170938 A1 | 6/2018 | Strohbach et al. |

FOREIGN PATENT DOCUMENTS

| WO | 2011/113894 A1 | 9/2011 |
| WO | 2011/160798 A1 | 12/2011 |
| WO | 2018/029565 A1 | 2/2018 |
| WO | 2018/116139 A1 | 6/2018 |

OTHER PUBLICATIONS

Notification of Transmittal of the International Search Report and the Written Opinion of the International Searching Authority, or the Declaration, dated Oct. 19, 2020 in International Patent Application No. PCT/IB2020/056661, filed on Jul. 15, 2020.
Rademacher et al, Brochiectasis-Diagnosis and Treatment, Deutsches Aerteblatt International, 2011, pp. 809-815, 108(48).

*Primary Examiner* — Alicia L Otton
(74) *Attorney, Agent, or Firm* — Adil R. Zhugralin

(57) ABSTRACT

Provided herein are compounds and pharmaceutical compositions useful for treating bronchiectasis, chronic obstructive pulmonary disorder, cystic fibrosis, chronic bronchitis or asthma comprising administering to a subject in need thereof a therapeutically effective amount of a compound or pharmaceutical composition described herein.

10 Claims, 12 Drawing Sheets

| Screening | Treatment | | | | | | | | | | | Observational F/U | | | | | | | Safety Follow-up | | | | | |
|---|---|---|---|---|---|---|---|---|---|---|---|---|---|---|---|---|---|---|---|---|---|---|---|---|
| | AM | Cmpd 1 400 mg | | | | Cmpd 1 400 mg | | | | Cmpd 1 400 mg | | | | | | | | | | | | | | |
| | Day | 1 | 2 | 3 | 4 | 5 | 6 | 7 | 8 | 9 | 10 | 11 | 12 | 13 | 14 | 15 | 16 | 17 | 18 | 19 | 20 | 23 | 26 | 32 | 33 |
| | PM | Cmpd 1 400 mg | | | | Cmpd 1 400 mg | | | | Cmpd 1 400 mg | | | | | | | | | | | | | | | EOS |
| -28 to -1 | Confined to Site | | | | | X | | | | | | | | | | | | | | X | X | X | X | |

Fig. 10

EOS=End of study, F/U=Follow-up

FORMULATIONS OF (S)-3-AMINO-6-METHOXY-N-(3,3,3-TRIFLUORO-2-HYDROXY-2-METHYLPROPYL)-5-(TRIFLUOROMETHYL)PICOLINAMIDE

1. CROSS REFERENCE TO RELATED APPLICATIONS

This application claims the benefit of priority to Indian Provisional Application No. 202011023329, filed Jun. 3, 2020 and Indian Provisional Application No. 201911028435, filed Jul. 15, 2019, the disclosure of each of which is incorporated by reference herein in its entirety.

2. FIELD OF THE INVENTION

The present invention relates to pharmaceutical compositions comprising the compound (S)-3-amino-6-methoxy-N-(3,3,3-trifluoro-2-hydroxy-2-methylpropyl)-5-(trifluoromethyl)picolinamide or a pharmaceutically acceptable salt, polymorph, or co-crystal thereof, sodium starch glycolate and sodium stearyl fumarate. The present invention also relates to the processes for their preparation and to their use as medicaments for the treatment of Chronic Obstructive Pulmonary Disorder (COPD), Cystic Fibrosis (CF), bronchiectasis, chronic bronchitis, primary ciliary dyskinesia, respiratory tract infections or asthma.

3. BACKGROUND

Cystic fibrosis (CF) is a fatal genetic disease caused by mutations in the gene encoding the CF transmembrane conductance regulator (CFTR), a protein kinase A (PKA)-activated epithelial anion channel involved in salt and fluid transport in multiple organs, including the lungs. Most CF mutations either reduce the number of CFTR channels at the cell surface (e.g., synthesis or processing mutations) or impair channel function (e.g., gating or conductance mutations) or both. The present invention discloses pharmaceutical compositions comprising compounds which restore or enhance the function of mutant and/or wild type CFTR to treat COPD, CF, chronic bronchitis, primary ciliary dyskinesia, respiratory tract infections or asthma.

Bronchiectasis is a chronic disease characterized by abnormal and permanent dilation of the bronchi resulting in chronic cough, sputum production, and recurrent bacterial infections of the airways (Martinez-Garcia et al., Chest. 2005 August; 128(2):739-45; Wilson et al., Eur Respir J. 1997 August; 10(8):1754-60). Bronchiectasis is generally classified into either cystic fibrosis bronchiectasis or non-cystic fibrosis bronchiectasis (King et al., Intern Med J. 2006 36(11):729-737). Patients with bronchiectasis suffer from a high morbidity due to frequent exacerbations impairing quality of life and facilitating resistance to antibiotics, leading to reduced lung function. There is also a high socioeconomic impact through frequent use of primary and secondary healthcare with an economic burden estimated to be similar to COPD (Polverino et al., Eur Respir J. 2017 Sep. 9; 50(3)). The age-adjusted mortality of patients with bronchiectasis compared to the general population is approximately two-fold higher (Quint et al., Eur Respir J. 2016 January; 47(1):186-93). Patients with bronchiectasis have some similarities to those with CF such as radiological dilatation of airways, bronchial wall thickening, mucus plugging, and hyperinflation.

International Publication No. WO 2011/113894 describes certain compounds which restore or enhance the function of mutant and/or wild type CFTR for the treatment of CF, primary ciliary dyskinesia, bronchiectasis, chronic bronchitis, COPD, asthma, and other CFTR related diseases, the disclosure of which is incorporated by reference herein in its entirety. The compounds described therein include Compound 1 having the chemical name (S)-3-amino-6-methoxy-N-(3,3,3-trifluoro-2-hydroxy-2-methylpropyl)-5-(trifluoromethyl)picolinamide and having the following structure:

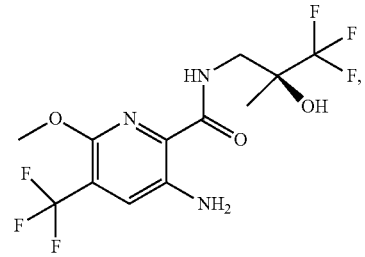 [SMILES: COc1nc(C(=O)NC[C@](C)(O)C(F)(F)F)c(N)cc1C(F)(F)F]

and its pharmaceutically acceptable salts, stereoisomers or mixture of stereoisomers, tautomers, prodrugs, polymorphs, or co-crystals thereof (see Example 5 of WO 2011/113894). A process for preparing Compound 1 and its intermediates is described in International Publication No. WO/2018/116139, the disclosure of which is incorporated by reference herein in its entirety.

Administration of pharmaceutical agents via the oral route is advantageous to other administration routes (e.g., parenteral) because it allows self-administration by patients instead of administration by a physician, nurse or paramedical personnel.

However, Compound 1 and its pharmaceutically acceptable salts, stereoisomers or mixture of stereoisomers, tautomers, prodrugs, polymorphs, or co-crystals thereof are difficult to formulate into a pharmaceutical composition due to its physiochemical properties, such as poor flowability, poor wettability, low bulk density, low melting point, poor compressibility, and poor solubility. For example, use of common lubricants (e.g., magnesium stearate) and disintegrants in formulating a pharmaceutical composition comprising Compound 1 resulted in sticking of Compound 1 to the tableting machinery and high friability, cracking, and swelling of the tablet. Accordingly, there is a need to develop suitable and robust pharmaceutical compositions overcoming the above problems related to the poor physiochemical properties of Compound 1 and its pharmaceutically acceptable salts, stereoisomers or mixture of stereoisomers, tautomers, prodrugs, polymorphs, or co-crystals thereof.

Surprisingly, it has been found that pharmaceutical compositions comprising Compound 1 or a pharmaceutically acceptable salt, stereoisomers or mixture of stereoisomers, tautomers, prodrugs, polymorphs, or co-crystals thereof can be prepared conveniently using high shear wet granulation when sodium starch glycolate is used as a disintegrant and sodium stearyl fumarate is used as a lubricant. These pharmaceutical compositions overcome the foregoing problems and exhibit no friability, sticking, cracking or swelling with sufficient compressibility and hardness for the reliable delivery of Compound 1 or its pharmaceutically acceptable salts, stereoisomers or mixture of stereoisomers, tautomers, prodrugs, polymorphs, or co-crystals thereof.

4. SUMMARY

In certain embodiments, provided herein is a pharmaceutical composition comprising, (S)-3-amino-6-methoxy-N-

(3,3,3-trifluoro-2-hydroxy-2-methylpropyl)-5-(trifluoromethyl)picolinamide having the following structure

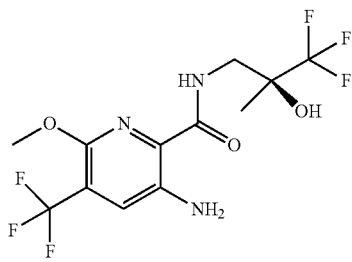 [SMILES: COc1nc(C(=O)NC[C@](C)(O)C(F)(F)F)c(N)cc1C(F)(F)F]

or a pharmaceutically acceptable salt, polymorph, or co-crystal thereof, sodium starch glycolate, and sodium stearyl fumarate.

In certain embodiments, provided herein is a pharmaceutical composition comprising, (S)-3-amino-6-methoxy-N-(3,3,3-trifluoro-2-hydroxy-2-methylpropyl)-5-(trifluoromethyl)picolinamide having the following structure

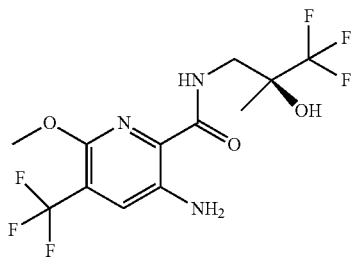 [SMILES: COc1nc(C(=O)NC[C@](C)(O)C(F)(F)F)c(N)cc1C(F)(F)F]

or a pharmaceutically acceptable salt, polymorph, or co-crystal thereof, crospovidone, and sodium stearyl fumarate.

In certain embodiments of the composition, (S)-3-amino-6-methoxy-N-(3,3,3-trifluoro-2-hydroxy-2-methylpropyl)-5-(trifluoromethyl)picolinamide is present in an amount ranging from about 40% to about 50% by weight relative to the total weight of the composition, calculated based on its free base.

In certain embodiments of the composition, (S)-3-amino-6-methoxy-N-(3,3,3-trifluoro-2-hydroxy-2-methylpropyl)-5-(trifluoromethyl)picolinamide is present in an amount ranging from about 44% to about 45% by weight relative to the total weight of the composition, calculated based on its free base.

In certain embodiments of the composition, sodium starch glycolate is present in an amount ranging from about 8% to about 13% weight relative to the total weight of the composition.

In certain embodiments of the composition, crospovidone is present in an amount ranging from about 6% to about 10% weight relative to the total weight of the composition.

In certain embodiments of the composition, sodium stearyl fumarate is present in an amount ranging from about 1% to about 3% by weight relative to the total weight of the composition.

In certain embodiments of the composition, the composition further comprises at least one pharmaceutically acceptable carrier wherein the carrier is a diluent, a glidant, or combinations thereof.

In certain embodiments of the composition, the composition further comprises a diluent.

In certain embodiments of the composition, the diluent is mannitol, microcrystalline cellulose, or a combination thereof.

In certain embodiments of the composition, the diluent is mannitol.

In certain embodiments of the composition, the diluent is microcrystalline cellulose.

In certain embodiments of the composition, the diluent is present in an intragranular phase in an amount ranging from about 22% to about 30% by weight relative to the total weight of the composition.

In certain embodiments of the composition, the diluent is present in an extragranular phase in an amount ranging from about 7% to about 12% by weight relative to the total weight of the composition.

In certain embodiments of the composition, the composition further comprises a glidant.

In certain embodiments of the composition, the glidant is collodial silicon dioxide.

In certain embodiments of the composition, the glidant is present in an amount ranging from about 1% to about 5% by weight relative to the total weight of the composition.

In certain embodiments of the composition, the composition comprises an amount equal to about 1, about 5, about 10, about 25, about 50, about 75, about 100, about 150, about 200, about 250, about 300, about 350, about 400, or about 450 mg of the compound (S)-3-amino-6-methoxy-N-(3,3,3-trifluoro-2-hydroxy-2-methylpropyl)-5-(trifluoromethyl)picolinamide or a pharmaceutically acceptable salt, polymorph, or co-crystal thereof.

In certain embodiments of the composition, the composition comprises an amount equal to about 75 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph, or co-crystal thereof.

In certain embodiments of the composition, the composition comprises an amount equal to about 150 mg of (S)-3-amino-6-methoxy-N-(3,3,3-trifluoro-2-methylpropyl)-5-(trifluoromethyl)picolinamide or a pharmaceutically acceptable salt, polymorph, or co-crystal thereof.

In certain embodiments of the composition, the composition comprises an amount equal to about 300 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph, or co-crystal thereof.

In certain embodiments of the composition, the composition comprises an amount equal to about 400 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph, or co-crystal thereof.

In certain embodiments of the composition, the composition comprises an amount equal to about 450 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph, or co-crystal thereof.

In certain embodiments of the composition, the composition comprises a plurality of granules each comprising an intragranular phase and an extragranular phase, and wherein said intragranular phase and extragranular phase of the granules each comprise sodium starch glycolate.

In certain embodiments of the composition, the composition comprises a plurality of granules each comprising an intragranular phase and an extragranular phase, and wherein said intragranular phase and extragranular phase of the granules each comprise crospovidone.

In certain embodiments of the composition, the composition shows an in vitro dissolution of (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof of 80%, 85%, 90%, 95% or more in 60 minutes or less as optionally measured by a USP Apparatus II (paddle).

In certain embodiments of the composition, (S)-3-amino-6-methoxy-N-(3,3,3-trifluoro-2-hydroxy-2-methylpropyl)-5-(trifluoromethyl)picolinamide is present as a besylate salt.

In certain embodiments of the composition, the composition is a tablet.

In certain embodiments of the composition, the composition is a film-coated tablet.

In certain embodiments of the composition, the composition is manufactured by a process comprising a step of high shear wet granulation.

In certain embodiments of the composition, the composition is an immediate release dosage form.

In certain embodiments of the composition, the pharmaceutical composition comprises a crystalline form of (S)-3-amino-6-methoxy-N-(3,3,3-trifluoro-2-hydroxy-2-methylpropyl)-5-(trifluoromethyl)picolinamide characterized by an X-ray powder diffraction pattern comprising one or more peaks selected from 14.4, 15.8, 17.5 19.4 20.1 20.7 21.5, 25.2, 25.8, 33.7±0.2° 2θ.

In certain embodiments, provided herein is a method for the treatment of bronchiectasis, chronic obstructive pulmonary disorder, cystic fibrosis, chronic bronchitis or asthma, comprising administering the pharmaceutical composition disclosed herein to a subject in need thereof.

In certain embodiments, provided herein is a method for promoting mucus clearance in a subject with bronchiectasis, chronic obstructive pulmonary disorder, cystic fibrosis, chronic bronchitis or asthma comprising administering the pharmaceutical composition disclosed herein to a subject in need thereof.

In certain embodiments of the methods provided herein, the composition is administered to the subject without a high fat meal.

In certain embodiments of the methods provided herein, the composition comprises an amount equal to about 300 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof and such composition is administered to the subject without a high fat meal.

In certain embodiments of the methods provided herein, the composition comprises an amount equal to about 400 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof and such composition is administered to the subject without a high fat meal.

In certain embodiments of the methods provided herein, the composition comprises an amount equal to about 450 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof and such composition is administered to the subject without a high fat meal.

In certain embodiments of the methods provided herein, the high fat meal has not been consumed together with administration of the composition to the subject.

In certain embodiments of the methods provided herein, the high fat meal has not been consumed about 30 minutes prior to administration of the composition to the subject.

In certain embodiments of the methods provided herein, administration results in a lower maximal plasma concentration (Cmax) and extent of exposure (AUClast or AUCinf) of (S)-3-amino-6-methoxy-N-(3,3,3-trifluoro-2-hydroxy-2-methylpropyl)-5-(trifluoromethyl)picolinamide as compared to administration with a high fat meal.

In certain embodiments of the methods provided herein, the composition is administered in two oral doses per day.

In certain embodiments, provided herein is a method for the treatment of bronchiectasis, chronic obstructive pulmonary disorder, cystic fibrosis, chronic bronchitis or asthma, comprising administering (S)-3-amino-6-methoxy-N-(3,3,3-trifluoro-2-hydroxy-2-methylpropyl)-5-(trifluoromethyl)picolinamide to a subject in need thereof, wherein (S)-3-amino-6-methoxy-N-(3,3,3-trifluoro-2-hydroxy-2-methylpropyl)-5-(trifluoromethyl)picolinamide is administered to the subject without a high fat meal.

In certain embodiments, provided herein is a method for promoting mucus clearance in a subject with bronchiectasis, chronic obstructive pulmonary disorder, cystic fibrosis, chronic bronchitis or asthma comprising administering (S)-3-amino-6-methoxy-N-(3,3,3-trifluoro-2-hydroxy-2-methylpropyl)-5-(trifluoromethyl)picolinamide to a subject in need thereof, wherein (S)-3-amino-6-methoxy-N-(3,3,3-trifluoro-2-hydroxy-2-methylpropyl)-5-(trifluoromethyl)picolinamide is administered to the subject without a high fat meal.

In certain embodiments of the methods provided herein, the high fat meal has not been consumed together with administration of the composition to the subject.

In certain embodiments of the methods provided herein, the high fat meal has not been consumed about 30 minutes prior to administration of the composition to the subject.

In certain embodiments of the methods provided herein, administration results in a lower maximal plasma concentration (Cmax) and extent of exposure (AUClast or AUCinf) of (S)-3-amino-6-methoxy-N-(3,3,3-trifluoro-2-hydroxy-2-methylpropyl)-5-(trifluoromethyl)picolinamide as compared to administration with a high fat meal.

In certain embodiments of the methods provided herein, (S)-3-amino-6-methoxy-N-(3,3,3-trifluoro-2-hydroxy-2-methylpropyl)-5-(trifluoromethyl)picolinamide is administered in a pharmaceutical composition.

In certain embodiments of the methods provided herein, the composition comprises an amount equal to about 300 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof and such composition is administered to the subject without a high fat meal.

In certain embodiments of the methods provided herein, the composition comprises an amount equal to about 400 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof.

In certain embodiments of the methods provided herein, the composition comprises an amount equal to about 450 mg of (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof.

In certain embodiments of the methods provided herein, the composition is administered in two oral doses per day.

In certain embodiments, provided herein is a method of lowering the oral bioavailability of (S)-3-amino-6-methoxy-N-(3,3,3-trifluoro-2-hydroxy-2-methylpropyl)-5-(trifluoromethyl)picolinamide in a subject receiving (S)-3-amino-6-methoxy-N-(3,3,3-trifluoro-2-hydroxy-2-methylpropyl)-5-(trifluoromethyl)picolinamide comprising administering to the subject a therapeutically effective amount of (S)-3-amino-6-methoxy-N-(3,3,3-trifluoro-2-hydroxy-2-methylpropyl)-5-(trifluoromethyl)picolinamide without a high fat meal.

In certain embodiments of the methods provided herein, administration results in a lower maximal plasma concentration (Cmax) and extent of exposure (AUClast or AUCinf) of (S)-3-amino-6-methoxy-N-(3,3,3-trifluoro-2-hydroxy-2-methylpropyl)-5-(trifluoromethyl)picolinamide as compared to administration with a high fat meal.

In certain embodiments of the methods provided herein, the composition is administered in combination with at least one additional therapy. In some embodiments, the additional therapy comprises: a) a long-acting beta-agonist (LABA); b) a long-acting muscarinic antagonists (LAMA); c) an inhaled corticosteroid (ICS); d) macrolides; e) an antibiotic; f) a short-acting muscarinic antagonist (SAMA); or g) any combination thereof.

In certain embodiments, provided herein is a use of the pharmaceutical composition provided herein for the treatment of bronchiectasis, chronic obstructive pulmonary disorder, cystic fibrosis, chronic bronchitis or asthma.

In certain embodiments, provided herein is a use of the pharmaceutical composition provided herein for the manufacture of a medicament for the treatment of bronchiectasis, chronic obstructive pulmonary disorder, cystic fibrosis, chronic bronchitis or asthma.

In certain embodiments, provided herein is a pharmaceutical composition provided herein for use in the treatment of bronchiectasis, chronic obstructive pulmonary disorder, cystic fibrosis, chronic bronchitis or asthma.

In certain embodiments of the pharmaceutical composition provided herein, the composition is administered to a subject without a high fat meal.

In certain embodiments of the pharmaceutical composition provided herein, the high fat meal has not been consumed together with administration of the composition to the subject.

In certain embodiments of the pharmaceutical composition provided herein, the high fat meal has not been consumed about 30 minutes prior to administration of the composition to the subject.

In certain embodiments of the pharmaceutical composition provided herein, administration results in a lower maximal plasma concentration (Cmax) and extent of exposure (AUClast or AUCinf) of (S)-3-amino-6-methoxy-N-(3,3,3-trifluoro-2-hydroxy-2-methylpropyl)-5-(trifluoromethyl)picolinamide as compared to administration with a high fat meal.

In certain embodiments of the pharmaceutical composition provided herein, the composition is administered in combination with at least one additional therapy. In some embodiments, the additional therapy comprises: a) a long-acting beta-agonist (LABA); b) a long-acting muscarinic antagonists (LAMA); c) an inhaled corticosteroid (ICS); d) macrolides; e) an antibiotic; f) a short-acting muscarinic antagonist (SAMA); or g) any combination thereof.

In certain embodiments, provided herein is a compound (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof for use in the treatment of bronchiectasis, chronic obstructive pulmonary disorder, cystic fibrosis, chronic bronchitis or asthma, wherein the compound is administered without a high fat meal.

In certain embodiments of the compound, the high fat meal has not been consumed together with administration of the composition to the subject.

In certain embodiments of the compound, the high fat meal has not been consumed about 30 minutes prior to administration of the composition to the subject.

In certain embodiments of the compound, administration results in a lower maximal plasma concentration (Cmax) and extent of exposure (AUClast or AUCinf) of (S)-3-amino-6-methoxy-N-(3,3,3-trifluoro-2-hydroxy-2-methylpropyl)-5-(trifluoromethyl)picolinamide as compared to administration with a high fat meal.

In certain embodiments, provided herein is a process for the manufacture of the pharmaceutical composition provided herein comprising the steps of: (a) blending (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof together with sodium starch glycolate and optionally at least one pharmaceutically acceptable carrier to form a material, (b) wet milling the material to form a plurality of granules, (c) blending the granules with sodium stearyl fumarate and sodium starch glycolate and optionally at least one pharmaceutically acceptable carrier to form a final blend, and (d) compressing the final blend into a tablet.

In certain embodiments, provided herein is a process for the manufacture of the pharmaceutical composition provided herein comprising the steps of: (a) blending (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof together with sodium starch glycolate and optionally at least one pharmaceutically acceptable carrier to form a material, (b) wet milling the material to form a plurality of granules, (c) blending the granules with sodium stearyl fumarate and crospovidone, and optionally at least one pharmaceutically acceptable carrier to form a final blend, and (d) compressing the final blend into a tablet.

In certain embodiments, provided herein is a pharmaceutical composition produced by the process provided herein.

In certain embodiments, provided herein is a pharmaceutical composition for use the treatment of bronchiectasis, chronic obstructive pulmonary disorder, cystic fibrosis, chronic bronchitis or asthma, wherein the pharmaceutical composition is produced by the process provided herein.

In certain embodiments, provided herein is a crystalline form of (S)-3-amino-6-methoxy-N-(3,3,3-trifluoro-2-hydroxy-2-methylpropyl)-5-(trifluoromethyl)picolinamide characterized by an X-ray powder diffraction pattern comprising one or more peaks selected from 14.4, 15.8, 17.5 19.4 20.1 20.7 21.5, 25.2, 25.8, 33.7±0.220.

BRIEF DESCRIPTION OF THE DRAWINGS

FIG. 10 provides an illustrative representation of the treatment sequence from the absorption, distribution, metabolism, and excretion study of Compound 1.

5. DETAILED DESCRIPTION

Figure 1:
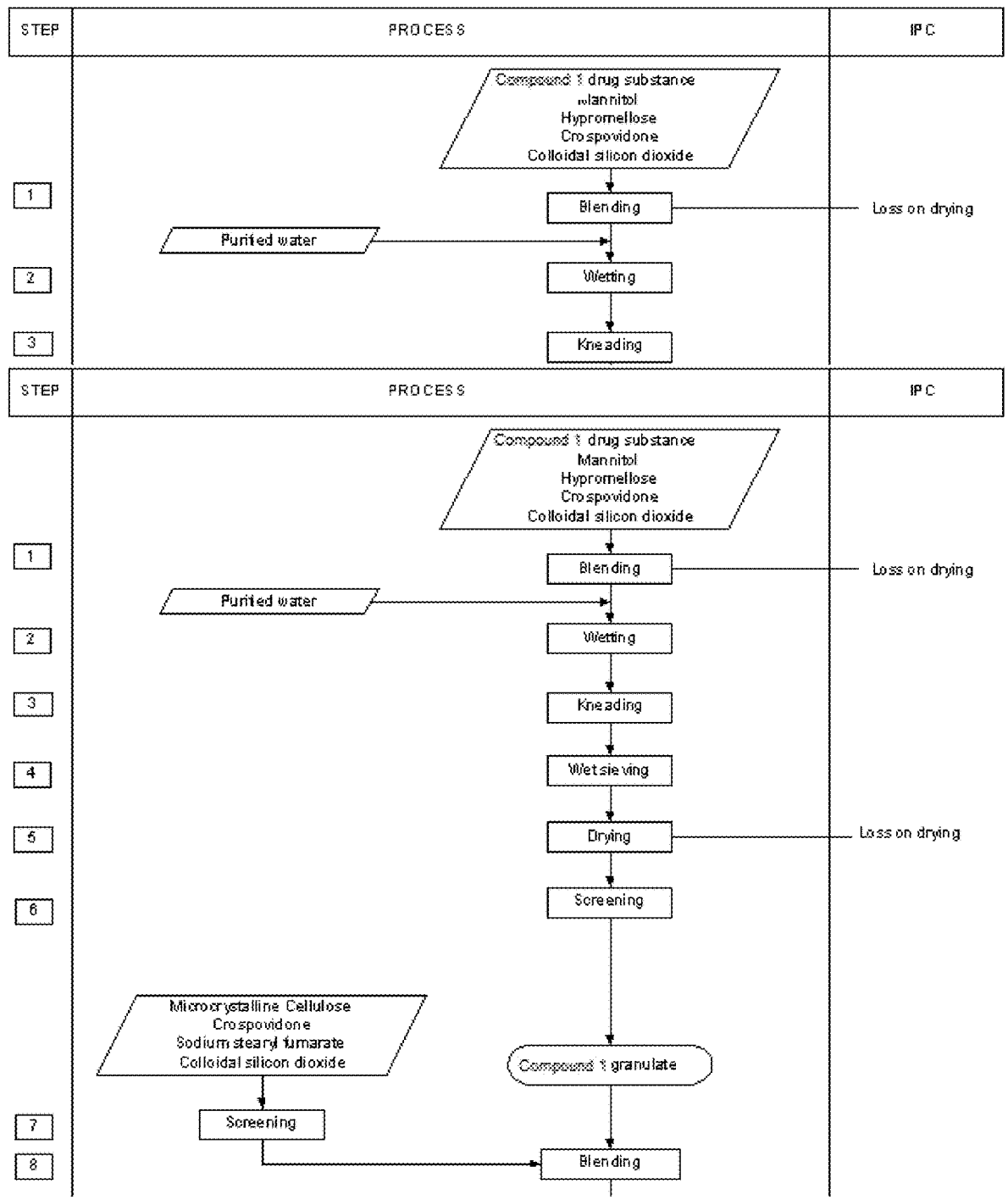
FIG. 1 provides an illustration of the manufacture for Formulation A.

Provided herein are pharmaceutical compositions of Compound 1 or its pharmaceutically acceptable salts, stereoisomers or mixture of stereoisomers, tautomers, prodrugs, polymorphs, or co-crystals thereof. In some embodiments, the pharmaceutical compositions are suitable for oral administration to a subject.

5.1. Definitions

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The terms "about" and "approximately" are used to provide flexibility to a numerical range endpoint by providing that a given value may be "a little above" or "a little below" the endpoint accounting for variations one might see in measurements taken among different instruments, samples, and sample preparations. The terms "about" and "approximately" usually means within 10%, more preferably within 5%, and most preferably still within 1% of a given value or range. With respect to features such as endotherms, exotherms, baseline shifts, etc., that their values can vary ±2° C. For differential scanning calorimetry (DSC), variation in the temperatures observed will depend upon the rate of temperature change as well as sample preparation technique and the particular instrument employed. Thus, the endotherm/melting point values reported herein relating to thermo gravimetric analysis (TGA) profiles can vary 4° C. (and still be considered to be characteristic of the particular crystalline form of Compound 1 referenced).

The terms "administration" and "administering" and "administer" refer to the manner in which a compound described herein (e.g., Compound 1) is presented to a subject.

The term "Compound 1" refers to (S)-3-amino-6-methoxy-N-(3,3,3-trifluoro-2-hydroxy-2-methylpropyl)-5-(trifluoromethyl)picolinamide having the following structure:

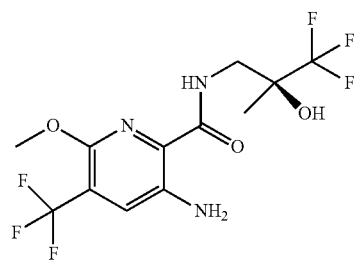 [SMILES: COc1nc(C(=O)NC[C@](C)(O)C(F)(F)F)c(N)cc1C(F)(F)F]

and its pharmaceutically acceptable salts, stereoisomers or mixture of stereoisomers, tautomers, prodrugs, polymorphs, or co-crystals thereof.

The terms "comprise" or "comprises" or "comprising" and "including" are used herein in their open-ended and non-limiting sense unless otherwise noted and should be understood to imply the inclusion of a stated integer or step or group of integers or steps but not the exclusion of any other integer or step or group of integers or steps.

The term "extragranular phase" refers to that portion of the pharmaceutical composition which is added to an intragranular phase to make up together with the intragranular phase the final blend.

The term "intragranular phase" refers to that portion of the pharmaceutical composition which is granulated (e.g., by wet granulation).

The term "final blend" refers to the combined intragranular phase and extragranular phase which is ready for being compressed to tablets or filled into capsules.

The terms "without food" or "fasted state" or "fasted" are defined to mean the condition of not having consumed food within a certain time prior to the administration of Compound 1 or a pharmaceutical composition comprising Compound 1 disclosed herein to a certain time after the administration of Compound 1 or a composition comprising Compound 1. In some embodiments, food has not been consumed for about 10 hours, about 8 hours, about 6 hours, about 4 hours, about 2 hours, about 1 hour, or about 30 minutes prior to administration of Compound 1 or a pharmaceutical composition comprising Compound 1 disclosed herein. In preferred embodiments, food has not been consumed for about 10 hours prior to administration of Compound 1 or a pharmaceutical composition comprising Compound 1 disclosed herein.

The terms "fed state" or "fed" are defined to mean the condition of having consumed food within a certain time prior to the administration of Compound 1 or a pharmaceutical composition comprising Compound 1 disclosed herein to a certain time after the administration of Compound 1 or a composition comprising Compound 1. In some embodiments, food has been consumed within about 10 hours, about 8 hours, about 6 hours, about 4 hours, about 2 hours, about 1 hour, or about 30 minutes prior to administration of Compound 1 or a pharmaceutical composition comprising Compound 1 disclosed herein. In preferred embodiments, food has been consumed within about 5 minutes prior to administration of Compound 1 or a pharmaceutical composition comprising Compound 1 disclosed herein.

The term "high fat meal" refers to the definition by the U.S. Food and Drug Administration in the draft guidance on Assessing the Effects of Food on Drugs in INDs and NDAs (FDA 2019) (see also Assessing the Effects of Food on Drugs in Investigational New Drug Applications and New Drug Applications-Clinical Pharmacology Considerations; Draft Guidance for Industry; Availability, 84 Fed. Reg. 6151 (Feb. 26, 2019)) and the corresponding EMA guideline (EMA 2012), wherein the high fat meal contains at least 1000 kcal (4184 kJ) and at least 50% of that energy content is derived from fat. An example of a high-fat meal would be:
  Total nutritional energy value: 1000 kcal
  of which from proteins: 150 kcal
  of which from carbohydrates: 250 kcal
  of which from fats: 600 kcal.

The terms "without a high fat meal" is defined to mean the condition of not having consumed a high fat meal together with administration of Compound 1 or a pharmaceutical composition comprising Compound 1 disclosed herein or the condition of not having consumed a high fat meal within a certain time prior to the administration of Compound 1 or a pharmaceutical composition comprising Compound 1 disclosed herein to a certain time after the administration of Compound 1 or a pharmaceutical composition comprising Compound 1 disclosed herein. In some embodiments, the high fat meal has not been consumed for about 10 hours, about 8 hours, about 6 hours, about 4 hours, about 2 hours, about 1 hour, about 30 minutes, about 15 minutes, about 5 minutes, or about 1 minute prior to administration of Compound 1 or a pharmaceutical composition comprising Compound 1 disclosed herein. In some embodiments, the high fat meal has not been consumed for about 10 hours, about 8 hours, about 6 hours, about 4 hours, about 2 hours, about 1 hour, about 30 minutes, about 15 minutes, about 5 minutes, or about 1 minute after the administration of Compound 1 or a pharmaceutical composition comprising Compound 1 disclosed herein. In other embodiments, the high fat meal has not been consumed together with administration of Compound 1 or a pharmaceutical composition comprising Compound 1 disclosed herein. In certain embodiments, the high fat meal has not been consumed for about 30 minutes prior to administration of Compound 1 or a pharmaceutical composition comprising Compound 1 disclosed herein.

The terms "with a high fat meal" is defined to mean the condition of having consumed a high fat meal together with administration of Compound 1 or a pharmaceutical composition comprising Compound 1 disclosed herein or the condition of having consumed a high fat meal within a certain time prior to the administration of Compound 1 or a pharmaceutical composition comprising Compound 1 disclosed herein to a certain time after the administration of Compound 1 or a pharmaceutical composition comprising Compound 1 disclosed herein. In some embodiments, the high fat meal has been consumed within about 10 hours, about 8 hours, about 6 hours, about 4 hours, about 2 hours, about 1 hour, about 30 minutes, about 15 minutes, about 5 minutes, or about 1 minute prior to administration of Compound 1 or a pharmaceutical composition comprising Compound 1 disclosed herein. In some embodiments, the high fat meal has been consumed within about 10 hours, about 8 hours, about 6 hours, about 4 hours, about 2 hours, about 1 hour, about 30 minutes, about 15 minutes, about 5 minutes, or about 1 minute after the administration of Compound 1 or a pharmaceutical composition comprising Compound 1 disclosed herein. In other embodiments, the high fat meal has been consumed together with administration of Compound 1 or a pharmaceutical composition comprising Compound 1 disclosed herein. In certain embodiments, the high fat meal has been consumed within about 30 minutes prior to administration of Compound 1 or a pharmaceutical composition comprising Compound 1 disclosed herein.

The term "oral dosage form" or "oral dosage" refers to a pharmaceutical composition that is prepared for administration to a subject through the oral route of administration. Examples of known oral dosage forms, include without limitation, tablets, capsules, caplets, powders, pellets, granules, solutions, suspensions, solutions and solution pre-concentrates, emulsions and emulsion pre-concentrates, etc. In some aspects, powders, pellets, granules and tablets may be coated with a film comprising a suitable polymer or a conventional coating material to achieve, for example, greater stability in the gastrointestinal tract, or to achieve the desired rate of release. Moreover, capsules containing a powder, pellets or granules may be further coated. Tablets may be scored to facilitate division of dosing. Alternatively, the dosage forms of the present invention may be unit dosage forms wherein the dosage form is intended to deliver one therapeutic dose per administration.

The term "oral administration" represents any method of administration in which a compound described herein (e.g., Compound 1) can be administered through the oral route by swallowing, chewing, or sucking an oral dosage form. Such solid or liquid oral dosage forms are traditionally intended to substantially release and or deliver the active agent in the gastrointestinal tract beyond the mouth and/or buccal cavity. Examples of solid dosage forms include conventional tablets, capsules, caplets, capsules, granules, etc.

The term "pharmaceutical composition" or "formulation" means a physical mixture containing a compound described herein (e.g., Compound 1) to be administered to a subject, e.g., a human, in order to prevent, treat or control a particular disease or condition affecting the subject. The term "pharmaceutical composition" or "formulation" as used herein, for example, also encompasses an intimate physical mixture formed at high temperature and pressure. In certain exemplary embodiments, a pharmaceutical composition comprises an intragranular phase and an extragranular phase.

The term "pharmaceutically acceptable" refers to those compounds, materials, compositions and/or dosage forms, which are, within the scope of sound medical or regulatory judgment, suitable for contact with the tissues of a subject, especially humans, without excessive toxicity, irritation, allergic response and other problem complications commensurate with a reasonable benefit/risk ratio.

The terms "pharmaceutically acceptable excipient" and "excipient" refer to any inert and pharmaceutically acceptable material that has substantially no biological activity and makes up a substantial part of the formulation.

The term "pharmaceutically acceptable salts" refers to pharmaceutically acceptable acid or base addition salts that retain the biological effectiveness and properties of the compound to which the term refers (e.g., Compound 1) and, which typically are not biologically or otherwise undesirable. Pharmaceutically acceptable salts of Compound 1 can be prepared in situ during the final isolation and purification of Compound 1, or by separately reacting the base or acid functions with a suitable organic or inorganic acid or base, respectively. Suitable salts of Compound 1 include but are not limited to the following: acetate, aspartate, benzoate, besylate, hydrobromide, bicarbonate/carbonate, bisulfate/sulfate, camphorsulformate, hydrochloride, chlortheophyllonate, citrate, ethandisulfonate, fumarate, gluceptate, gluconate, glucuronate, hippurate, hydrochloride, isethionate, lactate, lactobionate, laurylsulfate, malate, maleate, malonate, mandelate, mesylate, methylsulfate, naphthoate, napsylate, nicotinate, nitrate, octadecanoate, oleate, oxalate, palmitate, pamoate, phosphate/hydrogen phosphate/dihydrogen phosphate, polygalacturonate, propionate, sulfate, stearate, succinate, sulfosalicylate, tartrate, tosylate, and trifluoroacetate salts. Examples of inorganic acids that may be employed to form pharmaceutically acceptable acid addition salts include but are not limited to hydrochloric acid, hydrobromic acid, sulfuric acid, nitric acid, and phosphoric acid. Example of organic acids that may be employed to form pharmaceutically acceptable acid addition salts include but are not limited to acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, and sulfosalicylic acid. Examples of inorganic bases that may be employed to form pharmaceutically acceptable base addition salts include but are not limited ammonium salts and metals from columns I to XII of the periodic table. In certain embodiments, the salts are derived from sodium, potassium, ammonium, calcium, magnesium, iron, silver, zinc, and copper. Examples of organic bases that may be employed to form pharmaceutically acceptable base addition salts include but are not limited to primary, secondary, and tertiary amines, substituted amines including naturally occurring substituted amines, cyclic amines, and basic ion exchange resins. In certain embodiments, the salts are derived from isopropylamine, benzathine, cholinate, diethanolamine, diethylamine, lysine, meglumine, piperazine and tromethamine. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH. Weinheim, Germany, 2002).

The term "amorphous" refers to a solid form of a molecule, atom, and/or ions that is not crystalline. An amorphous solid does not display a definitive X-ray diffraction pattern.

The term "substantially the same" with reference to X-ray diffraction peak positions means that typical peak position and intensity variability are taken into account. For example, one skilled in the art will appreciate that the peak positions (°2θ) will show some inter-apparatus variability, typically as much as ±0.2° 2θ. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

The term "substantially pure," when used in reference to a form, means a compound having a purity greater than 90 weight %, including greater than 90, 91, 92, 93, 94, 95, 96, 97, 98, and 99 weight %, and also including equal to about 100 weight % of Compound 1, based on the weight of the compound. The remaining material comprises other form(s) of the compound, and/or reaction impurities and/or processing impurities arising from its preparation. For example, a crystalline form of Compound 1 may be deemed substantially pure in that it has a purity greater than 90 weight %, as measured by means that are at this time known and generally accepted in the art, where the remaining less than 10 weight % of material comprises other form(s) of Compound 1 and/or reaction impurities and/or processing impurities.

The term "polymorph" refers to crystalline forms having the same chemical composition but different spatial arrangements of the molecules, atoms, and/or ions forming the crystal.

The term "therapeutically effective amount" refers to an amount or concentration which, as compared to a corresponding subject who has not received such amount or concentration, is effective in reducing, eliminating, treating, healing, preventing or controlling the symptoms of a disease, disorder or condition affecting a subject. Thus, administration of a "therapeutically effective amount" of a pharmaceutical composition described herein refers to administration of an amount or concentration of such composition which is effective in reducing, eliminating, treating, healing, preventing or controlling the symptoms of a disease, disorder or condition affecting a subject. The term "controlling" is intended to refer to all processes wherein there may be slowing, interrupting, arresting or stopping of the progression of the disease, disorder, or condition affecting the subject. However, "controlling" does not necessarily indicate a total elimination of all disease, disorder, or condition symptoms.

The term "treat", "treating", or "treatment" includes prophylactic (preventive) and therapeutic treatment as well as the delay of progression of a disease or disorder described herein (e.g., COPD, CF, bronchiectasis (CF and non-CF), chronic bronchitis, primary ciliary dyskinesia, respiratory tract infections or asthma). The term "delay of progression" as used herein means administration of the pharmaceutical composition to patients being in a pre-stage or in an early phase of the disease or disorder described herein (e.g., COPD, CF, chronic bronchitis, primary ciliary dyskinesia, respiratory tract infections or asthma) to be treated, in which patients, for example a pre-form of the corresponding disease, are diagnosed or which patients are in a condition, e.g., during a medical treatment, under which it is likely that a corresponding disease will develop.

The term "stereomerically pure" means a composition that comprises one stereoisomer of a compound described here in (e.g., Compound 1) and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80 percent by weight of one stereoisomer of the compound and less than about 20 percent by weight of other stereoisomers of the compound, more preferably greater than about 90 percent by weight of one stereoisomer of the compound and less than about 10 percent by weight of the other stereoisomers of the compound, even more preferably greater than about 95 percent by weight of one stereoisomer of the compound and less than about 5 percent by weight of the other stereoisomers of the compound, and most preferably greater than about 97 percent by weight of one stereoisomer of the compound and less than about 3 percent by weight of the other stereoisomers of the compound.

The term "enantiomerically pure" means a stereomerically pure composition of a compound described herein (e.g., Compound 1) having one chiral center.

The term "subject" refers to a living organism suffering from one or more of the diseases or disorders described here (e.g., COPD, CF, bronchiectasis (CF and non-CF), chronic bronchitis, primary ciliary dyskinesia, respiratory tract infections or asthma) that can be treated by administration of a pharmaceutical composition described herein. Examples of subjects include mammals (e.g., humans and animals such as dogs, cows, horses, monkeys, pigs, sheep, goats, cats, mice, rabbits, rats, and transgenic non-human animals). In certain embodiments, the subject is a human, e.g., a human suffering from, at risk of suffering from, or potentially capable of suffering from a disease described herein (e.g., COPD, CF, bronchiectasis (CF and non-CF), chronic bronchitis, primary ciliary dyskinesia, respiratory tract infections or asthma).

Figure 11:
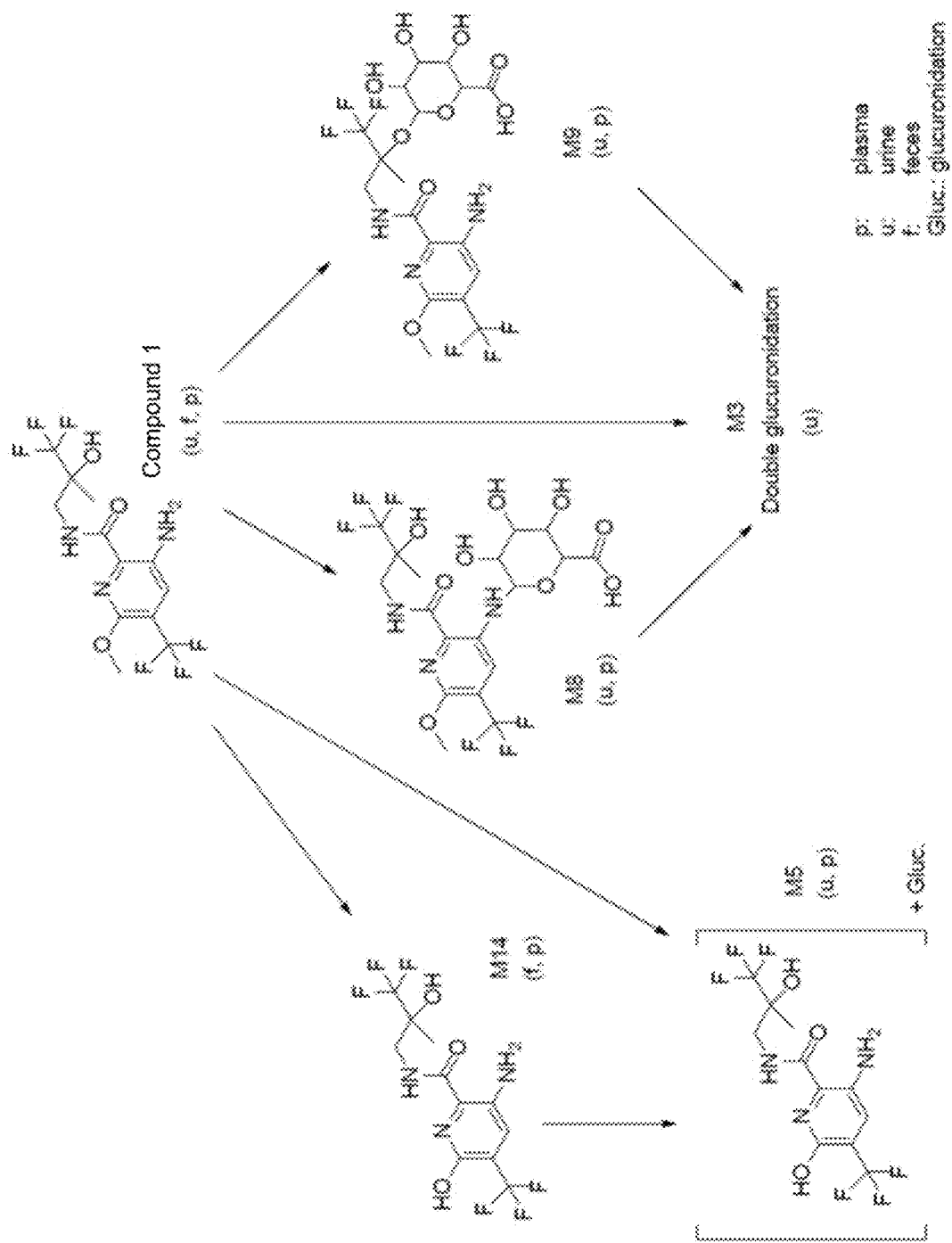
FIG. 11 illustrates a scheme of the major biotransformation pathways of Compound 1.
Figure 12:
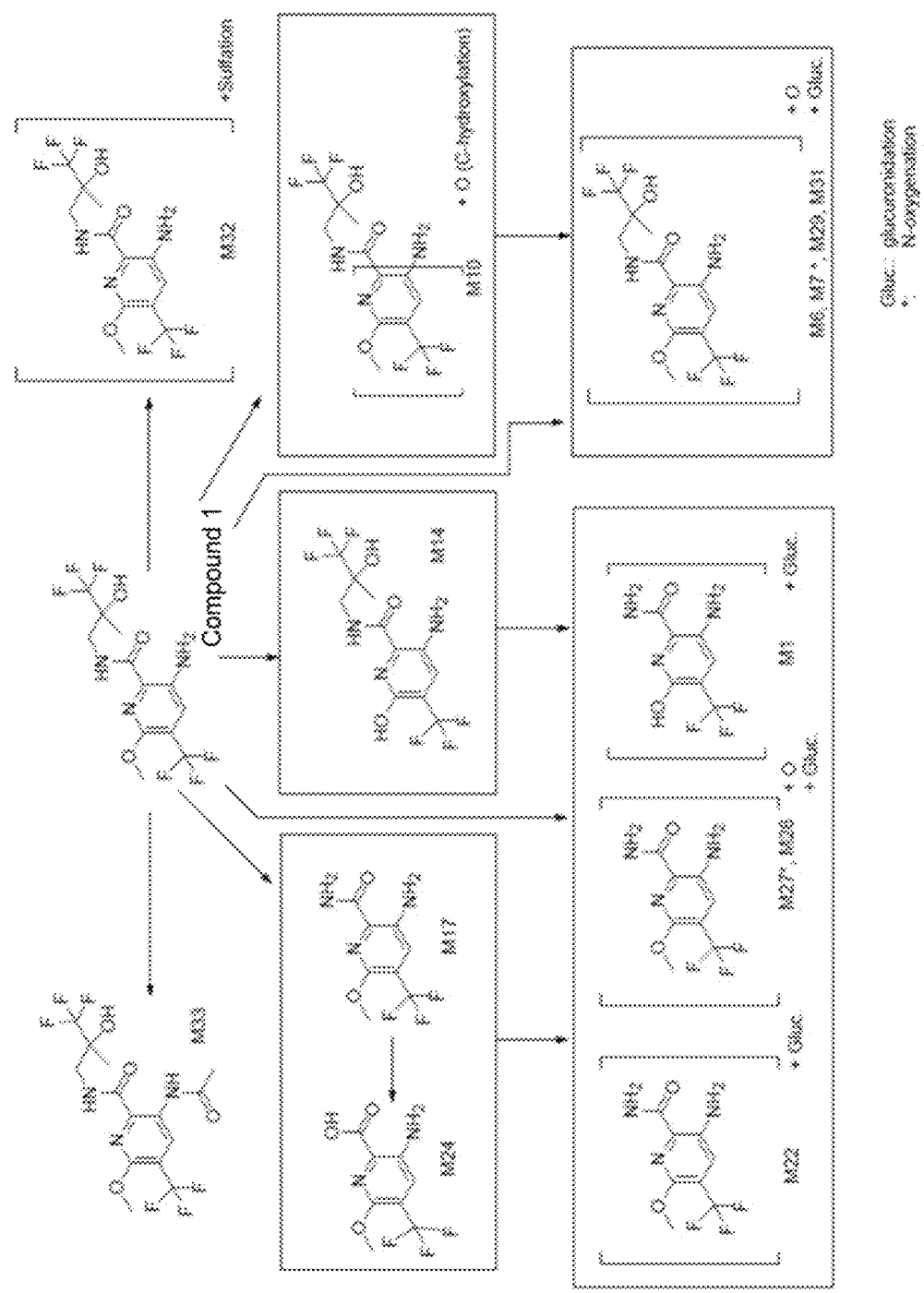
FIG. 12 illustrates a scheme of the minor biotransformation pathways of Compound 1.

The term "metabolite" refers to a compound or an intermediate formed through metabolism of a parent compound (e.g., Compound 1) in a subject. Examples of metabolites include M1, M3, M5, M6, M7, M8, M9, M10, M14, M17, M22, M24, M27, M28, M29, M31, M32, and M33, as depicted in FIG. 11 and FIG. 12.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

If there is a discrepancy between a depicted structure and a chemical name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure of portion of the structure.

5.2. Pharmaceutical Compositions of Compound 1

In one embodiment, provided herein are pharmaceutical compositions comprising Compound 1 present in the form of the free base. In certain embodiments, provided herein are pharmaceutical compositions comprising Compound 1 present in the form of a pharmaceutically acceptable salt, stereoisomer or mixture of stereoisomers, tautomer, prodrug, hydrate, solvate, co-crystal, clathrate, or polymorph thereof. In certain embodiments, provided herein are pharmaceutical compositions comprising Compound 1 present as a besylate salt, a mesylate salt, a tosylate salt, a hydrochloride salt, or a sulfate salt. In certain preferred embodiments, provided herein are pharmaceutical compositions comprising Compound 1 present as the besylate salt.

In one embodiment, provided herein is a pharmaceutical composition suitable for oral administration to a subject comprising an amount equal to or greater than 1, 5, 10, 25, 50, 75, 100, 150, 200, 250, 300, 350, 400, or 450 mg of Compound 1 or a pharmaceutically acceptable salt, polymorph, or co-crystal thereof, and a pharmaceutically acceptable carrier. In certain preferred embodiments, the amount of the active ingredient is an amount equal to or greater than 75 mg. In certain preferred embodiments, the amount of the active ingredient is an amount equal to or greater than 150 mg. In certain preferred embodiments, the amount of the active ingredient is an amount equal to or greater than 300 mg. In certain preferred embodiments, the amount of the active ingredient is an amount equal to or greater than 400 mg. In certain preferred embodiments, the amount of the active ingredient is an amount equal to or greater than 450 mg. In certain preferred embodiments, the amount of the active ingredient is 75 mg. In certain preferred embodiments, the amount of the active ingredient is 150 mg. In certain preferred embodiments, the amount of the active ingredient is 300 mg. In certain preferred embodiments, the amount of the active ingredient is 400 mg. In certain preferred embodiments, the amount of the active ingredient is 450 mg. In certain preferred embodiments, the subject is a human.

In certain embodiments, the pharmaceutical compositions provided herein may be administered in one to four dosages per day or may be administered on alternating days or with multiple days passing between administrations. In a preferred embodiment, the dosage is administered in two oral dosages per day (b.i.d.). In another preferred embodiment, the dosage is administered in one oral dosages per day.

Unless otherwise specified, the weight or dosage referred to herein for a particular compound (e.g., Compound 1) or crystalline form thereof of the disclosure is the weight or dosage of the compound itself, not that of a salt or solvate thereof, which can be different to achieve the intended therapeutic effect. For example, the weight of a corresponding salt of a compound suitable for the methods, compositions, or combinations disclosed herein may be calculated based on the ratio of the molecular weights of the salt and compound itself.

In one embodiment, the pharmaceutical compositions provided herein may be in the form of a powder, capsule, or tablet containing an amount of Compound 1 or a pharmaceutically acceptable salt, stereoisomer or mixture of stereoisomers, tautomer, prodrug, hydrate, solvate, co-crystal, clathrate, or polymorph thereof. In a preferred embodiment, the pharmaceutical composition provided herein is in the form of a tablet. In another preferred embodiment, the pharmaceutical composition provided herein is in the form of a film-coated or enteric-coated tablet. In certain embodiments, the film comprises hypromellose (HPMC) or polyvinyl alcohol (PVA) and optionally, at least one pigment (e.g., Opadry II by Colorcon).

The pharmaceutical compositions provided herein can be formulated for particular routes of administration such as oral administration, parenteral administration, and rectal administration, etc. In a preferred embodiment, the pharmaceutical compositions provided herein are prepared for oral administration, such as a tablet or capsule, for example, and optionally packaged in a multi-dose format suitable for storing and/or dispensing unit doses of a pharmaceutical product. Examples of suitable packaging include, but are not limited to, hermetically sealed foils, unit dose containers (e.g., vials), blister packs, and strip packs. In addition, the pharmaceutical compositions provided herein can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, carriers or buffering agents, as well as adjuvants, such as solvents, preservatives, stabilizers, wetting agents, emulsifiers and bulking agents, etc.

In certain embodiments, the pharmaceutical compositions provided herein comprise a plurality of granules each having an intragranular phase and an extragranular phase, and wherein said intragranular phase and extragranular phase of the granules each comprise sodium starch glycolate. The use of sodium starch glycolate in the intragranular phase and extragranular phase of the pharmaceutical compositions provided herein offer a number of advantages, including rapid disintegration, improved porosity, increased stability, and reduced rough surfaces, swelling, and cracking.

In one embodiment, the pharmaceutical compositions provided herein can be in any shape suitable for oral administration of Compound 1 or a pharmaceutically acceptable salt, stereoisomer or mixture of stereoisomers, tautomer, prodrug, hydrate, solvate, co-crystal, clathrate, or polymorph thereof, including but not limited to spheroidal, ovaloid, cubical, diamond, oblong, or ellipsoidal. In certain embodiments, the pharmaceutical composition provided herein is a tablet having the following dimensions: from about 20 mm to 25 mm in length, from about 15 mm to 19 mm across in length, from about 10 mm to 14 mm across in length, from about 5 mm to 9 mm across in length, and from about 1 mm to 4 mm across in length.

In addition to the active or therapeutic ingredients, pharmaceutical compositions provided herein may comprise at least one additional pharmaceutically acceptable excipient. Pharmaceutically acceptable excipients may be classified according to the role they play in the final pharmaceutical composition. For example, the composition of tablets comprise, but are not limited to, fillers, binders, disintegrants, lubricants, diluents, and glidants. These pharmaceutically acceptable excipients are added to provide the pharmaceutical composition provided herein with certain desirable physiochemical properties, such as flow and compression characteristics. Other pharmaceutically acceptable excipients may be added to a pharmaceutical composition provided herein to provide additional physical characteristics, such as coloring agents and flavoring agents. The choice of pharmaceutically acceptable excipients will depend on the chemical and physical characteristics of the active or therapeutic ingredient, behavior of the mixture during processing, and the properties of the final pharmaceutical composition.

Examples of fillers that are suitable for use in the pharmaceutical compositions provided herein include, but are not limited to, sugars (e.g., glucose, lactose, sucrose), magnesium stearate, calcium carbonate (e.g., granules, powder), and cellulose in various forms (e.g., microcrystalline cellulose, powdered cellulose) and derivatives thereof (e.g., methylcellulose, ethylcellulose, hydroxypropylcellulose, hydroxypropylmethylcellulose, sodium carboxymethyl cellulose), pre-gelatinized starch, and mixtures thereof.

Examples of binders that are suitable for use in the pharmaceutical compositions provided herein include, but are not limited to, sugars (e.g., glucose, lactose, sucrose), starches (e.g., corn starch, potato starch, pre-gelatinized or other starches), gelatin, natural and synthetic gums (e.g., acacia, tragacanth, guar gum, alginic acid), sorbitol, maltodextrin, sodium alginate or alginate derivatives, polyvinylpyrrolidone, and cellulose in various forms (e.g., microcrystalline cellulose, powdered cellulose) and derivatives thereof (e.g., methylcellulose, ethylcellulose, hydroxypropylcellulose, hydroxypropylmethylcellulose (also known as Cellulose HP M603), sodium carboxymethyl cellulose), and mixtures thereof. In a preferred embodiment, the binder is hydroxypropylmethylcellulose.

Examples of disintegrants that are suitable for use in the pharmaceutical compositions provided herein include, but are not limited to, starches (e.g., corn starch, potato starch, pre-gelatinized or other starches), sodium starch glycolate, clays, cellulose in various forms (e.g., microcrystalline cellulose, powdered cellulose) and derivatives thereof (e.g., methylcellulose, ethylcellulose, hydroxypropylcellulose, hydroxypropylmethylcellulose, sodium carboxymethyl cellulose), alginates, natural and synthetic gums (e.g., acacia, tragacanth, guar gum, alginic acid), cross-linked polymers (e.g., cross-linked polyvinylpyrrolidone (also known as crospovidone), cross-linked calcium carboxymethylcellulose, cross-linked sodium carboxymethylcellulose), soy polysaccharides, guar gum, and mixtures thereof. In a preferred embodiment, the disintegrant is sodium starch glycolate. In other preferred embodiments, the disintegrant is crospovidone.

Examples of lubricants that are suitable for use in the pharmaceutical compositions provided herein include, but are not limited to, colloidal silica, colloidal silicon dioxide (e.g., Aerosil 200), magnesium trisilicate, starches (e.g., corn starch, potato starch, pre-gelatinized or other starches), talc, tribasic calcium phosphate, magnesium stearate, aluminum stearate, calcium stearate, sodium stearyl fumarate, magnesium carbonate, magnesium oxide, polyethylene glycol, cellulose in various forms (e.g., microcrystalline cellulose, powdered cellulose) and derivatives thereof (e.g., methylcellulose, ethylcellulose, hydroxypropylcellulose, hydroxypropylmethylcellulose, sodium carboxymethyl cellulose), and mixtures thereof. In a preferred embodiment, the lubricant is sodium stearyl fumarate.

Examples of diluents that are suitable for use in the pharmaceutical compositions provided herein include, but are not limited to, confectioner's sugar, compressible sugar, sugars (e.g., lactose, dextrose, sucrose), dextrates, dextrin, mannitol, cellulose in various forms (e.g., microcrystalline cellulose, powdered cellulose) and derivatives thereof (e.g., methylcellulose, ethylcellulose, hydroxypropylcellulose, hydroxypropylmethylcellulose, sodium carboxymethyl cellulose), sorbitol, talc, and mixtures thereof. In a preferred embodiment, the diluent is collodial silicon dioxide (e.g., Aerosil 200).

Examples of glidants that are suitable for use in the pharmaceutical compositions provided herein include, but are not limited to, colloidal silicon dioxide (e.g., Aerosil 200), starches (e.g., corn starch, potato starch, pre-gelatinized or other starches), mannitol, magnesium trisilicate, cellulose in various forms (e.g., microcrystalline cellulose, powdered cellulose) and derivatives thereof (e.g., methylcellulose, ethylcellulose, hydroxypropylcellulose, hydroxypropylmethylcellulose, sodium carboxymethyl cellulose), talc, magnesium stearate, aluminum stearate, calcium stearate, and mixtures thereof. In a preferred embodiment, the glidant is mannitol, microcrystalline cellulose, or a combination thereof. In a more preferred embodiment, the glidant is mannitol.

Additional examples of useful pharmaceutically acceptable excipients which can optionally be added to the pharmaceutical compositions provided herein are described in the Handbook of Pharmaceutical Excipients, 6$^{th}$ edition, Edited by Raymond C. Rowe, Paul J. Sheskey, and Marian E. Quinn, Published by the Pharmaceutical Press and the American Pharmacists Association, Washington DC, ISBN: 978 1 58212 135 2 (USA), which is incorporated by reference herein in its entirety.

In one embodiment, the pharmaceutical compositions provided herein comprise (a) Compound 1 or a pharmaceutically acceptable salt, stereoisomer or mixture of stereoisomers, tautomer, prodrug, hydrate, solvate, co-crystal, clathrate, or polymorph thereof, (b) a disintegrant, (c) a lubricant, and (d) optionally, at least one pharmaceutically acceptable excipient. In certain preferred embodiments, the disintegrant is sodium starch glycolate. In other preferred embodiments, the disintegrant is crospovidone. In certain embodiments, the lubricant is sodium stearyl fumarate.

In one embodiment, the pharmaceutical compositions provided herein comprise (a) Compound 1 or a pharmaceutically acceptable salt, stereoisomer or mixture of stereoisomers, tautomer, prodrug, hydrate, solvate, co-crystal, clathrate, or polymorph thereof, (b) sodium starch glycolate, (c) sodium stearyl fumarate, and (d) optionally, at least one pharmaceutically acceptable excipient.

In one embodiment, the pharmaceutical compositions provided herein comprise (a) Compound 1 or a pharmaceutically acceptable salt, stereoisomer or mixture of stereoisomers, tautomer, prodrug, hydrate, solvate, co-crystal, clathrate, or polymorph thereof, (b) crospovidone, (c) sodium stearyl fumarate, and (d) optionally, at least one pharmaceutically acceptable excipient.

In one embodiment, the pharmaceutical compositions provided herein comprise (a) Compound 1 or a pharmaceutically acceptable salt, stereoisomer or mixture of stereoisomers, tautomer, prodrug, hydrate, solvate, co-crystal, clathrate, or polymorph thereof, (b) a disintegrant, (c) a lubricant, (d) at least one diluent, (e) a glidant, (f) a binder, (g) at least one pigment, and (h) optionally, at least one pharmaceutically acceptable excipient. In certain embodiments, the pharmaceutical compositions provided herein further comprise a second diluent.

In certain embodiments, Compound 1 is present in an amount ranging from about 40-50% by weight relative to the total weight of the composition, calculated based on its free base. In particular preferred embodiments, Compound 1 is present in an amount of 44% to 45% by weight relative to the total weight of the composition, calculated based on its free base.

In preferred embodiments, the disintegrant is sodium starch glycolate. In certain embodiments, sodium starch glycolate is present in an amount ranging from about 8% to 13% by weight relative to the total weight of the composition. In preferred embodiments, sodium starch glycolate is present in an amount ranging from about 11% to 12% by weight relative to the total weight of the composition. In other preferred embodiments, the disintegrant is crospovidone. In certain embodiments, crospovidone is present in an amount ranging from 6% to 10% by weight relative to the total weight of the composition. In preferred embodiments, crospovidone is present in an amount ranging from 8% to 9% by weight relative to the total weight of the composition.

In preferred embodiments, the lubricant is sodium stearyl fumarate. In certain embodiments, sodium stearyl fumarate is present in an amount ranging from about 1% to 3% by weight relative to the total weight of the composition. In preferred embodiments, sodium stearyl fumarate is present in an amount ranging from about 1% to 2% by weight relative to the total weight of the composition.

In preferred embodiments, the diluent is mannitol. In other preferred embodiments, the diluent is microcrystalline cellulose. In certain embodiments, the diluent is present in an amount ranging from about 22% to 30% by weight relative to the total weight of the composition. In other embodiments, a first diluent is present in an intragranular phase and a second diluent is present in the extragranular phase. In preferred embodiments, the first diluent is mannitol and the second diluent is microcrystalline celluose. In some embodiments, mannitol is present in an amount ranging from about 18% to 25% by weight relative to the total weight of the composition. In some embodiments, mannitol is present in an amount ranging from about 22% to 24% by weight relative to the total weight of the composition. In some embodiments, microcrystalline cellulose is present in an amount ranging from about 7% to 12% by weight relative to the total weight of the composition. In some embodiments, microcrystalline cellulose is present in an amount ranging from about 9% to 10% by weight relative to the total weight of the composition.

In certain embodiments, the glidant is colloidal silicon dioxide. In certain embodiments, colloidal silicon dioxide is present in an amount ranging from about 1% to 5% by weight relative to the total weight of the composition. In preferred embodiments, colloidal silicon dioxide is present in an amount ranging from about 2% to 4% by weight relative to the total weight of the composition.

In certain embodiments, the pigment is present in an amount ranging from about 3% to 5% by weight relative to the total weight of the composition.

In preferred embodiments, the binder is hydroxypropyl methylcellulose.

In certain embodiments, the pharmaceutical compositions provided herein further comprise at least one pharmaceutically acceptable excipient wherein the excipient is a diluent, a glidant, or a combination thereof. In some embodiments, the pharmaceutical compositions provided herein further comprise a diluent. In some embodiments, the diluent is mannitol, microcrystalline cellulose, or a combination thereof. In preferred embodiments, the diluent is mannitol. In other preferred embodiments, the diluent is microcrystalline cellulose. In certain embodiments, the pharmaceutical compositions provided herein further comprise a glidant. In some embodiments, the glidant is colloidal silicon dioxide.

In some embodiments, the pharmaceutical compositions provided herein comprise a crystalline form of Compound 1. Embodiments of the crystalline form of Compound 1 provided herein include the form designated as Form A. The names used herein to identify a specific form, e.g. "Form A", etc., should not be considered limiting with respect to any other substance possessing similar or identical physical and chemical characteristics, but rather it should be understood that these designations are mere identifiers that should be interpreted according to the characterization information also presented herein.

Figure 3:
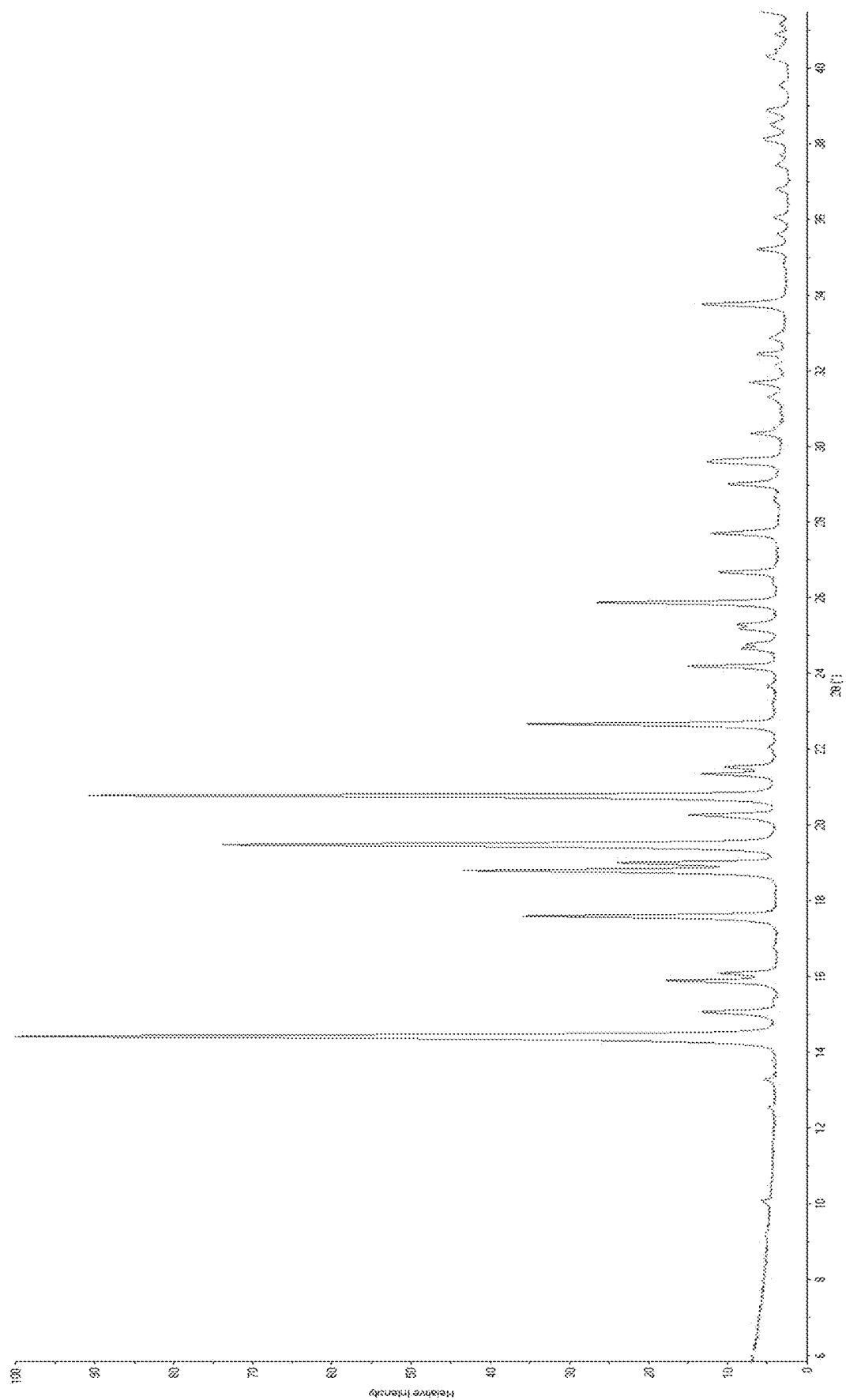
FIG. 3 provides an illustrative X-ray powder diffraction pattern (XRPD) of the crystalline form of Compound 1, designated herein as Form A, showing degrees 2θ (2-theta) on the X-axis and relative intensity on the Y-axis. More detailed listings of the XRPD peaks for Form A are set forth in Table 1 in Section 7.1, Example 1.

In certain embodiment, the pharmaceutical compositions provided herein comprise a Form A having an X-ray powder diffraction (XRPD) spectrum substantially the same as the XRPD shown in FIG. 3. In other embodiments, the pharmaceutical composition comprises Form A characterized by an XRPD pattern comprising one or more peaks selected from 14.4, 15.8, 17.5 19.4 20.1 20.7 21.5, 25.2, 25.8, 33.7±0.2° 2θ. Accordingly, the XRPD pattern for Form A may comprise one, two, three, or four representative peaks. In other embodiments, the pharmaceutical composition comprises Form A characterized by an XRPD pattern comprising one or more peaks selected from FIG. 3, as shown in Table 1 in Example 1 below.

Figure 4:
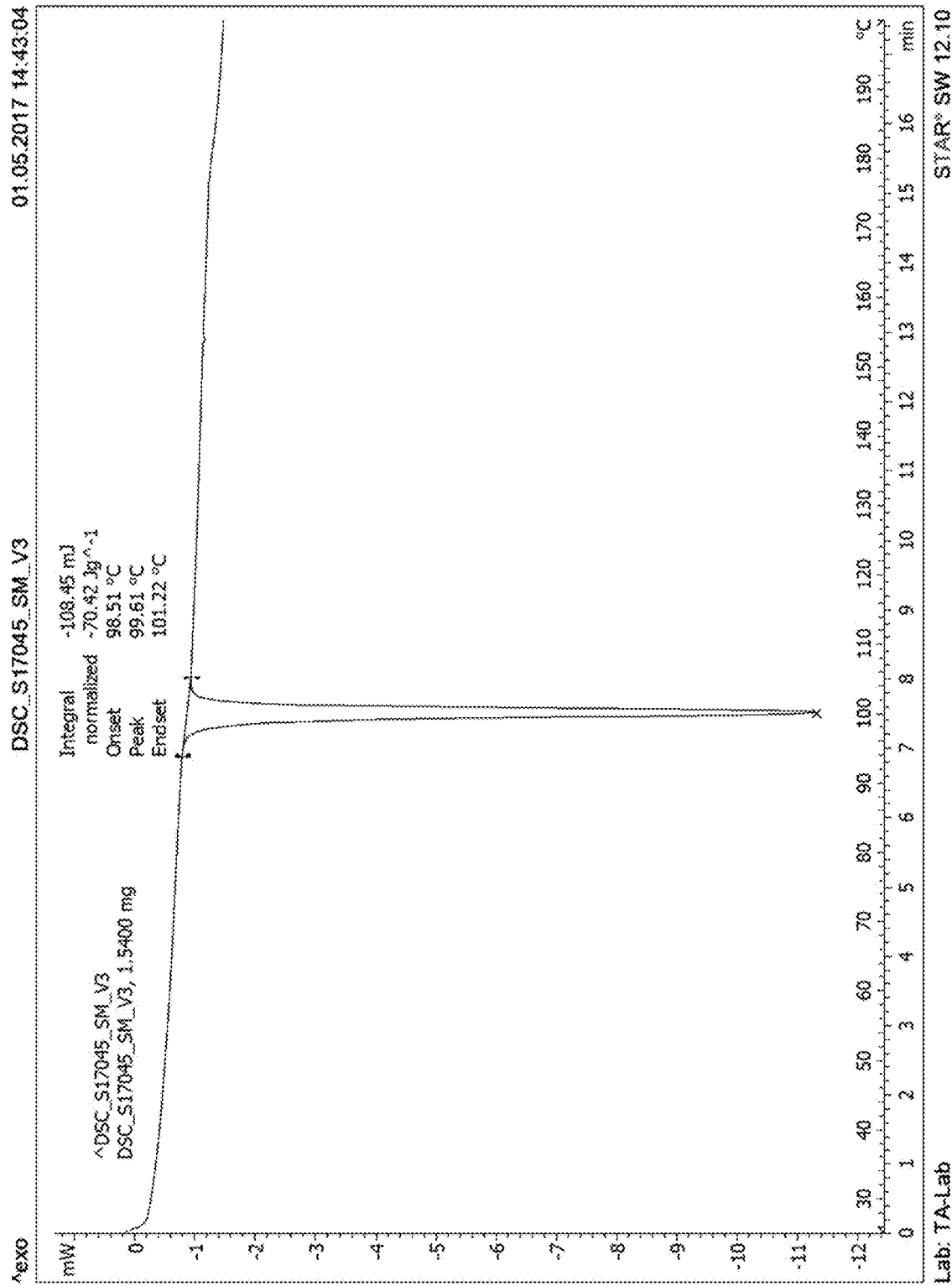
FIG. 4 provides an illustrative differential scanning calorimetry (DSC) profile of the crystalline form of Compound 1, designated herein as Form A. The DSC graph plots the heat flow as a function of temperature from a sample, the temperature rate change being about 10 K/min.

In another embodiment, the pharmaceutical compositions provided herein comprise Form A having a differential scanning calorimetry (DSC) profile substantially the same as the DSC profile shown in FIG. 4. In certain embodiments, the DSC profile is characterized by a single endothermic event representing the melting of the compound with a melting onset at about 98.5° C. at a heating rate of 10 K/min.

Figure 5:
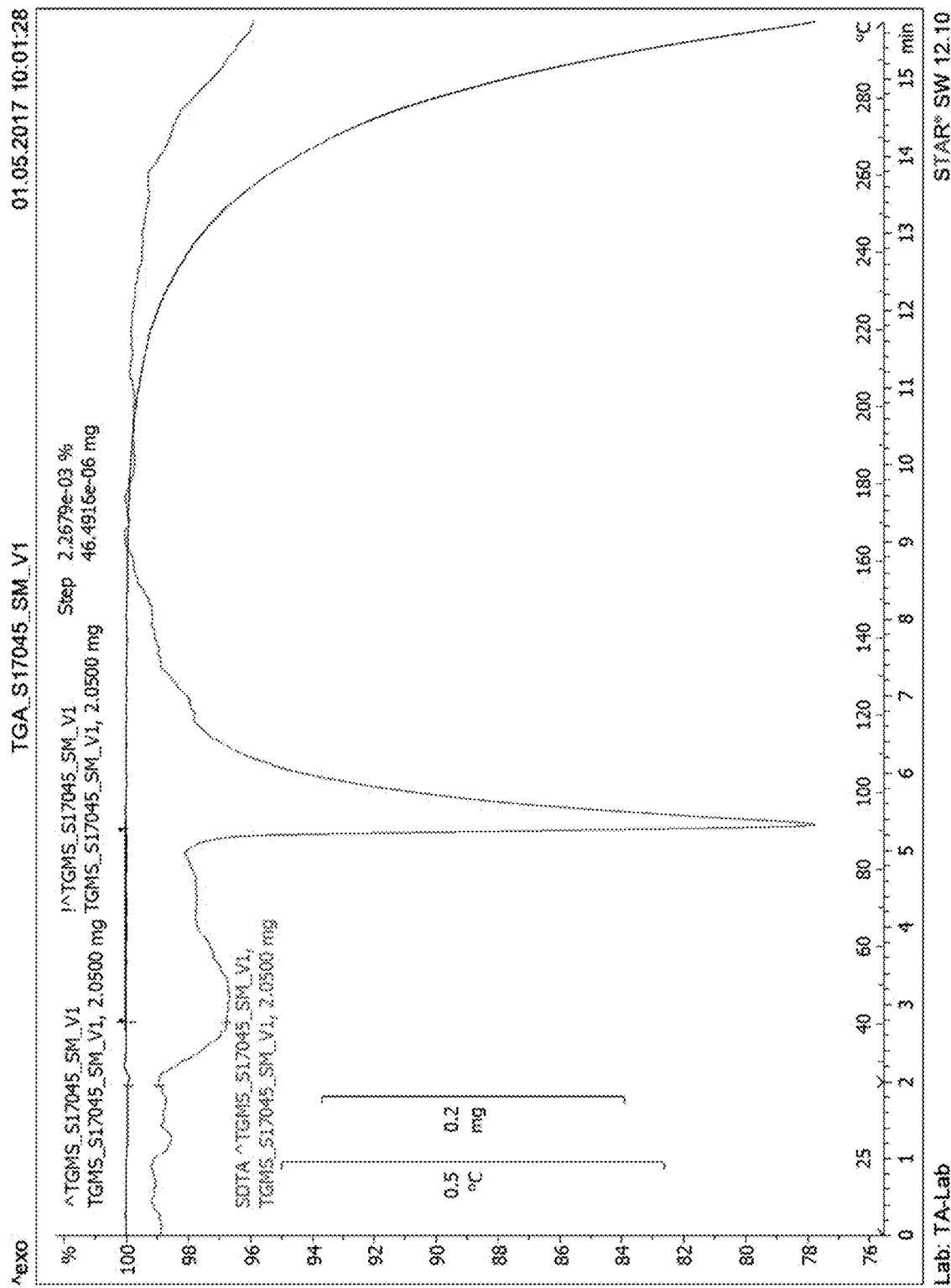
FIG. 5 provides an illustrative thermo gravimetric analysis (TGA) profile of the crystalline of Compound 1, designated herein as Form A. The TGA profile graphs the percent loss of weight of the sample as a function of temperature, the temperature rate change being about 10 K/min.

In another embodiment, the pharmaceutical compositions provided herein comprise Form A having a thermo gravimetric analysis (TGA) profile substantially the same as the TGA profile shown in FIG. 5. In certain embodiments, the weight loss represents a loss of about 0.0025% of the sample as the temperature is changed from about 30° C. to about 100° C. In certain embodiments, the weight loss represents a loss of less than about 0.0025% of the sample as the temperature is changed from about 30° C. to about 100° C.

In other embodiments, Form A is a besylate salt of (S)-3-amino-6-methoxy-N-(3,3,3-trifluoro-2-hydroxy-2-methylpropyl)-5-(trifluoromethyl)picolinamide. In certain embodiments, Form A is substantially pure.

It should be understood that in the XRPD spectra or pattern that there is inherent variability in the values measured in degrees 2theta (°2θ) as a result of, for example, instrumental variation (including differences between instruments). As such, it should be understood that there is a variability of up to ±0.2° 2θ in XRPD peak measurements and yet such peak values would still be considered to be representative of a particular solid state form of the crystalline materials described herein. It should also be understood that other measured values from XRPD experiments and Karl Fisher analysis, such as relative intensity and water content, can vary as a result of, for example, sample preparation and/or storage and/or environmental conditions, and yet the measured values will still be considered to be representative of a particular solid state form of the crystalline materials described herein.

In other embodiments, the pharmaceutical compositions provided herein comprise an amorphous form of (S)-3-amino-6-methoxy-N-(3,3,3-trifluoro-2-hydroxy-2-methylpropyl)-5-(trifluoromethyl)picolinamide. In other embodiments, the amorphous form is a besylate salt of (S)-3-amino-6-methoxy-N-(3,3,3-trifluoro-2-hydroxy-2-methylpropyl)-5-(trifluoromethyl)picolinamide.

5.3. Preparation of Pharmaceutical Compositions of Compound 1

The pharmaceutical compositions provided herein may be manufactured by a process comprising the step of wet granulation using a high shear granulator. Wet granulation is a manufacturing process that binds various components of a pharmaceutical composition together using a binder liquid. Examples of binder liquids include, but are not limited to, water, alcohols, and combinations thereof. In a preferred embodiment, the binder liquid is water.

In certain embodiments, provided herein is a process for the manufacture of a pharmaceutical composition comprising Compound 1, comprising the steps of (a) blending Compound 1 or a pharmaceutically acceptable salt, stereoisomer or mixture of stereoisomers, tautomer, prodrug, hydrate, solvate, co-crystal, clathrate, or polymorph thereof together with a disintegrant and optionally at least one pharmaceutically acceptable carrier to form a material, (b) wet milling the material to form a plurality of granules, (c) blending the granules with a lubricant and a disintegrant and optionally at least one pharmaceutically acceptable carrier to form a final blend, and (c) compressing the final blend into a tablet. In certain preferred embodiments, the disintegrant is sodium starch glycolate and the lubricant is sodium stearyl fumarate. In other embodiments, the disintegrant is crospovidone and the lubricant is sodium stearyl fumarate.

In certain embodiments, provided herein is a process for the manufacture of the pharmaceutical composition comprising Compound 1 comprising the steps of: (a) blending Compound 1 or a pharmaceutically acceptable salt, stereoisomer or mixture of stereoisomers, tautomer, prodrug, hydrate, solvate, co-crystal, clathrate, or polymorph thereof together with sodium starch glycolate and optionally at least one pharmaceutically acceptable carrier to form a material, (b) wet milling the material to form a plurality of granules, (c) blending the granules with sodium stearyl fumarate and sodium starch glycolate and optionally at least one pharmaceutically acceptable carrier to form a final blend, and (d) compressing the final blend into a tablet.

In certain embodiments, the pharmaceutical compositions provided herein is produced by the process provided herein. In other embodiments, the pharmaceutical compositions provided herein for use in the treatment of a respiratory disease or disorder is produced by the processes provided herein. In certain embodiments, the respiratory disease or disorder is COPD, CF, bronchiectasis, chronic bronchitis or asthma. In preferred embodiments, pharmaceutical compositions provided herein for use in the treatment of COPD, CF, bronchiectasis, chronic bronchitis or asthma is produced by the processes provided herein.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms, including polymorphs. Crystals of drugs, including polymorphs, methods of preparation, and characterization of drug crystals are discussed in Solid-State Chemistry of Drugs, S. R. Byrn, R. R. Pfeiffer, and J. G. Stowell, 2nd Edition, SSCI, West Lafayette, Indiana (1999). The presence of more than one polymorph in a sample may be determined by techniques such as x-ray powder diffraction (XRPD) or solid state nuclear magnetic resonance spectroscopy. For example, the presence of extra peaks in the comparison of an experimentally measured PXRD pattern with a simulated XRPD pattern may indicate more than one polymorph in the sample. The simulated XRPD may be calculated from single crystal x-ray data. see Smith, D. K., "A FORTRAN Program for Calculating X-Ray Powder Diffraction Patterns," Lawrence Radiation Laboratory, Livermore, California, UCRL-7196 (April 1963) or TOPAS program (Total Pattern Analysis Solution, available through Brucker AXS Inc.).

5.4. Methods of Treatment

In certain embodiments, provided herein is a method for treating a subject in need thereof comprising administering the pharmaceutical composition provided herein to the subject.

In certain embodiments, provided herein is a method for the treatment of a respiratory disease or disorder comprising administering the pharmaceutical composition provided herein to a subject in need thereof. In particular embodiments, the respiratory disease or disorder is COPD, CF, bronchiectasis, chronic bronchitis or asthma. In preferred embodiments, the respiratory disease or disorder is COPD. In other preferred embodiments, the respiratory disease or disorder is bronchiectasis. In certain embodiments, the composition is administered to the subject without a high fat meal. In preferred embodiments, the high fat meal has not been consumed for about 30 minutes prior to administration of the composition to the subject. In other preferred embodiments, the high fat meal has not been consumed together with administration of the composition to the subject. In certain embodiments, administration results in a lower maximal plasma concentration (Cmax) and extent of exposure (AUClast or AUCinf) of Compound 1 as compared to administration with a high fat meal. In other embodiments, the composition comprises an amount equal to about 450 mg of Compound 1 or a pharmaceutically acceptable salt, polymorph or co-crystal thereof. In other embodiments, the composition comprises an amount equal to about 400 mg of Compound 1 or a pharmaceutically acceptable salt, polymorph or co-crystal thereof. In other embodiments, the composition comprises an amount equal to about 300 mg of Compound 1 or a pharmaceutically acceptable salt, polymorph or co-crystal thereof. In other embodiments, the composition comprises an amount equal to about 150 mg of Compound 1 or a pharmaceutically acceptable salt, polymorph or co-crystal thereof. In other embodiments, the composition comprises an amount equal to about 75 mg of Compound 1 or a pharmaceutically acceptable salt, polymorph or co-crystal thereof. In certain embodiments, the composition is administered in two oral doses per day.

In certain embodiments of the methods provided herein, administration of (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof to a subject leads to formation of metabolites. In some embodiments, the metabolic reactions to form the metabolites are acetylation, formation of a carboxylic acid, C-hydroxylation, glucuronidation, N-dealkylation, N-glucuronidation, N-oxidation, 0-demethylation, 0-glucuronidation, oxygenation, sulfation or combinations thereof. In other embodiments, the metabolic reactions were C-hydroxylation, glucuronidation, N-dealkylation, N-glucuronidation, 0-demethylation, 0-glucuronidation, or combinations thereof.

Without being bound by any theory, the biotransformation pathways in a subject are illustrated in FIGS. 11 and 12. In certain embodiments of the methods provided herein, the metabolites are M1, M3, M5, M6, M7, M8, M9, M10, M14, M17, M22, M24, M27, M28, M29, M31, M32, M33 or combinations thereof. In other embodiments, the metabolites are M5, M8, M9, M10, M14, M17 or combinations thereof.

In certain embodiments, provided herein is a method for promoting mucus clearance in a subject with a respiratory disease or disorder comprising administering the pharmaceutical composition provided herein to a subject in need thereof. In particular embodiments, the respiratory disease or disorder is COPD, CF, bronchiectasis, chronic bronchitis or asthma. In preferred embodiments, the respiratory disease or disorder is COPD. In other preferred embodiments, the respiratory disease or disorder is bronchiectasis. In certain embodiments, the composition is administered to the subject without a high fat meal. In preferred embodiments, the high fat meal has not been consumed for about 30 minutes prior to administration of the composition to the subject. In other preferred embodiments, the high fat meal has not been consumed together with administration of the composition to the subject. In certain embodiments, administration results in a lower maximal plasma concentration (Cmax) and extent of exposure (AUClast or AUCinf) of Compound 1 as compared to administration with a high fat meal. In other embodiments, the composition comprises an amount equal to about 450 mg of Compound 1 or a pharmaceutically acceptable salt, polymorph or co-crystal thereof. In other embodiments, the composition comprises an amount equal to about 400 mg of Compound 1 or a pharmaceutically acceptable salt, polymorph or co-crystal thereof. In other embodiments, the composition comprises an amount equal to about 300 mg of Compound 1 or a pharmaceutically acceptable salt, polymorph or co-crystal thereof. In other embodiments, the composition comprises an amount equal to about 150 mg of Compound 1 or a pharmaceutically acceptable salt, polymorph or co-crystal thereof. In other embodiments, the composition comprises an amount equal to about 75 mg of Compound 1 or a pharmaceutically acceptable salt, polymorph or co-crystal thereof. In certain embodiments, the composition is administered in two oral doses per day.

In certain embodiments, provided herein is a method for promoting mucus clearance in a subject with COPD, CF, bronchiectasis, chronic bronchitis or asthma comprising administering the pharmaceutical composition provided herein to a subject in need thereof. In certain embodiments, the composition is administered to the subject without a high fat meal. In preferred embodiments, the high fat meal has not been consumed for about 30 minutes prior to administration of the composition to the subject. In other preferred embodiments, the high fat meal has not been consumed together with administration of the composition to the subject. In certain embodiments, administration results in a lower maximal plasma concentration (Cmax) and extent of exposure (AUClast or AUCinf) of Compound 1 as compared to administration with a high fat meal. In other embodiments, the composition comprises an amount equal to about 450 mg of Compound 1 or a pharmaceutically acceptable salt, polymorph or co-crystal thereof. In other embodiments, the composition comprises an amount equal to about 400 mg of Compound 1 or a pharmaceutically acceptable salt, polymorph or co-crystal thereof. In other embodiments, the composition comprises an amount equal to about 300 mg of Compound 1 or a pharmaceutically acceptable salt, polymorph or co-crystal thereof. In other embodiments, the composition comprises an amount equal to about 150 mg of Compound 1 or a pharmaceutically acceptable salt, polymorph or co-crystal thereof. In other embodiments, the composition comprises an amount equal to about 75 mg of Compound 1 or a pharmaceutically acceptable salt, polymorph or co-crystal thereof. In certain embodiments, the composition is administered in two oral doses per day.

In certain embodiments, provided herein is a method for the treatment of bronchiectasis, chronic obstructive pulmonary disorder, cystic fibrosis, chronic bronchitis or asthma, comprising administering Compound 1 to a subject in need thereof, wherein Compound 1 is administered to the subject without a high fat meal. In preferred embodiments, the high fat meal has not been consumed for about 30 minutes prior to administration of Compound 1 to the subject. In other preferred embodiments, the high fat meal has not been consumed together with administration of Compound 1 to the subject. In some embodiments, administration results in a lower maximal plasma concentration (Cmax) and extent of exposure (AUClast or AUCinf) of Compound 1 as compared to administration with a high fat meal. In some embodiments, Compound 1 is administered in a pharmaceutical composition. In some embodiments, the composition comprises an amount equal to about 450 mg of Compound 1 or a pharmaceutically acceptable salt, polymorph or co-crystal thereof. In other embodiments, the composition comprises an amount equal to about 400 mg of Compound 1 or a pharmaceutically acceptable salt, polymorph or co-crystal thereof. In some embodiments, the composition comprises an amount equal to about 300 mg of Compound 1 or a pharmaceutically acceptable salt, polymorph or co-crystal thereof. In some embodiments, the composition comprises an amount equal to about 150 mg of Compound 1 or a pharmaceutically acceptable salt, polymorph or co-crystal thereof. In some embodiments, the composition comprises an amount equal to about 75 mg of Compound 1 or a pharmaceutically acceptable salt, polymorph or co-crystal thereof. In certain embodiments, the composition is administered in two oral doses per day.

In certain embodiments, provided herein is a method for promoting mucus clearance in a subject with bronchiectasis, chronic obstructive pulmonary disorder, cystic fibrosis, chronic bronchitis or asthma comprising administering Compound 1 to a subject in need thereof, wherein Compound 1 is administered to the subject without a high fat meal. In preferred embodiments, the high fat meal has not been consumed for about 30 minutes prior to administration of Compound 1 to the subject. In other preferred embodiments, the high fat meal has not been consumed together with administration of Compound 1 to the subject. In some embodiments, administration results in a lower maximal plasma concentration (Cmax) and extent of exposure (AUClast or AUCinf) of Compound 1 as compared to administration with a high fat meal. In some embodiments, Compound 1 is administered in a pharmaceutical composition. In some embodiments, the composition comprises an amount equal to about 450 mg of Compound 1 or a pharmaceutically acceptable salt, polymorph or co-crystal thereof. In other embodiments, the composition comprises an amount equal to about 400 mg of Compound 1 or a pharmaceutically acceptable salt, polymorph or co-crystal thereof. In some embodiments, the composition comprises an amount equal to about 300 mg of Compound 1 or a pharmaceutically acceptable salt, polymorph or co-crystal thereof. In some embodiments, the composition comprises an amount equal to about 150 mg of Compound 1 or a pharmaceutically acceptable salt, polymorph or co-crystal thereof. In some embodiments, the composition comprises an amount equal to about 75 mg of Compound 1 or a pharmaceutically acceptable salt, polymorph or co-crystal thereof. In certain embodiments, the composition is administered in two oral doses per day.

In certain embodiments, provided herein is a method of lowering the oral bioavailability of Compound 1 in a subject receiving Compound 1 comprising administering to the subject a therapeutically effective amount of Compound 1 without a high fat meal. In preferred embodiments, the high fat meal has not been consumed for about 30 minutes prior to administration of Compound 1 to the subject. In other preferred embodiments, the high fat meal has not been consumed together with administration of Compound 1 to the subject. In some embodiments, Compound 1 is administered in a pharmaceutical composition. In some embodiments, administration results in a lower maximal plasma concentration (Cmax) and extent of exposure (AUClast or AUCinf) of Compound 1 as compared to administration with a high fat meal. In some embodiments, Compound 1 is administered in a pharmaceutical composition. In some embodiments, the composition comprises an amount equal to about 450 mg of Compound 1 or a pharmaceutically acceptable salt, polymorph or co-crystal thereof. In other embodiments, the composition comprises an amount equal to about 400 mg of Compound 1 or a pharmaceutically acceptable salt, polymorph or co-crystal thereof. In some embodiments, the composition comprises an amount equal to about 300 mg of Compound 1 or a pharmaceutically acceptable salt, polymorph or co-crystal thereof. In some embodiments, the composition comprises an amount equal to about 150 mg of Compound 1 or a pharmaceutically acceptable salt, polymorph or co-crystal thereof. In some embodiments, the composition comprises an amount equal to about 75 mg of Compound 1 or a pharmaceutically acceptable salt, polymorph or co-crystal thereof. In certain embodiments, the composition is administered in two oral doses per day.

In certain embodiments, provided herein is use of the pharmaceutical composition provided herein for the treatment of a respiratory disease or disorder. In particular embodiments, the respiratory disease or disorder is COPD, CF, bronchiectasis, chronic bronchitis or asthma. In certain embodiments, provided herein is a use of the pharmaceutical composition provided herein for the treatment of COPD, CF, bronchiectasis, chronic bronchitis or asthma.

In certain embodiments, provided herein is use of the pharmaceutical composition provided herein for the manufacture of a medicament for the treatment of a respiratory disease or disorder. In particular embodiments, the respiratory disease or disorder is COPD, CF, bronchiectasis, chronic bronchitis or asthma. In certain embodiments, provided herein is a use of the pharmaceutical composition provided herein for the manufacture of a medicament for the treatment of COPD, CF, bronchiectasis, chronic bronchitis or asthma.

In certain embodiments, provided herein is a pharmaceutical composition as disclosed herein for use in the treatment of bronchiectasis, chronic obstructive pulmonary disorder, cystic fibrosis, chronic bronchitis or asthma. In some embodiments, the pharmaceutical composition is administered to a subject without a high fat meal. In preferred embodiments, the high fat meal has not been consumed for about 30 minutes prior to administration of the composition to the subject. In other preferred embodiments, the high fat meal has not been consumed together with administration of the composition to the subject. In some embodiments, administration results in a lower maximal plasma concentration (Cmax) and extent of exposure (AUClast or AUCinf) of Compound 1 as compared to administration with a high fat meal.

In certain embodiments, provided herein is Compound 1 or a pharmaceutically acceptable salt, polymorph or co-crystal thereof for use in the treatment of bronchiectasis, chronic obstructive pulmonary disorder, cystic fibrosis, chronic bronchitis or asthma, wherein Compound 1 is administered without a high fat meal. In preferred embodiments, the high fat meal has not been consumed for about 30 minutes prior to administration of Compound 1 to the subject. In other preferred embodiments, the high fat meal has not been consumed together with administration of Compound 1 to the subject. In some embodiments, administration results in a lower maximal plasma concentration (Cmax) and extent of exposure (AUClast or AUCinf) of Compound 1 as compared to administration with a high fat meal.

In certain embodiments, the composition is administered to the subject without a high fat meal. In other embodiments, the composition is administered to the subject without a high fat meal, wherein the high fat meal has not been consumed for about 10 hours, about 8 hours, about 6 hours, about 4 hours, about 2 hours, about 1 hour, about 30 minutes, about 15 minutes, about 5 minutes or about 1 minute prior to administration of the composition to the subject. In preferred embodiments, the high fat meal has not been consumed for about 30 minutes prior to administration of the composition to the subject. In other preferred embodiments, the high fat meal has not been consumed together with administration of the composition to the subject. In other embodiments, Compound 1 is administered to the subject without a high fat meal, wherein the high fat meal has not been consumed for about 10 hours, about 8 hours, about 6 hours, about 4 hours, about 2 hours, about 1 hour, about 30 minutes, about 15 minutes, about 5 minutes or about 1 minute prior to administration of Compound 1 to the subject. In preferred embodiments, the high fat meal has not been consumed for about 30 minutes prior to administration of Compound 1 to the subject. In other preferred embodiments, the high fat meal has not been consumed together with administration of Compound 1 to the subject. In some embodiments, Compound 1 is administered in a pharmaceutical composition.

In some embodiments, the composition is administered to the subject in a fasted state. In other embodiments, the composition is administered to the subject in a fasted state wherein food has not been consumed for about 10 hours, about 8 hours, about 6 hours, about 4 hours, about 2 hours, about 1 hour, or about 30 minutes prior to administration of the composition to the subject. In preferred embodiments, food has not been consumed for about 10 hours prior to administration of the composition to the subject. In other embodiments, Compound 1 is administered to the subject in a fasted state wherein food has not been consumed for about 10 hours, about 8 hours, about 6 hours, about 4 hours, about 2 hours, about 1 hour, or about 30 minutes prior to administration of Compound 1 to the subject. In preferred embodiments, food has not been consumed for about 10 hours prior to administration of Compound 1 to the subject. In some embodiments, Compound 1 is administered in a pharmaceutical composition.

In some embodiments, the composition is administered to the subject in a fed state. In other embodiments, the composition is administered to the subject in a fed state, wherein food has been consumed within about 10 hours, about 8 hours, about 6 hours, about 4 hours, about 2 hours, about 1 hour, or about 30 minutes prior to administration of the composition to the subject. In other embodiments, Compound 1 is administered to the subject in a fed state, wherein food has been consumed within about 10 hours, about 8 hours, about 6 hours, about 4 hours, about 2 hours, about 1 hour, or about 30 minutes prior to administration of Compound 1 to the subject. In particular embodiments, Compound 1 is administered to the subject in a fed state, wherein food has been consumed within about 30 minutes prior to administration of Compound 1 to the subject. In some embodiments, Compound 1 is administered in a pharmaceutical composition.

In any embodiment provided herein, the bioavailability of Compound 1 or pharmaceutically acceptable salt, polymorph or co-crystal thereof is lowered compared to the bioavailability of the same amount of Compound 1 or pharmaceutically acceptable salt, polymorph or co-crystal thereof when administered with a high fat meal. Lowering the bioavailability comprises lowering the maximal plasma concentration (Cmax) or the extent of exposure (AUClast or AUCinf) of Compound 1 or pharmaceutically acceptable salt, polymorph or co-crystal thereof. In any embodiment provided herein, the lowering of the bioavailability of Compound 1 comprises a lowering of Cmax in the range of about 26% to about 34% and an increase in AUC in the range of about 40% to about 49% for Compound 1 or pharmaceutically acceptable salt, polymorph or co-crystal thereof when taken during a fasted condition compared to the same amount of Compound 1 or pharmaceutically acceptable salt, polymorph or co-crystal thereof taken with a high fat meal.

6. INCORPORATION BY REFERENCE

The entire disclosure of each of the patent documents and scientific articles cited herein is incorporated by reference for all purposes.

7. EXAMPLES

The pharmaceutical compositions provided herein are further illustrated by the following examples which are not intended to limit the scope of the invention.

7.1. Example 1: Form A of Compound 1

Figure 6:
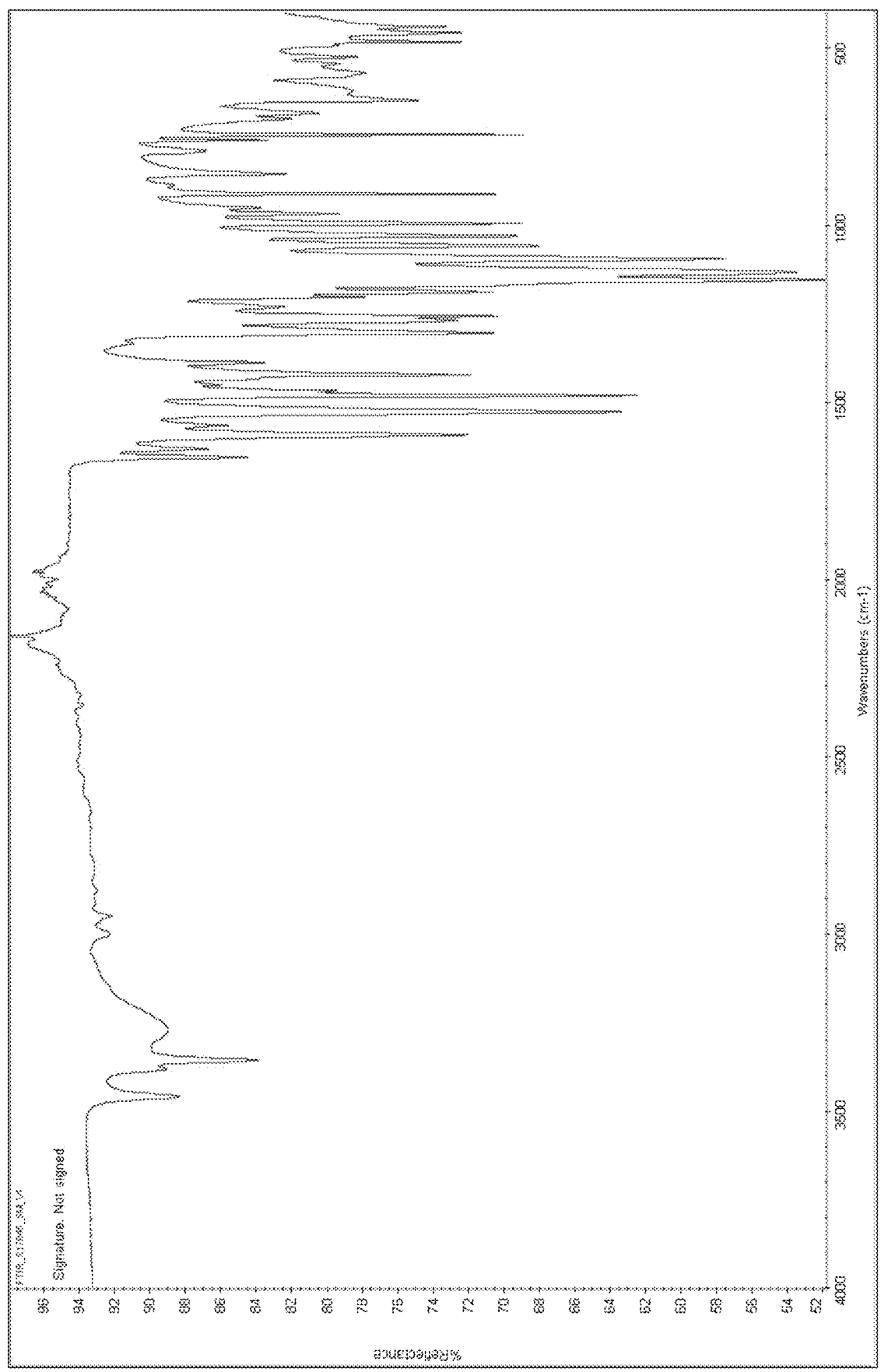
FIG. 6 illustrates the FT-IR spectrum of the crystalline form of Compound 1, designated herein as Form A.

A 300 mg/mL solution of Compound 1 was prepared in a 1:1 toluene and heptane solution at 60° C. The solution was placed in an ice bath and agitated until precipitates formed. Upon completion of precipitate formation, the resulting solids were collected using a filter and dried to provide Form A. The characterization of Form A was conducted using XRPD, DSC, and TGA techniques. The structure of Compound 1 was confirmed using FT-IR as illustrated in FIG. 6.

7.1.1. X-Ray Powder Diffraction

The X-ray powder diffraction (XRPD) data was collected on a D8 Advance diffractometer using CuKα1 radiation (1.54056 Å) with germanium monochromator at room temperature. The data were collected from 4 to 41.5° 2θ. Detector scan on solid state LynxEye detector was performed using 0.016° per step with 3 s/step scan speed. The sample was measured in an 8 mm long glass capillary with 0.3 mm outer diameter. FIG. 3 illustrates the XRPD of Form A.

TABLE 1

X-ray powder diffraction data for Form A.

| Angle/ °2theta | Intensity/ % |
| --- | --- |
| 10.0 | 9.4 |
| 12.5 | 2.6 |
| 13.2 | 3.2 |
| 14.4 | 22.2 |
| 15.0 | 3.4 |
| 15.8 | 25.6 |
| 17.5 | 71.3 |
| 18.8 | 12.1 |
| 19.0 | 12.7 |
| 19.4 | 100 |
| 20.1 | 24.7 |
| 20.7 | 54.8 |
| 21.5 | 24.3 |
| 22.6 | 17.9 |
| 23.6 | 6.9 |
| 24.1 | 9.6 |
| 24.7 | 10.7 |
| 25.2 | 48.4 |
| 25.8 | 26.2 |
| 26.6 | 14.0 |
| 27.7 | 13.9 |
| 29.0 | 6.9 |
| 29.6 | 14.1 |
| 30.4 | 8.3 |
| 31.6 | 9.8 |
| 32.4 | 5.8 |

TABLE 1-continued

X-ray powder diffraction data for Form A.

| Angle/ °2theta | Intensity/ % |
|---|---|
| 32.9 | 8.1 |
| 33.7 | 20.6 |

7.1.2. Differential Scanning Calorimetry

Melting properties of Form A were obtained from differential scanning calorimetry (DCA) thermograms, recorded with a heat flux DSC822e instrument (Mettler-Toledo GmbH, Switzerland). Samples were sealed in standard 40 aluminum pans, pin-holed and heated in the DSC from 25° C. to 200° C., at a heating rate of 10 K/min. Dry N2 gas, at a flow rate of 50 mL/min was used to purge the DSC equipment during the measurement. FIG. 4 illustrates the DSC profile of Form A.

7.1.3. Thermo Analysis

Form A was analyzed using thermogravimetry analysis (TGA). Loss on drying was determined by TGA/SDTA using a TGA/SDTA851e instrument (Mettler-Toledo GmbH, Switzerland), resulting in a weight vs. temperature curve. Samples were weighed into 100 μL aluminum crucibles and sealed. The seals were pin-holed and the crucibles heated in the TGA from 25° C. to 300° C. at a heating rate of 20° C./min. Dry N2 gas was used for purging. FIG. 5 illustrates the TGA profile of Form A.

7.1.4. FTIR-ATR Analysis

The FTIR-ATR spectrum was obtained using a Thermo Fischer Scientific FT-IR: Nicolet 6700 with a resolution of 4 cm-1. FIG. 5 illustrates the FTIR spectrum of Form A. Characteristic peaks are listed in Table 2 below.

TABLE 2

FTIR-ATR data for Form A.

| Wavenumber/ $cm^{-1}$ | Reflectance/ % |
|---|---|
| 3460 | 88 |
| 3381 | 89 |
| 3356 | 84 |
| 3273 | 89 (broad) |
| 1654 | 84 |
| 1590 | 72 |
| 1526 | 64 |
| 1480 | 62 |
| 1421 | 72 |
| 1303 | 70 |
| 1257 | 70 |
| 1188 | 70 |
| 1153 | 52 |
| 1133 | 53 |
| 1095 | 57 |
| 1056 | 68 |
| 1029 | 69 |
| 993 | 69 |
| 911 | 70 |
| 854 | 82 |
| 744 | 69 |
| 646 | 75 |
| 456 | 77 |

7.2. Example 2: 75 mg, 150 mg, 300 mg, 450 mg Film-Coated Tablet Formulation Table 3 illustrates the formulation for 75 mg and 450 mg film-coated tablets of Formulation A (i.e., 44.91% by weight of Compound 1 calculated based on its free base relative to the total weight of the composition).

Table 4 illustrates the formulation for 75 mg, 150 mg, 300 mg, and 450 mg film-coated tablets of Formulation (i.e., 44.91% by weight of Compound 1 calculated based on its free base relative to the total weight of the composition).

TABLE 3

75 mg and 450 mg Compound 1 Film-Coated Tablet Formulation A

| Ingredient | % w/w | Quantity (mg) | Quantity (mg) |
|---|---|---|---|
| Intragranular Phase | | | |
| Compound 1 (free base) | 44.90% | 74.98 | 449.86 |
| Mannitol | 23.08% | 38.54 | 231.26 |
| Crospovidone | 3.87% | 6.47 | 38.81 |
| Hypromellose | 4.8% | 8.05 | 48.31 |
| Silica, colloidal anhydrous/ Colloidal silicon dioxide | 2.4% | 3.96 | 23.76 |
| Purified water (removed during processing) | — | — | — |
| Total Intragranular Phase | | 132.00 | 792.00 |
| Extragranular Phase | | | |
| Cellulose, microcrystalline/ Microcrystalline cellulose | 9.58% | 16.00 | 96.00 |
| Crospovidone | 4.79% | 8.00 | 48.00 |
| Silica, colloidal anhydrous/ colloidal silicon dioxide | 0.48% | 0.80 | 4.80 |
| Sodium stearyl fumarate | 1.92% | 3.20 | 19.20 |
| Total Core Tablet Weight | | 160.00 | 960.00 |
| Film Coating | | | |
| Coating premix, yellow | 2.47% | 4.13 | 13.57 |
| Coating premix, red | 0.75% | 1.26 | 4.14 |

TABLE 3-continued 75 mg and 450 mg Compound 1 Film-Coated Tablet Formulation A

| Ingredient | % w/w | Quantity (mg) | Quantity (mg) |
|---|---|---|---|
| Coating premix, white | 0.75% | 1.26 | 4.14 |
| Coating premix, black | 0.21% | 0.35 | 1.15 |
| Purified water (removed during processing) | — | — | — |
| Total Film Coated Tablet Weight | 100.00% | 167.00 | 983.00 |

TABLE 4

75 mg, 150 mg, 300 mg, 450 mg Compound 1 Film-Coated Tablet Formulation B

| Ingredient | % w/w | Quantity (mg) | Quantity (mg) | Quantity (mg) | Quantity (mg) |
|---|---|---|---|---|---|
| Intragranular Phase | | | | | |
| Compound 1 (free base) | 44.91% | 75.00 | 150.00 | 300.00 | 450.00 |
| Mannitol | 20.24% | 33.80 | 67.60 | 135.20 | 202.80 |
| Sodium starch glycolate | 6.71% | 11.20 | 22.40 | 44.80 | 67.20 |
| Silica, colloidal anhydrous/colloidal silicon dioxide | 2.40% | 4.00 | 8.00 | 16.00 | 24.00 |
| Hypromellose | 4.79% | 8.00 | 16.00 | 32.00 | 48.00 |
| Purified water (removed during processing) | — | — | — | — | — |
| Total Intragranular Phase | 79.05% | 132.00 | 264.00 | 528.00 | 792.00 |
| Extragranular Phase | | | | | |
| Microcrystalline cellulose | 9.58% | 16.00 | 32.00 | 64.00 | 96.00 |
| Sodium starch glycolate | 4.79% | 8.00 | 16.00 | 32.00 | 48.00 |
| Silica, colloidal anhydrous/colloidal silicon dioxide | 0.48% | 0.80 | 1.60 | 3.20 | 4.80 |
| Sodium stearyl fumarate | 1.92% | 3.20 | 6.40 | 12.80 | 19.20 |
| Total Core Tablet Weight | 95.82% | 160.00 | 320.00 | 640.00 | 960.00 |
| Film Coating | | | | | |
| Coating premix, yellow | 2.47% | 4.13 | 6.49 | 10.03 | 13.57 |
| Coating premix, red | 0.75% | 1.26 | 1.98 | 3.06 | 4.14 |
| Coating premix, white | 0.75% | 1.26 | 1.98 | 3.06 | 4.14 |
| Coating premix, black | 0.21% | 0.35 | 0.55 | 0.85 | 1.15 |
| Purified water (removed during processing) | — | — | — | — | — |
| Total Film Coated Tablet Weight | 100.00% | 167.00 | 331.00 | 657.00 | 983.00 |

7.3. Example 3: Manufacturing Process

The manufacturing processes described herein may be reasonably adjusted by a person of skill in the art while maintaining the same production steps to compensate for different batch sizes and/or equipment characteristics.

7.3.1. Formulation A

FIG. 1 illustrates the manufacturing process for Formulation A. Compound 1, mannitol, hypromellose, crospovidone, and colloidal silicon dioxide were blended together in a high-shear mixer for 5 minutes to form a dry blend. Purified water was added by peristaltic pump to the dry blend over the course of about 5 to 8 minutes at room temperature using a high-shear granulator and the resulting mixture was kneaded for 4 to 8 minutes using the high-shear granulator, followed by wet milling using a 3.15 mm screen in a screening mill to form granules. The resulting granules were dried using a fluid bed dryer (at inlet temperature of about 60° C. for about fifteen minutes) to a final LOD (loss on drying) of <1.6%. The dried granules were passed through a 0.8 mm round screen.

Separately, microcrystalline cellulose, crospovidone, sodium stearyl fumarate, and colloidal silicon dioxide were combined to form a dry blend which was then passed through a 0.8 mm round screen. The resulting screened dry blend was added to a diffusion blender containing the dried granules comprising Compound 1. The dry blend and dried granules were blended to obtain a final blend. The dried final blend was then transferred to a Fette P1200i (TP09) tablet press and compressed to form tablet cores.

An aqueous film-coating suspension was made by dispersing several commercially available coating premixes in purified water. The compressed tablet cores were then coated with the film-coating suspension to produce the finished film-coated tablet.

7.3.2. Formulation B

Figure 2:
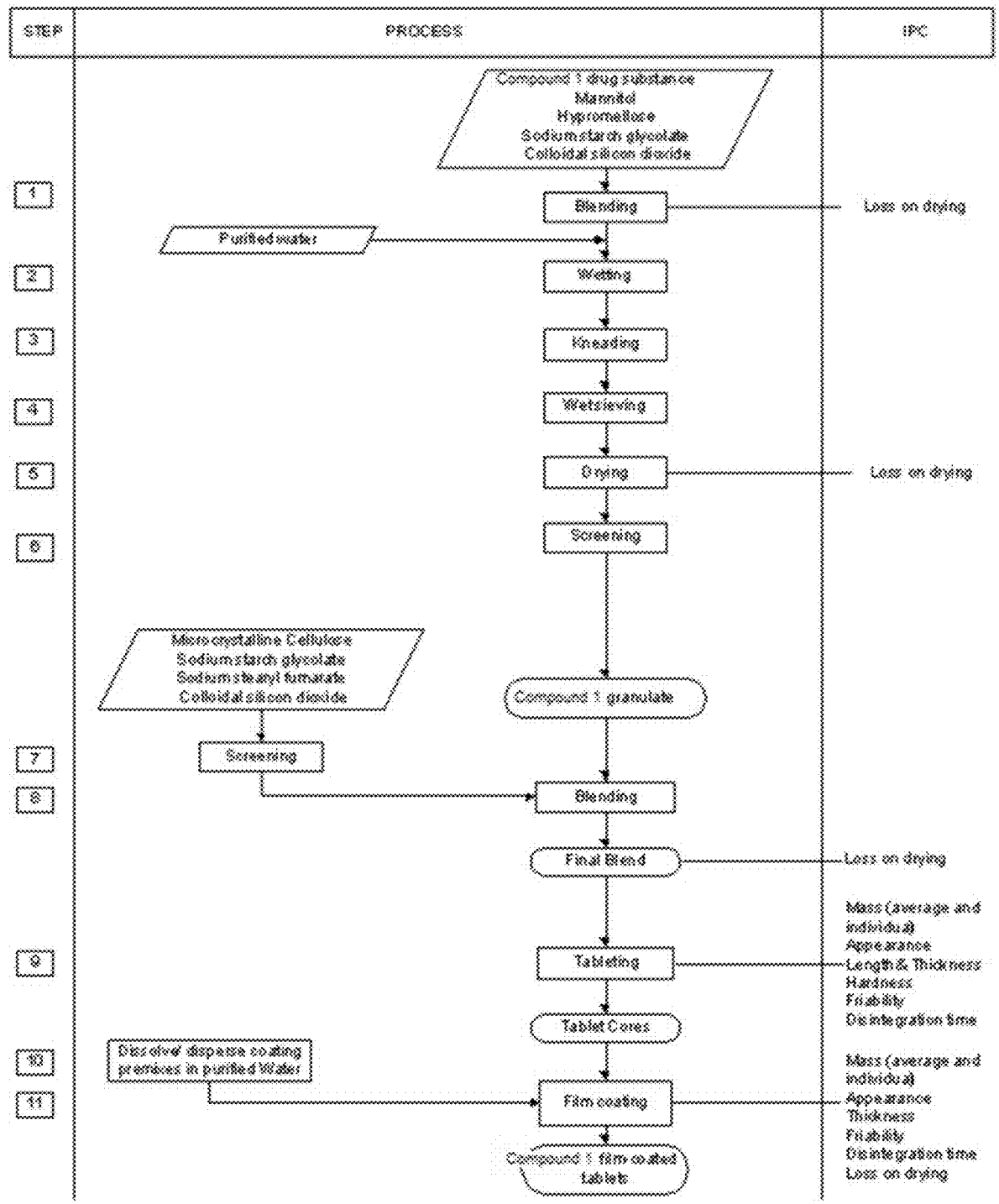
FIG. 2 provides an illustration of the manufacture for Formulation B.

FIG. 2 illustrates the manufacturing process for Formulation A. Compound 1, mannitol, hypromellose, sodium starch glycolate, and colloidal silicon dioxide were blended together in a high-shear mixer for 5 minutes to form a dry blend. Purified water was added by peristaltic pump to the dry blend of the course of about 5 to 8 minutes at room temperature using a high-shear granulator and the resulting mixture was kneaded in the high-shear granulator, followed by wet milling using a 3.15 mm screen in a screening mill to form granules. The resulting granules were dried using a fluid bed dryer to a final LOD (loss on drying) of <1.6%. The dried granules were passed through a 0.8 mm round screen.

Separately, microcrystalline cellulose, sodium starch glycolate, sodium stearyl fumarate, and colloidal silicon dioxide were combined to form a dry blend which was then passed through a 0.8 m round screen. The resulting screened dry blend was added to a diffusion blender containing the dried granules comprising Compound 1. The dry blend and dried granules were blended to obtain a final blend. The dried final blend was then transferred to a Fette P1200i (TP09) tablet press and compressed to form tablet cores.

An aqueous film-coating suspension was made by dispersing several commercially available coating premixes in purified water. The compressed tablet cores were then coated with the film-coating suspension to produce the finished film-coated tablet.

7.4. Example 4: Stability Studies

All technical batches of Compound 1 75 mg and 450 mg film-coated tablets for two clinical batches (Formulation A and Formulation B) demonstrated acceptable physical and chemical stability in HDPE bottles when stored up to 6 months at 5° C./ambient relative humidity (RH) and up to 9 months at 25° C./60% RH. No significant changes in chemical and physical properties were observed. Details on the stability tests are further detailed below.

7.4.1. Stability Studies

A bracketing design was applied to the stability studies of the film-coated tablets at all dosage strengths (i.e., 75 mg, 150 mg, 300 mg, 450 mg of Compound 1) for two clinical batches of Formulation A and Formulation B. The qualitative composition of the different dosage strengths was the same and dose proportional. The intermediate dosage strengths (i.e., 150 mg and 300 mg of Compound 1) of the film-coated tablets were bracketed by the 75 mg and 450 mg dosage strengths. Therefore, the shelf life for intermediate dosage strengths was assigned based on the stability studies of the 75 mg and 450 mg dosage strengths.

7.4.1.1. Shelf-Life and Storage Conditions

Shelf life was based on real-time data at the clinical storage condition. Real-time data must meet specifications and exhibit no trend toward an out of specification result before end of shelf life. Results of shelf-life and storage conditions are summarized in Table 5.

TABLE 5

Shelf-life and storage conditions for Compound 1 75 mg, 150 mg, 300 mg, and 450 mg film-coated tablets

|  | Clinical supplies Formulation A | Formulation B |
| --- | --- | --- |
| Shelf life | 18 months | 18 months |
| Packaging | HDPE bottles, induction seals, plastic CR closure | HDPE bottles, induction seals, plastic CR closure |
| Storage requirements | Store at 2-8° C. Do not freeze | Do not store above 25° C. Do not freeze |
| In-use period | 1 month | 1 month |
| In-use storage requirements | Store at 2-8° C. Do not freeze. | Do not store above 25° C. Do not freeze |

7.4.1.2. Routine Stability Tests

Two clinical batches of Compound 1 75 mg and 450 mg film-coated tablets (i.e., Formulation A Batch 1, Formulation B Batch 1, Formulation A Batch 2, and Formulation B Batch 2) demonstrated acceptable physical and chemical stability in HDPE bottles for up to six months at all storage conditions tested. No significant changes in chemical and physical properties were observed. Results of the routine stability tests are summarized in Tables 6 to 13.

TABLE 6

Chemical data: Compound 1 75 mg film-coated tablets, Formulation A Batch 1

|  |  |  | Degradation products | | |
| --- | --- | --- | --- | --- | --- |
| Storage conditions |  | Assay of active ingredient [%] | Max. individual unspecified [%] | Total [%] | Enantiomer [%] |
| Requirements |  | 90.0-110.0 | ≤0.5 | ≤2.0 | ≤0.5 |
| Initial analysis |  | 99.0 | <0.1 | <0.1 | 0.1 |
| −20° C./ambient RH | 6 months | 98.4 | <0.1 | <0.1 | <0.1 |
| 5° C./ambient RH | 1.5 months | 99.0 | <0.1 | <0.1 | 0.1 |
|  | 3 months | 98.6 | <0.1 | <0.1 | 0.1 |
|  | 6 months | 97.0 | <0.1 | <0.1 | <0.1 |

TABLE 6-continued

Chemical data: Compound 1 75 mg film-coated tablets, Formulation A Batch 1

| Storage conditions | | Assay of active ingredient [%] | Degradation products | | Enantiomer [%] |
|---|---|---|---|---|---|
| | | | Max. individual unspecified [%] | Total [%] | |
| 25° C./60% RH | 1.5 months | 98.6 | <0.1 | <0.1 | 0.1 |
| | 3 months | 98.3 | <0.1 | <0.1 | 0.1 |
| | 6 months | 98.5 | <0.1 | <0.1 | <0.1 |
| 40° C./75% RH | 1.5 months | 99.1 | <0.1 | <0.1 | 0.1 |
| | 3 months | 99.3 | <0.1 | <0.1 | 0.1 |
| | 6 months | 98.3 | <0.1 | <0.1 | <0.1 |
| 50° C./75% RH | 1 month | 99.6 | <0.1 | <0.1 | 0.1 |

TABLE 7

Physical data: Compound 1 75 mg film-coated tablets, Formulation A Batch 1

| Storage conditions Requirements | | Appearance * | Dissolution after 60 minutes [%] | | Water content [%] |
|---|---|---|---|---|---|
| | | | Average (n) Q = 70 | [min, max] | Report the results |
| Initial analysis | | ** | 96 (6) | [94, 101] | 2.5 |
| −20° C./ambient RH | 6 months | No change | 96 (6) | [94, 98] | 2.1 |
| 5° C./ambient RH | 1.5 months | No change | 95 (6) | [95, 97] | 2.1 |
| | 3 months | No change | 93 (6) | [92, 95] | 2.2 |
| | 6 months | No change | 98 (6) | [95, 100] | 2.2 |
| 25° C./60% RH | 1.5 months | No change | 96 (6) | [95, 98] | 2.1 |
| | 3 months | No change | 91 (6) | [98, 96] | 2.4 |
| | 6 months | No change | 96 (6) | [94, 98] | 2.3 |
| 40° C./75% RH | 1.5 months | No change | 91 (6) | [88, 94] | 2.4 |
| | 3 months | No change | 91 (6) | [88, 94] | 2.9 |
| | 6 months | *** | 90 (6) | [88, 95] | 2.6 |
| 50° C./75% RH | 1 month | No change | 89 (6) | [87, 91] | 2.4 |

*Round, biconvex, beveled edged, light brown to dark brown, film-coated tablet debossing 984 on one side and NVR on the other side.
**Round, biconvex, beveled edged, dark brown, film-coated tablet debossing 984 on one side and NVR on the other side.
***Round, biconvex, beveled edged, brown, film-coated tablet debossing 984 on one side and NVR on the other side.

TABLE 8

Chemical data: Compound 1 75 mg film-coated tablets, Formulation B Batch 1

| Storage conditions | | Assay of active ingredient [%] | Degradation products | | Enantiomer [%] |
|---|---|---|---|---|---|
| | | | Max. individual unspecified [%] | Total [%] | |
| Requirements | | 90.0-110.0 | ≤0.5 | ≤2.0 | ≤0.5 |
| Initial analysis | | 99.4 | <0.1 | <0.1 | <0.1 |
| −20° C./ambient RH | 6 months | 99.3 | <0.1 | <0.1 | <0.1 |
| 5° C./ambient RH | 6 months | 98.6 | <0.1 | <0.1 | <0.1 |
| 25° C./60% RH | 1.5 months | 99.2 | <0.1 | <0.1 | 0.1 |
| | 3 months | 100.4 | <0.1 | <0.1 | 0.1 |
| | 6 months | 99.6 | <0.1 | <0.1 | <0.1 |
| 30° C./75% RH | 1.5 months | 100.1 | <0.1 | <0.1 | 0.1 |
| | 3 months | 100.2 | <0.1 | <0.1 | 0.1 |
| | 6 months | 98.8 | <0.1 | <0.1 | <0.1 |
| 40° C./75% RH | 1.5 months | 99.8 | <0.1 | <0.1 | <0.1 |
| Initial analysis | | 99.4 | <0.1 | <0.1 | <0.1 |
| −20° C./ambient RH | 6 months | 99.3 | <0.1 | <0.1 | <0.1 |
| 5° C./ambient RH | 6 months | 98.6 | <0.1 | <0.1 | <0.1 |
| | 3 months | 100.1 | <0.1 | <0.1 | 0.1 |
| | 6 months | 98.6 | <0.1 | <0.1 | <0.1 |
| 50° C./75% RH | 1 month | 100.5 | <0.1 | <0.1 | 0.1 |

TABLE 9

Physical data: Compound 1 75 mg film-coated tablets, Formulation B Batch 1

| Storage conditions | | Appearance | Dissolution after 60 minutes [%] Average (n) | [min, max] | Water content [%] |
|---|---|---|---|---|---|
| Requirements | | * | Q = 70 | | Report the results |
| Initial analysis | | ** | 98 (6) | [97, 100] | 2.0 |
| −20° C./ambient RH | 6 months | No change | 98 (6) | [96, 100] | 1.7 |
| 5° C./ambient RH | 6 months | No change | 99 (6) | [98, 101] | 1.7 |
| 25° C./60% RH | 1.5 months | No change | 98 (6) | [97, 98] | 1.7 |
| | 3 months | No change | 96 (6) | [94, 97] | 1.9 |
| | 6 months | No change | 98 (6) | [97, 100] | 1.9 |
| 30° C./75% RH | 1.5 months | No change | 96 (6) | [94, 98] | 1.8 |
| | 3 months | No change | 94 (6) | [91, 95] | 2.1 |
| | 6 months | No change | 99 (6) | [98, 102] | 2.3 |
| 40° C./75% RH | 1.5 months | No change | 94 (6) | [94, 95] | 2.0 |
| | 3 months | No change | 94 (6) | [94, 95] | 2.7 |
| | 6 months | No change | 95 (6) | [94, 96] | 2.7 |
| 50° C./75% RH | 1 month | No change | 94 (6) | [92, 96] | 1.9 |

* Round, biconvex, beveled edged, light brown to dark brown, film-coated tablet debossing 984 on one side and NVR on the other side.
** Round, biconvex, beveled edged, dark brown, film-coated tablet debossing 984 on one side and NVR on the other side.

TABLE 10

Chemical data: Compound 1 450 mg film-coated tablets, Formulation A Batch 2

| Storage conditions | | Assay of active ingredient [%] | Degradation products Max individual unspecified [%] | Total [%] | Enantiomer Sum [%] |
|---|---|---|---|---|---|
| Requirements | | 90.0-110.0 | ≤0.5 | ≤2.0 | ≤0.5 |
| Initial analysis | | 98.5 | <0.1 | <0.1 | <0.1 |
| −20° C./ambient RH | 6 months | 97.1 | <0.1 | <0.1 | <0.1 |
| 5° C./ambient RH | 1.5 months | 98.9 | <0.1 | <0.1 | <0.1 |
| | 3 months | 99.8 | <0.1 | <0.1 | <0.1 |
| | 6 months | 97.6 | <0.1 | <0.1 | <0.1 |
| 25° C./60% RH | 1.5 months | 99.1 | <0.1 | <0.1 | 0.1 |
| | 3 months | 98.4 | <0.1 | <0.1 | <0.1 |
| | 6 months | 99.0 | <0.1 | <0.1 | <0.1 |
| 40° C./75% RH | 1.5 months | 99.2 | <0.1 | <0.1 | 0.1 |
| | 3 months | 98.8 | <0.1 | <0.1 | <0.1 |
| | 6 months | 97.3 | 0.1 | 0.1 | <0.1 |
| 50° C./75% RH | 1 month | 98.3 | <0.1 | <0.1 | 0.1 |

TABLE 11

Physical data: Compound 1 450 mg film-coated tablets, Formulation A Batch 2

| Storage conditions | | Appearance | Dissolution after 60 minutes [%] Average (n) | [min, max] | Water content [%] |
|---|---|---|---|---|---|
| Requirements | | * | Q = 70 | | Report the results |
| Initial analysis | | ** | 89 (6) | [87, 91] | 2.0 |
| −20° C./ambient RH | 6 months | No change | 87 (6) | [85, 88] | 1.8 |
| 5° C./ambient RH | 1.5 months | No change | 88 (6) | [86, 90] | 1.7 |
| | 3 months | No change | 85 (6) | [84, 87] | 1.9 |
| | 6 months | No change | 86 (6) | [84, 88] | 1.8 |
| 25° C./60% RH | 1.5 months | No change | 89 (6) | [87, 90] | 1.8 |
| | 3 months | No change | 84 (6) | [82, 86] | 1.9 |
| | 6 months | No change | 85 (6) | [84, 87] | 1.8 |
| 40° C./75% RH | 1.5 months | No change | 88 (6) | [85, 90] | 1.9 |
| | 3 months | No change | 84 (6) | [81, 85] | 2.1 |
| | 6 months | *** | 84 (6) | [83, 86] | 2.1 |

TABLE 11-continued

Physical data: Compound 1 450 mg film-coated tablets, Formulation A Batch 2

| Storage conditions | | Appearance | Dissolution after 60 minutes [%] | | Water content [%] |
|---|---|---|---|---|---|
| | | | Average (n) | [min, max] | |
| 50° C./75% RH | 1 month | No change | 81 (6) | [80, 82] | 2.1 |
| Initial analysis | | ** | 89 (6) | [87, 91] | 2.0 |
| −20° C./ambient RH | 6 months | No change | 87 (6) | [85, 88] | 1.8 |

\* Elongated, biconvex, beveled edged, light brown to dark brown, film coated tablet debossing 984 on one side and NVR on the other side.
\*\* Elongated, biconvex, beveled edged, dark brown, film coated tablet debossing 984 on one side and NVR on the other side.
\*\*\* Elongated, biconvex, beveled edged, brown, film coated tablet debossing 984 on one side and NVR on the other side.

TABLE 12

Chemical data: Compound 1 450 mg film-coated tablets, Formulation B Batch 2

| Storage conditions | | Assay of active ingredient [%] | Degradation products | | Enantiomer [%] |
|---|---|---|---|---|---|
| | | | Max individual unspecified [%] | Total [%] | |
| Requirements | | 90.0-110.0 | ≤0.5 | ≤2.0 | ≤0.5 |
| Initial analysis | | 101.1 | <0.1 | <0.1 | 0.1 |
| −20° C./ambient RH | 6 months | 99.1 | <0.1 | <0.1 | <0.1 |
| 5° C./ambient RH | 6 months | 98.6 | <0.1 | <0.1 | <0.1 |
| 25° C./60% RH | 1.5 months | 99.5 | <0.1 | <0.1 | 0.1 |
| | 3 months | 99.6 | <0.1 | <0.1 | <0.1 |
| | 6 months | 98.8 | <0.1 | <0.1 | <0.1 |
| 30° C./75% RH | 1.5 months | 100.8 | <0.1 | <0.1 | 0.1 |
| | 3 months | 100.2 | <0.1 | <0.1 | 0.1 |
| | 6 months | 98.3 | <0.1 | <0.1 | <0.1 |
| 40° C./75% RH | 1.5 months | 100.7 | <0.1 | <0.1 | 0.1 |
| | 3 months | 100.4 | <0.1 | <0.1 | 0.1 |
| | 6 months | 98.4 | <0.1 | <0.1 | <0.1 |
| 50° C./75% RH | 1 month | 96.5 | <0.1 | <0.1 | 0.1 |

TABLE 13

Physical data: Compound 1 450 mg film-coated tablets, Formulation B Batch 2

| Storage conditions | | Appearance | Dissolution after 60 minutes [%] | | Water content [%] |
|---|---|---|---|---|---|
| | | | Average (n) | [min, max] | |
| Requirements | | * | Q = 70 | | Report the results |
| Initial analysis | | ** | ** | 96 (6) | [95, 97] | 1.7 |
| −20° C./ambient RH | 6 months | No change | 95 (6) | [94, 95] | 1.3 |
| 5° C./ambient RH | 6 months | No change | 95 (6) | [94, 99] | 1.4 |
| 25° C./60% RH | 1.5 months | No change | 94 (6) | [93, 94] | 1.5 |
| | 3 months | No change | 94 (6) | [92, 95] | 1.6 |
| | 6 months | No change | 95 (6) | [94, 96] | 1.4 |
| 30° C./75% RH | 1.5 months | No change | 93 (6) | [91, 93] | 1.6 |
| | 3 months | No change | 92 (6) | [91, 93] | 1.6 |
| | 6 months | No change | 95 (6) | [93, 95] | 1.5 |
| 40° C./75% RH | 1.5 months | No change | 93 (6) | [92, 94] | 1.6 |
| | 3 months | No change | 91 (6) | [91, 92] | 1.7 |
| | 6 months | *** | 90 (6) | [89, 91] | 1.7 |
| 50° C./75% RH | 1 month | No change | 89 (6) | [88, 90] | 1.6 |

\* Elongated, biconvex, beveled edged, light brown to dark brown, film coated tablet debossing 984 on one side and NVR on the other side.
\*\* Elongated, biconvex, beveled edged, dark brown, film coated tablet debossing 984 on one side and NVR on the other side.
\*\*\* Elongated, biconvex, beveled edged, brown, film coated tablet debossing 984 on one side and NVR on the other side.

7.4.1.3. Photostability

Photostability testing was performed on two batches per dosage strength (i.e., 75 mg, 150 mg, 300 mg, 450 mg of Compound 1) according to the International Council for Harmonization of Technical Requirements for Registration of Pharmaceuticals for Human Use (ICH) guidelines for "Photostability testing of new active substances and medicinal products" (ICH Q1B). A sample protected from light and run in parallel to the exposed sample was tested for use as a control. Results of the photostability testing are summarized in Tables 14 and 15.

Light Source: ICH Option 1
Sample Load: ≥1.2 million lux hours
Integrated near UV-Energy: ≥200 watt hours per square meter There was no significant change in the appearance, assay, degradation products and dissolution rate between light exposed and unexposed samples for Compound 1 75 mg and 450 mg film-coated tablets. In addition, no significant uptake of water content is observed for light exposed samples, when compared to unexposed samples. Thus, exposure to light has no impact on the quality of film-coated tablets.

TABLE 14

Chemical data: photostability

| Strength Batch | Light exposure | Packaging | Assay of active ingredient [%] | Degradation products Any unspecified [%] | Total [%] | Enantiomer [%] |
|---|---|---|---|---|---|---|
| Requirements | | | 90.0-110.0 | ≤0.5 | ≤2.0 | ≤0.5 |
| 75 mg | 1.2 million luxh > 200 watt h/m2 | Dark control | 99.0 | <0.1 | <0.1 | 0.1 |
| Formulation A Batch 1 | | Unpacked | 99.5 | <0.1 | <0.1 | 0.1 |
| 75 mg | 1.2 million luxh > 200 watt h/m2 | Dark control | 99.4 | <0.1 | <0.1 | 0.1 |
| Formulation B Batch 1 | | Unpacked | 99.4 | <0.1 | <0.1 | 0.1 |
| 450 mg | 1.2 million luxh > 200 watt h/m2 | Dark control | 99.1 | <0.1 | <0.1 | 0.1 |
| Formulation A Batch 2 | | Unpacked | 99.3 | <0.1 | <0.1 | 0.1 |
| 450 mg | 1.2 million luxh > 200 watt h/m2 | Dark control | 100.6 | <0.1 | <0.1 | 0.1 |
| Formulation B Batch 2 | | Unpacked | 100.0 | <0.1 | <0.1 | 0.1 |

TABLE 15

Physical data: photostability

| Strength Batch | Light exposure | Packaging | Appearance | Dissolution after 60 minutes [%] Average (n) | [min, max] | Water content [%] |
|---|---|---|---|---|---|---|
| Requirements | | | * | Q = 70 | | Report the results |
| 75 mg | 1.2 million luxh > 200 watt h/m2 | Dark control | ** | 93 (6) | [90, 96] | 2.9 |
| Formulation A Batch 1 | | Unpacked | ** | 91 (6) | [84, 94] | 3.0 |
| 75 mg | 1.2 million luxh > 200 watt h/m2 | Dark control | ** | 97 (6) | [95, 98] | 2.7 |
| Formulation B Batch 1 | | Unpacked | ** | 96 (6) | [91, 99] | 2.6 |
| 450 mg | 1.2 million luxh > 200 watt h/m2 | Dark control | ** | 87 (6) | [84, 92] | 2.6 |

TABLE 15-continued

Physical data: photostability

| Strength Batch | Light exposure | Packaging | Appearance | Dissolution after 60 minutes [%] Average (n) | [min, max] | Water content [%] |
|---|---|---|---|---|---|---|
| Formulation A Batch 2 | | Unpacked | ** | 85 (6) | [76, 88] | 2.3 |
| 450 mg | 1.2 million luxh > 200 watt h/m2 | Dark control | ** | 94 (6) | [92, 96] | 2.2 |
| Formulation B Batch 2 | | Unpacked | ** | 93 (6) | [90, 94] | 2.1 |

* For 75 mg: Round, biconvex, beveled edged, light brown to dark brown, film-coated tablet debossing 984 on one side and NVR on the other side. For 450 mg: Elongated, biconvex, beveled edged, light brown to dark brown, film coated tablet debossing 984 on one side and NVR on the other side
** For 75 mg: Round, biconvex, beveled edged, dark brown, film-coated tablet debossing 984 on one side and NVR on the other side. For 450 mg: Elongated, biconvex, beveled edged, dark brown, film coated tablet debossing 984 on one side and NVR on the other side 7.4.1.4. Freeze and Thaw Cycle Test The freeze and thaw cycle testing was performed on two clinical batches each of 75 mg dosage strength (Formulation A Batch 1 and Formulation B Batch 1) and 450 mg dosage strength (Formulation A Batch 2 and Formulation B Batch 2) packaged in HDPE bottles. The stability samples were stored for four complete freeze and thaw cycles (−20° C./ambient RH for six days, followed by 25° C./60% RH for one day). Samples were taken after 28 days and the chemical and physical characteristics were analyzed.

Compound 1 75 mg and 450 mg film-coated tablets demonstrated acceptable physical and chemical stability in HDPE bottles. No significant changes in chemical and physical properties were observed. All results were within the specification limits. Results of the freeze and thaw cycle test are summarized in Tables 16 and 17.

TABLE 16

Chemical data: Freeze and thaw cycle test

| | | | Degradation products | | |
|---|---|---|---|---|---|
| Strength Batch Packaging | Storage conditions | Assay of active ingredient [%] | Max. individual unspecified [%] | Total [%] | Enantiomer [%] |
| Requirements 75 mg | | 90.0-110.0 | ≤0.5 | ≤2.0 | ≤0.5 |
| Formulation A Batch 1 | Initial analysis −20° C./Ambient RH/ 25° C./60% RH 28 days | 99.0 97.6 | <0.1 <0.1 | <0.1 <0.1 | 0.1 0.1 |
| Formulation B Batch 1 | Initial analysis −20° C./Ambient RH/ 25° C./60% RH 28 days | 99.4 97.7 | <0.1 <0.1 | <0.1 <0.1 | <0.1 0.1 |
| 450 mg | | | | | |
| Formulation A Batch 2 | Initial analysis −20° C./Ambient RH/ 25° C./60% RH 28 days | 98.5 98.6 | <0.1 <0.1 | <0.1 <0.1 | <0.1 0.1 |
| Formulation B Batch 2 | Initial analysis −20° C./Ambient RH/ 25° C./60% RH 28 days | 101.1 98.0 | <0.1 <0.1 | <0.1 <0.1 | 0.1 0.1 |

TABLE 17

Physical data: Freeze and thaw cycle test

| Strength Batch Packaging | Storage conditions | Appearance | Dissolution after 60 minutes [%] Average (n) | [min, max] | Water content [%] |
|---|---|---|---|---|---|
| Requirements 75 mg | | * | Q = 70 | | Not yet defined |
| Formulation A Batch 1 | Initial analysis −20° C./Ambient RH / 25° C./60% RH 28 days | ** No change | 96 (6) 97 (6) | [94, 101] [96, 99] | 2.5 2.2 |

TABLE 17-continued

Physical data: Freeze and thaw cycle test

| Strength Batch Packaging | Storage conditions | Appearance | Dissolution after 60 minutes [%] Average (n) | [min, max] | Water content [%] |
|---|---|---|---|---|---|
| Formulation B Batch 1 | Initial analysis | ** | 98 (6) | [97, 100] | 2.0 |
| | −20° C./Ambient RH / 25° C./60% RH 28 days | No change | 101 (6) | [98, 102] | 1.8 |
| 450 mg | | | | | |
| Formulation A Batch 2 | Initial analysis | ** | 89 (6) | [87, 91] | 2.0 |
| | −20° C./Ambient RH / 25° C./60% RH 28 days | No change | 85 (6) | [84, 87] | 1.8 |
| Formulation B Batch 2 | Initial analysis | ** | 96 (6) | [95, 97] | 1.7 |
| | −20° C./Ambient RH / 25° C./60% RH 28 days | No change | 93 (6) | [92, 93] | 1.6 |

\* 75 mg strength: Round, biconvex, beveled edged, light brown to dark brown, film-coated tablet debossing 984 on one side and NVR on the other side.
\* 450 mg strength: Elongated, biconvex, beveled edged, light brown to dark brown, film coated tablet debossing 984 on one side and NVR on the other side.
\*\* 75 mg strength: Round, biconvex, beveled edged, dark brown, film-coated tablet debossing 984 on one side and NVR on the other side.
\*\* 450 mg strength: Elongated, biconvex, beveled edged, dark brown, film coated tablet debossing 984 on one side and NVR on the other side.

7.4.1.5. Open Dish Study

The open dish study was performed on two clinical batches each of 75 mg dosage strength (Formulation A Batch 1 and Formulation B Batch 1), and 450 mg dosage strength (Formulation A Batch 2 and Formulation B Batch 2) stored in open HDPE bottles. The samples were stored at 25° C./60% RH for up to one month. Afterwards, the chemical and physical characteristics of the samples were analyzed.

Compound 1 75 mg and 450 mg film-coated tablets demonstrated acceptable physical and chemical stability in open HDPE bottles. No significant changes in chemical and physical properties were observed. All results were within the specification limits. Results of the open dish study are summarized in Tables 18 and 19.

TABLE 18

Chemical data: Open HDPE bottle

| Strength Batch Packaging | Storage conditions | Assay of active ingredient [%] | Degradation products Max. individual unspecified [%] | Total [%] | Enantiomer [%] |
|---|---|---|---|---|---|
| Requirements | | 90.0 - 110.0 | ≤0.5 | ≤2.0 | ≤0.5 |
| 75 mg | | | | | |
| Formulation A Batch 1 | Initial analysis | 99.0 | <0.1 | <0.1 | 0.1 |
| | 25° C./60% RH, Open - 1 month | 99.2 | <0.1 | <0.1 | 0.1 |
| Formulation B Batch 1 | Initial analysis | 99.4 | <0.1 | <0.1 | <0.1 |
| | 25° C./60% RH, Open - 1 month | 103.2 | <0.1 | <0.1 | 0.1 |
| 450 mg | | | | | |
| Formulation A Batch 2 | Initial analysis | 98.5 | <0.1 | <0.1 | <0.1 |
| | 25° C./60% RH, Open - 1 month | 99.0 | <0.1 | <0.1 | 0.1 |
| Formulation B Batch 2 | Initial analysis | 101.1 | <0.1 | <0.1 | 0.1 |
| | 25° C./60% RH, Open - 1 month | 98.9 | <0.1 | <0.1 | 0.1 |

TABLE 19

| | | | Dissolution after 60 minutes [%] | | Water |
|---|---|---|---|---|---|
| Strength Batch Packaging | Storage conditions | Appearance | Average (n) | [min, max] | content [%] |
| Requirements 75 mg | | * | Q = 70 | | Not yet defined |
| Formulation A Batch 1 | Initial analysis | ** | 96 (6) | [94, 101] | 2.5 |
| | 25° C./60% RH, Open - 1 month | No change | 96 (6) | [94, 99] | 2.6 |
| Formulation B Batch 1 | Initial analysis | ** | 98 (6) | [97, 100] | 2.0 |
| | 25° C./60% RH, Open -1 month | No change | 98 (6) | [94, 104] | 2.3 |
| 450 mg | | | | | |
| Formulation A Batch 2 | Initial analysis | ** | 89 (6) | [87, 91] | 2.0 |
| | 25° C./60% RH, Open - 1 month | No change | 82 (6) | [82, 83] | 2.9 |
| Formulation B Batch 2 | Initial analysis | ** | 96 (6) | [95, 97] | 1.7 |
| | 25° C./60% RH, Open - 1 month | No change | 90 (6) | [88, 91] | 2.7 |

*75 mg strength: Round, biconvex, beveled edged, light brown to dark brown, film-coated tablet debossing 984 on one side and NVR on the other side.
* 450 mg strength: Elongated, biconvex, beveled edged, light brown to dark brown, film coated tablet debossing 984 on one side and NVR on the other side.
** 75 mg strength: Round, biconvex, beveled edged, dark brown, film-coated tablet debossing 984 on one side and NVR on the other side.
** 450 mg strength: Elongated, biconvex, beveled edged, dark brown, film coated tablet debossing 984 on one side and NVR on the other side.

7.5. Example 5: Relative Bioavailability Study of Compound 1

7.5.1. Study Design

A randomized, open-label, four-period crossover study was conducted to evaluate (i) the relative bioavailability of Compound 1 using Formulation A and Formulation B oral tablet formulations (1×450 mg dose strength) as compared to the clinical service form (CSF) formulation (4×100 mg and 2×25 mg dose strength) under fasted conditions, and (ii) the effect of food on the relative bioavailability of Formulation A and Formulation B oral tablet formulations after a single dose of 450 mg of Compound 1 in healthy volunteers. Approximately thirty healthy male and female subjects of non-childbearing potential aged 18 to 55 years (inclusive) were included in this study.

Figure 7:
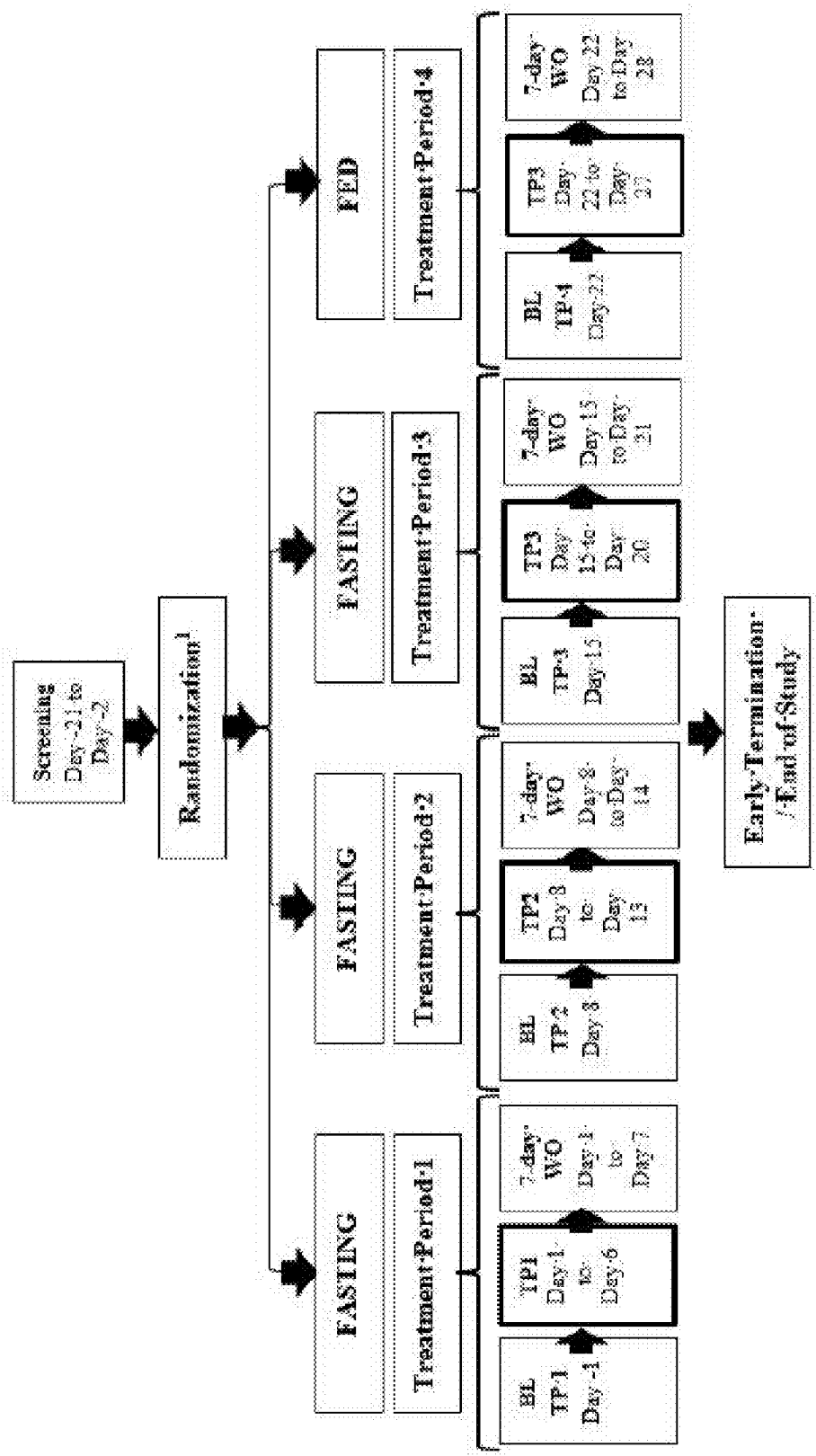
FIG. 7 provides an illustrative representation of the relative bioavailability study of Compound 1.
Figure 8:
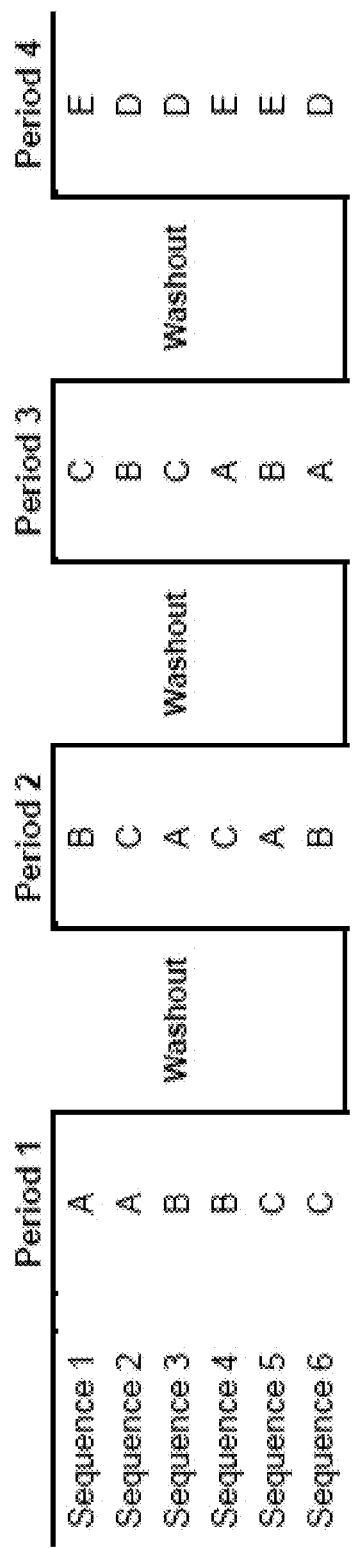
FIG. 8 provides an illustrative representation of the treatment sequences from the relative bioavailability study of Compound 1.

The single dose of Compound 1 followed by a sampling period expanding to 5 days post-dose was chosen to allow sufficient characterization of the pharmacokinetics (PK) parameters of the tested formulations (~5 elimination T1/2). The washout period, which included the time between treatment administration including the 5 days for PK sampling and the Baseline day prior to the next dose administration, ensured the complete elimination of Compound 1 from the body prior to the next treatment administration. This ensured that pre-dose was at least ≤5% of the Cmax (and below the lower limit of quantification [LLOQ]). The study design is depicted in FIG. 7. The study treatment sequences are depicted in FIG. 8. The study objectives and endpoints are summarized in Table 20.

The study was designed as a four-period five-treatment, six-sequence, single dose, crossover study in healthy volunteers and consisted of: a 28-day screening period; four baselines (one before each treatment period), and four treatment periods which comprise a single oral dose of 450 mg Compound 1 followed by 120 hours sequential PK sampling in each period. Treatment provided during the study include:

Treatment A: 450 mg (4×100 mg and 2×25 mg) Compound 1 CSF fasted (reference for bioavailability analysis)
Treatment B: 450 mg (1×450 mg) Compound 1 Formulation A fasted
Treatment C: 450 mg (1×450 mg) Compound 1 Formulation B fasted
Treatment D: 450 mg (1×450 mg) Compound 1 Formulation A fed
Treatment E: 450 mg (1×450 mg) Compound 1 Formulation B fed Treatments were administered with ~240 mL water. To compare the PK of Formulation A and Formulation B with the PK of the CSF formulation, treatments were administered under fasted conditions in the first three treatment periods. Fasting conditions referred to the administration of Compound 1 after at least ten hours of fasting the evening before, followed by a four hour post-dose fast.

To assess the potential food effect of a high-fat and high-calorie meal on the PK of Formulation A and Formulation B, dosing was conducted under fed conditions in period 4. Fed conditions referred to the subject consumed a standard FDA breakfast [high fat (~50 percent of total caloric content of the meal) and high calorie (~800 to 1000 calories) content] within 30 minutes, after at least ten hours of fasting the evening before. Compound 1 was dosed immediately after the end of the meal (±5 minutes). Subjects must have consumed at least 75% of the meal to be considered in the PK analysis set. For all treatments, water was only permitted until 1 hour before and again 1 hour after Compound 1 administration. The subjects remained domiciled at the study center for the duration of the study, including washout periods.

The planned dose for this study was 450 mg, which is the highest projected clinical dose in the further development of Compound 1 and the highest manufactured strength of Formulation A and Formulation B. The current study aimed to provide an understanding of the comparability in exposures of the previously used CSF capsule formulation (used in all prior clinical studies with Compound 1) to a new tablet Formulation A and Formulation B. Hence, the dose of 450 mg was proposed for the study as it is the most sensitive (highest) dose and strength.

All prescription medications, over the counter drugs, and significant non-drug therapies (including physical therapy and blood transfusions) administered or taken within the timeframe defined in the entry criteria prior to the start of the study and during the study were recorded on the concomitant medications/significant non-drug therapies section of the case report/record form (paper or electronic). The use of paracetamol/acetaminophen (up to 500 mg as a single dose and up to 2000 mg per day) was allowed for the treatment of minor adverse events (AEs) during this study. Except for medication which may have been required to treat AEs, no medication (including any vaccination or immunotherapy) other than study drug was allowed from the first dosing until all of the study completion evaluations were conducted.

If a subject had an incidental and limited need for a medication to be taken within the restricted pre-dose timeframe (e.g., ibuprofen for a headache, antibiotic prophylaxis prior to dental surgery, etc.), the Sponsor was to be advised, as administration of any concomitant medication could have required the subject to be withdrawn. Decisions regarding withdrawals and replacements were to be discussed with the Sponsor on a case-by-case basis.

1. Use of other investigational drugs at the time of enrollment, or within 5 half-lives of enrollment, or within 30 days, whichever was longer; or longer if required by local regulations.
2. A history of clinically significant ECG abnormalities, or any of the following ECG abnormalities at Screening and each Baseline:
   PR>200 msec
   QRS complex>120 msec
   QTcF>450 msec (males)
   QTcF>460 msec (females)
3. Known family history or known presence of long QT syndrome.
4. History of malignancy of any organ system (other than localized basal cell carcinoma of the skin or in situ cervical cancer), treated or untreated, within the past 5 years, regardless of whether there was evidence of local recurrence or metastases.
5. History of hypersensitivity to any of the study treatments or excipients or to drugs of similar chemical classes.
6. Significant illness which had not resolved within 2 weeks prior to initial dosing.
7. Any surgical or medical condition which could have significantly altered the absorption, distribution, metabolism, or excretion of drugs, or which could have jeopardized the subject, in case of participation in the study. The Investigator had to make this determination in consideration of

TABLE 20

| Objectives and Endpoints | |
| --- | --- |
| Primary objectives | Endpoints |
| To compare the rate and extent of drug absorption of a single oral dose of 450 mg of Compound 1 administered as Formulation A and Formulation B tablets (1 × 450 mg dose strength in reference to CSF formulation (4 × 100 mg and 2 × 25 mg dose strength) under fasted conditions in healthy subjects. To assess the potential for food effect on Formulation A and Formulation B after a single oral dose of 450 mg of Compound 1 in healthy subjects. | Primary - AUC(last), AUC(inf), and Cmax Secondary - Tmax, T1/2, CL/F, Vz/F, and Lambda _z |

7.5.2. Inclusion/Exclusion Criteria

Subjects eligible for inclusion in this study had to have met all of the following criteria:
1. Healthy male subjects and female subjects of non-childbearing potential, 18 to 55 years of age included, and in good health as determined by past medical history, physical examination, vital signs, ECG, and laboratory tests at Screening.
2. At Screening and First Baseline, vital signs (systolic and diastolic blood pressure [BP], and pulse rate) were assessed in the sitting position and again in the standing position. Sitting vital signs had to be within the following ranges:
   Oral body temperature of 35.0° C. to 37.5° C.
   Systolic BP of 90 to 139 mmHg
   Diastolic BP of 50 to 89 mmHg
   Pulse rate of 50 to ≤90 bpm
3. Subjects had to weigh at least 50 kg to participate in the study and had to have a body mass index (BMI) within the range of 18 to 30 kg/m2. BMI=Body weight (kg)/[Height (m)]2.

Subjects meeting any of the following criteria were not eligible for inclusion in this study:

the subject's medical history and/or clinical or laboratory evidence of any of the following:
   Inflammatory bowel disease, peptic ulcers, gastrointestinal including rectal bleeding
   Major gastrointestinal tract surgery such as gastrectomy, gastroenterostomy, or bowel resection
   Pancreatic injury or pancreatitis
   Liver disease or liver injury as indicated by abnormal liver function tests. alanine aminotransferase (ALT), aspartate aminotransferase (AST), gamma glutamyltransferase (GGT), alkaline phosphatase (ALP), and serum bilirubin were tested.
   Any single parameter of ALT, AST, GGT, ALP or serum bilirubin could not exceed 1.5× upper limit of normal (ULN).
   Any elevation above ULN of more than 1 parameter of ALT, AST, GGT, ALP, or serum bilirubin excluded a subject from participation in the study.
   History or presence of impaired renal function as indicated by clinically significantly abnormal creatinine or blood urea nitrogen (BUN) and/or urea values, or abnormal urinary constituents (e.g., albuminuria)

Evidence of urinary obstruction or difficulty in voiding at Screening

8. Recent (within the last 3 years) and/or recurrent history of autonomic dysfunction (e.g., recurrent episodes of fainting, palpitations, etc.).

9. Hemoglobin levels below 11.5 g/dL (females) and 12.0 mg/dL (males) at Screening and/or First Baseline.

10. Smokers (use of tobacco/nicotine products in the previous 3 months). Urine cotinine levels were measured during Screening and at First Baseline visit for all subjects. Smokers were defined as any subject who reported tobacco use and/or who had a urine cotinine≥200 ng/mL. In the case where a safety laboratory assessment at Screening and/or First Baseline was outside of the range specified in the exclusion criteria, the assessment was permitted to be repeated once, prior to randomization. If the repeat value remained outside of the specified ranges, the subject was to be excluded from the study.

7.5.3. Statistical Methods

Pharmacokinetic samples were obtained and evaluated in all subjects. Compound 1 was determined in plasma by a validated liquid chromatography with tandem mass spectrometry (LC-MS/MS) method. The PK parameters, presented below, were determined, whenever possible, using the actual recorded sampling times and non-compartmental method(s) with Phoenix WinNonlin (Version 8.0). The linear trapezoidal rule was used for AUC calculation. Regression analysis of the terminal plasma elimination phase for the determination of T1/2 included at least 3 data points after Cmax. If the adjusted R2 value of the regression analysis of the terminal phase was less than 0.75, no values were reported for Lambda Z, T1/2, Vz/F, CL/F, and AUCinf.

7.5.3.1. BA Assessment Under Fasted Conditions

Log transformed Compound 1 PK parameters (Cmax, AUClast, and AUCinf) were analyzed using a linear mixed effects model. The model considered the first 3 periods and it included sequence, period, and treatment as fixed factors and subjects nested within sequence as a random factor. Point estimates and 90% CIs for the ratios of the geometric means of the 2 test formulations treatment means vs. reference formulation were provided by back transformation to the original scale.

7.5.3.2. Food Effect

For each test formulation, log transformed Compound 1 PK parameters (Cmax, AUClast, and AUCinf) were analyzed using a linear mixed effects model. The model included treatment (fed vs. fasted) as fixed factors and subjects as a random factor. Point estimates and 90% CIs for the ratio of the geometric means (fed vs. fasted) were provided by back transformation to the original scale.

7.5.4. Study Results

A total of 30 subjects were enrolled, of which, 29 subjects completed in the study. One subject discontinued during Period 2 due to a mild adverse events of frequent bowel movements, abdominal pain and irregularity of bowel movement. All three events were resolved and considered as unrelated to study treatment. The subject's PK profile was completed in period 2.

Figure 9:
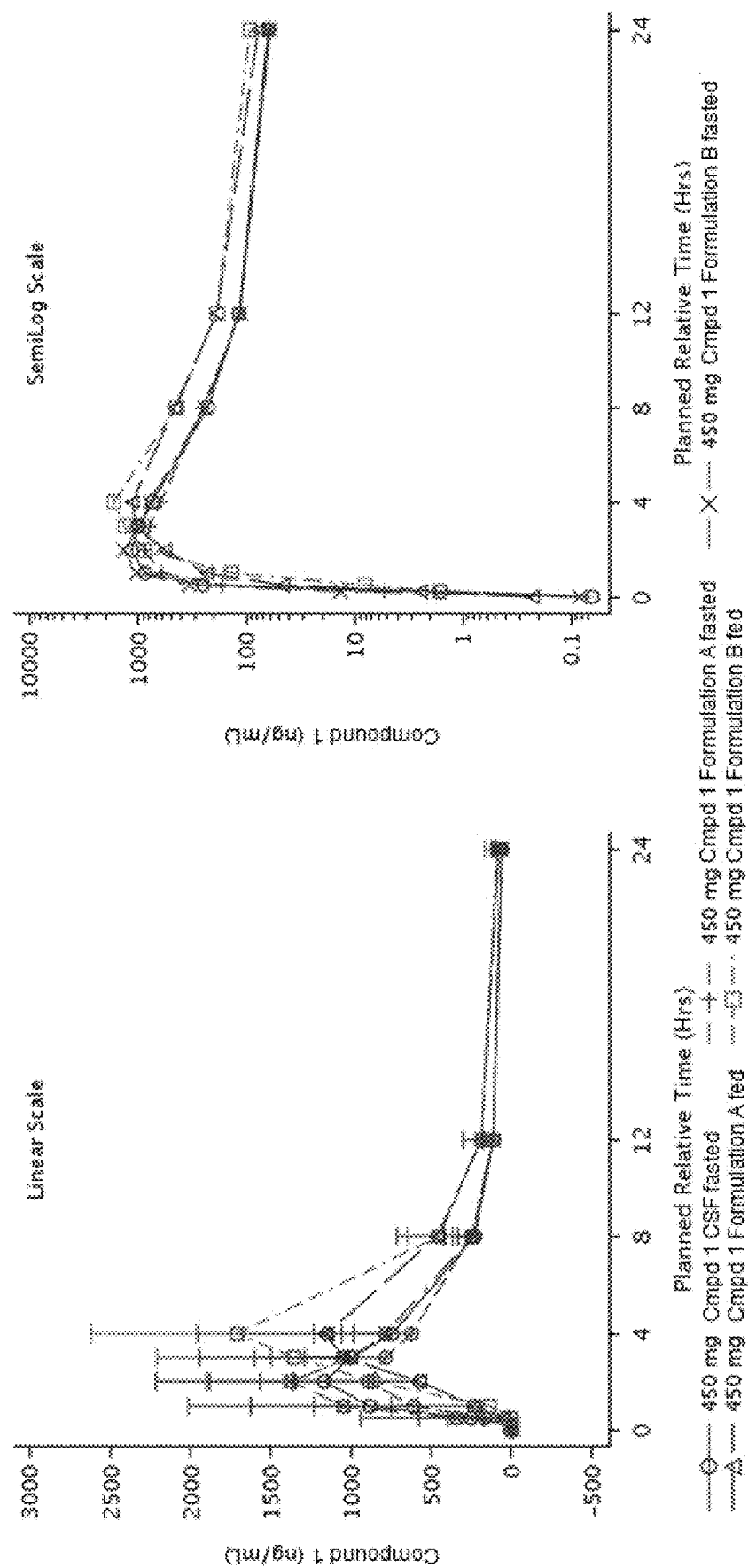
FIG. 9 provides the arithmetic mean plasma concentration-time profiles of Compound 1 from 0-120 hours post-dose.

Following administration of the single dose of 450 mg Compound 1 under fasted conditions, plasma concentrations of Compound 1 peaked rapidly and declined in a mono-exponential manner. Plasma concentrations of Compound 1 were below the limit of quantification by 120 hours, post dose for most subjects. Following administration of 450 mg Compound 1 under fed conditions, plasma concentrations of Compound 1 peaked slightly later compared to fasted conditions. Plasma concentrations of Compound 1 were below the limit of quantification by 120 hours, post dose, for most subjects under fed conditions. Mean plasma concentration-time profiles of Compound 1 after all treatments of Compound 1 were similar during the elimination phase, but peak plasma concentrations of Compound 1 Formulation B under fed conditions appeared higher. The mean plasma concentration-time profiles of Compound 1 from 0-120 hours post-dose are presented in text in FIG. 9.

The PK of Compound 1, following the administration of Compound 1 as the CSF capsule, Formulation A, and Formulation B, under fasted conditions, were compared. Median (min–max) Tmax values were 2.0 hours (0.50 hour-8.00 hours) for Compound 1 CSF and Formulation A and Formulation B. Arithmetic mean Compound 1 Cmax, AUClast, and AUCinf values were comparable for the CSF and Formulation B formulations; whereas, Formulation A values were slightly lower by comparison. Arithmetic mean CL/F and Vz/F values were also comparable for the CSF and Formulation B, with higher values observed for the Formulation A. Arithmetic mean t1/2 of Compound 1 was approximately 16 hours following all fasted treatments. Individual plasma PK parameters for Compound 1 are presented in Table 21.

TABLE 21

Summary statistics of Compound 1 PK parameters (PK analysis set).

| Treatment | Statistics | Cmax (ng/mL) | Tmax (h) | AUClast (ng*h/mL) | AUCinf (ng*h/mL) |
| --- | --- | --- | --- | --- | --- |
| 450 mg Compound 1/ CSF fasted (A)/ (N = 30) | n | 30 | 30 | 30 | 29 |
| | Mean (SD) | 1370 (680) | | 8210 (3650) | 8340 (3700) |
| | CV % mean | 49.7 | | 44.4 | 44.3 |
| | Geo-mean | 1210 | | 7430 | 7550 |
| | CV % geo-mean | 55.1 | | 49.3 | 49.7 |
| | Median | 1220 | 2 | 7740 | 7890 |
| | [Min; Max] | [320; 3240] | [1.00; 4.00] | [2430; 16000] | [2470; 16000] |
| 450 mg Compound 1/ Formulation A fasted (B)/ (N = 29) | n | 29 | 29 | 29 | 29 |
| | Mean (SD) | 1130 (641) | | 7260 (3650) | 7300 (3670) |
| | CV % mean | 56.5 | | 50.3 | 50.2 |
| | Geo-mean | 955 | | 6460 | 6510 |
| | CV % geo-mean | 70.4 | | 53.2 | 52.9 |
| | Median | 1000 | 2 | 6420 | 6440 |
| | [Min; Max] | [210; 2830] | [1.00; 8.00] | [1870; 17900] | [1900; 18000] |

TABLE 21-continued

Summary statistics of Compound 1 PK parameters (PK analysis set).

| | | | | | |
|---|---|---|---|---|---|
| 450 mg | n | 30 | 30 | 30 | 30 |
| Compound 1/ | Mean (SD) | 1630 (829) | | 8720 (3810) | 8760 (3820) |
| Formulation B | CV % mean | 51 | | 43.7 | 43.6 |
| fasted (C)/ | Geo-mean | 1400 | | 7870 | 7920 |
| (N = 30) | CV % geo-mean | 68 | | 50.9 | 50.6 |
| | Median | 1430 | 2 | 8190 | 8230 |
| | [Min; Max] | [161; 3250] | [0.50; 4.02] | [1960; 15800] | [1990; 15900] |
| 450 mg | n | 15 | 15 | 15 | 13 |
| Compound 1/ | Mean (SD) | 1530 (810) | | 10300 (4220) | 10400 (4570) |
| Formulation A/ | CV % mean | 52.9 | | 40.8 | 44.1 |
| fed (D) | Geo-mean | 1300 | | 9510 | 9410 |
| (N = 15) | CV % geo-mean | 68.7 | | 46 | 49.4 |
| | Median | 1440 | 3.82 | 10000 | 10100 |
| | [Min; Max] | [454; 2850] | [1.00; 8.10] | [3840; 19800] | [3870; 20000] |
| 450 mg | n | 14 | 14 | 14 | 14 |
| Compound 1/ | Mean (SD) | 1950 (1010) | | 12200 (5450) | 12300 (5470) |
| Formulation B | CV % mean | 51.9 | | 44.5 | 44.4 |
| fed (E) | Geo-mean | 1710 | | 11300 | 11400 |
| (N = 14) | CV % geo-mean | 61.6 | | 41.4 | 41.4 |
| | Median | 1870 | 3.83 | 11400 | 11500 |
| | [Min; Max] | [487; 4400] | [1.98; 3.95] | [6030; 27300] | [6060; 27400] |

| Treatment | $T_{1/2}$ (h) | Lambda z (1/h) | CL/F (L/h) | Vz/F (L) |
|---|---|---|---|---|
| 450 mg | 29 | 29 | 29 | 29 |
| Compound 1/ | 15.7 (4.84) | 0.0497 (0.0205) | 66.8 (35.4) | 1530 (976) |
| CSF fasted (A)/ | 30.8 | 41.2 | 53 | 63.6 |
| (N = 30) | 14.9 | 0.0465 | 59.7 | 1280 |
| | 36.5 | 36.5 | 49.6 | 67.7 |
| | 15.9 | 0.0437 | 57 | 1290 |
| | [6.09; 23.3] | [0.0297; 0.114] | [28.1; 182] | [395; 4360] |
| 450 mg | 29 | 29 | 29 | 29 |
| Compound 1/ | 15.5 (4.12) | 0.0490 (0.0198) | 78.4 (45.2) | 1770 (1100) |
| Formulation A | 26.5 | 40.4 | 57.7 | 61.8 |
| fasted (B)/ | 14.9 | 0.0465 | 69.2 | 1490 |
| (N = 29) | 31.4 | 31.3 | 53 | 68 |
| | 15.6 | 0.0444 | 69.8 | 1480 |
| | [5.04; 24.5] | [0.0283; 0.137] | [25.0; 237] | [409; 4830] |
| 450 mg | 30 | 30 | 30 | 30 |
| Compound 1/ | 15.5 (4.90) | 0.0499 (0.0188) | 64.1 (37.9) | 1480 (1130) |
| Formulation B | 31.5 | 37.7 | 59.1 | 76.3 |
| fasted (C)/ | 14.7 | 0.047 | 56.8 | 1210 |
| (N = 30) | 35.1 | 35.1 | 50.6 | 69 |
| | 15.1 | 0.046 | 54.8 | 1170 |
| | [6.97; 27.6] | [0.0251; 0.0994] | [28.3; 226] | [357; 6260] |
| 450 mg | 13 | 13 | 13 | 13 |
| Compound 1/ | 17.1 (5.39) | 0.0467 (0.0243) | 53.0 (26.5) | 1340 (867) |
| Formulation A/ | 31.4 | 52.1 | 49.9 | 64.6 |
| fed (D) | 16.1 | 0.0429 | 47.8 | 1120 |
| (N = 15) | 40.7 | 40.8 | 49.4 | 71.6 |
| | 17.6 | 0.0394 | 44.6 | 1120 |
| | [5.79; 25.8] | [0.0269; 0.120] | [22.5; 116] | [356; 3530] |
| 450 mg | 14 | 14 | 14 | 14 |
| Compound 1/ | 15.2 (2.85) | 0.0477 (0.0112) | 42.4 (15.8) | 912 (348) |
| Formulation B | 18.8 | 23.5 | 37.4 | 38.2 |
| fed (E) | 14.9 | 0.0466 | 39.5 | 848 |
| (N = 14) | 21.3 | 21.2 | 41.4 | 41.9 |
| | 16.1 | 0.0432 | 39.5 | 836 |
| | [9.31; 18.8] | [0.0368; 0.0744] | [16.4; 74.3] | [395; 1510] |

Formulation A and Formulation B had similar PK exposure (mean peak plasma concentrations (Cmax) and total exposures (AUC(last) and AUC(inf)) to the CSF formulation, as summarized in Table 22. Under the fasted condition and after a single 450 mg dose of Compound 1, the Cmax and AUCs (AUC(last) and AUC(inf)) of Formulation A were 20% and 12 lower than those of the CSF formulation, respectively, relative to the fed state. The Cmax and AUCs (AUC(last) and AUC(inf)) of Formulation B were 15% and 6% higher than those of the CSF formulation, respectively, relative to the fed state.

TABLE 22

Statistical analysis of relative bioavailability of Compound 1 under fasted conditions.

| PK Parameter (unit) | Treatment (450 mg Compound 1) | n* | Adjusted geo-mean (90% CI) | Comparison | Geo-mean ratio | SE | (90% CI) |
|---|---|---|---|---|---|---|---|
| Cmax (ng/mL) | CSF fasted (A) | 30 | 1210 (1000, 1470) | | | | |
| | Formulation A fasted (B) | 29 | 971 (798, 1180) | B vs A | 0.80 | 1.10 | (0.68, 0.94) |
| | Formulation B fasted (C) | 30 | 1400 (1150, 1700) | C vs A | 1.15 | 1.10 | (0.98, 1.36) |
| AUC(last) (ng*h/mL) | CSF fasted (A) | 30 | 7430 (6330, 8720) | | | | |
| | Formulation A fasted (B) | 29 | 6510 (5550, 7640) | B vs A | 0.88 | 1.07 | (0.79, 0.98) |
| | Formulation B fasted (C) | 30 | 7870 (6710, 9230) | C vs A | 1.06 | 1.07 | (0.95, 1.18) |
| AUC(inf) (ng*h/mL) | CSF fasted (A) | 29 | 7460 (6360, 8760) | | | | |
| | Formulation A fasted (B) | 29 | 6560 (5580, 7690) | B vs A | 0.88 | 1.07 | (0.79, 0.98) |
| | Formulation B fasted (C) | 30 | 7920 (6750, 9280) | C vs A | 1.06 | 1.07 | (0.95, 1.18) | n* = number of subjects with non-missing values,
CI—Confidence Interval,
SE—Standard Error.
Model: The log transformed PK parameters were analyzed using an analysis of variance (ANOVA) model with treatment, period, sequence as fixed effect and subject nested within sequence as random effect.
Only data collected under fasted conditions (first 3 periods) were included.

Intake of a high-fat meal had a moderate increase in PK exposure (mean peak plasma concentrations (Cmax) and total exposures (AUC(last) and AUC(inf)) of Formulation A and Formulation B, as summarized in Table 23. The ratios of the geometric means for Cmax, AUClast, and AUCinf of Compound 1 Formulation A fed versus fasted suggest that administration with food increases peak and total exposures of Compound 1. The ratio of the geometric means for Cmax, AUClast, and AUCinf of Compound 1 Formulation B 2 fed versus fasted suggest that administration with food increases peak and total exposures of Compound 1. Under the fed condition with a high fat meal, the Cmax, AUC(last), and AUC(inf) of a single 450 mg dose of Compound 1, Formulation A increased by 34%, 43, and 38%, respectively, relative to the fasted state. Similarly, the Cmax, AUC(last), and AUC(inf) of Formulation B increased by 26%, 49%, and 49%, respectively, relative to the fasted state.

TABLE 23

Statistical analysis to assess food effect (fed v. fasted) on plasma PK parameters of Compound 1.

| PK Parameter (unit) | Treatment (450 mg Compound 1) | n* | Adjusted geo-mean (90% CI) | Comparison (Fed vs Fast) | Geo-mean ratio | SE | (90% CI) |
|---|---|---|---|---|---|---|---|
| Cmax (ng/mL) | Formulation A fasted (B) | 29 | 967 (806, 1160) | | | | |
| | Formulation A fed (D) | 15 | 1300 (1020, 1650) | D vs B | 1.34 | 1.16 | (1.04, 1.73) |
| | Formulation B fasted (C) | 30 | 1400 (1170, 1670) | | | | |
| | Formulation B fed (E) | 14 | 1760 (1380, 2250) | E vs C | 1.26 | 1.17 | (0.98, 1.63) |
| AUC(last) (ng*h/mL) | Formulation A fasted (B) | 29 | 6500 (5630, 7500) | | | | |
| | Formulation A fed (D) | 15 | 9290 (7830, 11000) | D vs B | 1.43 | 1.10 | (1.23, 1.67) |
| | Formulation B fasted (C) | 30 | 7870 (6830, 9080) | | | | |
| | Formulation B fed (E) | 14 | 11700 (9870, 14000) | E vs C | 1.49 | 1.10 | (1.27, 1.75) |
| AUC(inf) (ng*h/mL) | Formulation A fasted (B) | 29 | 6540 (5670, 7550) | | | | |
| | Formulation A fed (D) | 13 | 9030 (7550, 10800) | D vs B | 1.38 | 1.10 | (1.17, 1.62) |

TABLE 23-continued

Statistical analysis to assess food effect (fed v. fasted) on plasma PK parameters of Compound 1.

| PK Parameter (unit) | Treatment (450 mg Compound 1) | n* | Adjusted geo-mean (90% CI) | Comparison (Fed vs Fast) | Geo-mean ratio | SE | (90% CI) |
|---|---|---|---|---|---|---|---|
| | Formulation B fasted (C) | 30 | 7920 (6870, 9130) | | | | |
| | Formulation B fed (E) | 14 | 11800 (9920, 14100) | E vs C | 1.49 | 1.10 | (1.27, 1.74) | n* = number of subjects with non-missing values,
CI—Confidence Interval,
SE—Standard Error.
Model: The log transformed PK parameters were analyzed using an analysis of variance (ANOVA) model with treatment as fixed effect and subject as random effect.
Data coming from all the 4 periods were included.

Taken together, these results indicated that Compound 1 has a positive food effect.

7.6. Example 6: Absorption, Distribution, Metabolism and Excretion Study of Compound 1

7.6.1. Study Design

A single-center, open-label study was conducted to evaluate the absorption, distribution, metabolism, and excretion (ADME) and PK of Compound 1 following a single oral dose of [14C]Compound 1 in healthy male subjects at steady state conditions. Six healthy male subjects of aged 18 to 55 years (inclusive) were included in this study.

The study consisted of a 28-day screening period (including baseline period of 1 day) and 12 days of treatment period. The study design is depicted in FIG. 10.

The treatment period comprised of the following: non-radiolabeled Compound 1 (Cmpd 1) 400 mg (b.i.d.) administration for 4 days (Day 1-Day 4), followed by a single oral dose of 400 mg [14C]Compound 1 3.7 MBq (100 µCi) in the morning (AM dose) of Day 5 and a single oral dose of non-radiolabeled Compound 1 400 mg in the evening (PM dose) of Day 5. A dosing regimen of 400 mg (b.i.d.) of non-radiolabeled Compound 1 was resumed in the morning of Day 6 and continued until Day 12 evening (PM dose) thereafter (Day 6-Day 12). All treatment administrations (Day 1 to Day 12) occurred approximately 30 minutes following consumption of a standardized meal. Treatments were administered with ~240 mL water as 4×100 mg hard gelatin capsules. The radioactive release criteria was met and all the subjects were released from the study site on Day 14 afternoon. The study objectives and endpoints are summarized in Table 24.

The PK blood sample collection schedule was appropriate to characterize the PK of Compound 1 and any circulating major metabolites. The urine and feces collection schedule was set up adequately to ensure complete excretion of radioactivity. Due to the non-linear PK of Compound 1, the study was conducted at steady state.

A dose of 400 mg was expected to provide sufficiently high drug and metabolite levels to meet the study objectives and was supported by the available safety and tolerability of Compound 1 at this dose (see Example 5). The planned single oral dose of 400 mg of [14C]Compound 1 was expected to allow successful characterization of the ADME properties of Compound 1 in humans.

Subjects who met the eligibility criteria were admitted to the study site approximately 24 hours prior to dosing for baseline evaluations. The observation and sample collection period (blood, urine and feces) and safety assessments were made for up to 216 hours after the [$^{14}$C]Compound 1 administration. Safety assessments included physical examinations, electrocardiograms (ECGs), vital signs, standard clinical laboratory evaluations (hematology, blood chemistry, and urinalysis), AE and serious adverse event (SAE) monitoring.

Except for medications, which were required to treat adverse events, no medications other than study treatment were allowed from dose administration until all of the study completion evaluations were conducted.

TABLE 24

Objectives and Endpoints

| Primary objectives | Endpoints |
|---|---|
| To determine the rates and routes of excretion of [14C] Compound 1 related radioactivity, including mass balance of total drug-related radioactivity in urine and feces following a single 400 mg oral dose of [14C] Compound 1 at steady state in healthy subjects. To determine the pharmacokinetics of total radioactivity in blood and plasma. To characterize the plasma pharmacokinetics of Compound 1 and known key metabolites, if applicable, | Excretion/mass balance of [14C]-radioactivity recovered in excreta (urine, feces) as percentage (%) of the administered dose Cmax, Tmax, AUC, T1/2 and any other PK parameters as appropriate from the concentration vs. time data of [14C]-radioactivity (whole blood, plasma) Cmax, Tmax, AUClast, AUCtau, CLss/F, Vz/F and any other PK parameters under steady state conditions as appropriate from the concentration vs. time profiles of Compound 1 and known metabolites, if applicable |

TABLE 24-continued

| Objectives and Endpoints | |
|---|---|
| Secondary objective | Endpoints |
| To assess the safety and tolerability of multiple oral doses of 400 mg of Compound 1 administered to healthy male subjects. | Frequency and severity of adverse events including changes in laboratory values, vital signs and ECGs |

7.6.2. Inclusion/Exclusion Criteria

Subjects eligible for inclusion in this study had to have met all of the following criteria:

1. Healthy male subjects 18 to 55 years of age included, and in good health as determined by past medical history, physical examination, vital signs, ECG, and laboratory tests at screening.
2. At screening and first baseline, vital signs (after 3 minutes in the supine position) were assessed in the supine position within the following normal ranges:
   Oral body temperature of 35.0° C. to 37.5° C.
   Systolic BP of 90 to 139 mmHg
   Diastolic BP of 50 to 89 mmHg
   Pulse rate of 45 to ≤90 bpm
3. Subjects had to have a body mass index (BMI) within the range of 18 to 30 kg/m$^2$. BMI=Body weight (kg)/[Height (m)]$^2$, with body weight greater than or equal to 55 kg and no more than 120 kg to participate in the study.

Subjects meeting any of the following criteria were not eligible for inclusion in this study:

1. Exposure to radiation at a level of 0.1-1.0 mSv over the past year, also if exposed to 1.1-2.0 mSv over the past 2 years, 2.1-3.0 mSv over the past 3 years, etc. (due to systemic administration of radioactive substances, or to external irradiation for diagnostic, therapeutic, job-related, or research purposes). Radioactivity in blood/plasma and available excreta above background.
2. Use of other investigational drugs within 5 half-lives, or within 6 months (in case of therapeutics with expected long half-lives), or within 30 days after dosing (for small molecule drugs with daily dosing scheme), or longer if required by local regulations. Investigator was expected to apply the appropriate due diligence to ensure sufficient washout times to avoid a carry-over of PK or PD or any impact on subject safety by the other investigational drugs.
3. Evidence of any remaining PD effects not having yet returned to baseline after previous exposure to an investigational drug.
4. Significant illness not resolved within two weeks prior to initial dosing.
5. Recent (within the last three years) and/or recurrent history of autonomic dysfunction (e.g., recurrent episodes of fainting, palpitations, etc.).
6. History of multiple and recurring allergies or allergy to the investigational compound/compound class used in this study.
7. History of immunodeficiency diseases, or a positive HIV (ELISA and Western blot) test result.
8. History or presence of clinically significant ECG abnormalities and EC intervals:
   PR-interval of 200 msec or greater
   Resting QTcF≥450 msec
   QRS-complex≥120 msec
9. Any surgical or medical condition significantly altering the ADME of drugs, at Investigator's discretion considering the subject's medical history and/or clinical or laboratory evidence of any of the following:
   Inflammatory bowel disease, peptic ulcers, gastrointestinal including rectal bleeding
   Major gastrointestinal tract surgery such as gastrectomy, gastroenterostomy, or bowel resection
   Pancreatic injury or pancreatitis
   Liver disease or liver injury as indicated by abnormal liver function tests—alanine aminotransferase (ALT), aspartate aminotransferase (AST), gamma glutamyltransferase (GGT), alkaline phosphatase (ALP), and serum bilirubin.
   Any single parameter of ALT, AST, GGT, ALP or serum bilirubin exceeding 1.5× upper limit of normal (ULN).
   Any elevation above ULN of more than one parameter of ALT, AST, GGT, ALP, or serum bilirubin.
   History or presence of impaired renal function as indicated by clinically significantly abnormal creatinine or blood urea nitrogen (BUN) and/or urea values, or abnormal urinary constituents (e.g., albuminuria)
   Evidence of urinary obstruction or difficulty in voiding at screening
   MDRD-based estimated glomerular filtration rate (eGFR) <80 mL/min
10. Absence of regular defecation pattern (subjects with a mean defecation frequency of less than once per day or chronic diarrhea).
11. Consumption of Seville oranges, grapefruit, grapefruit hybrids, pummelos, star fruit, pomegranate and exotic citrus fruits (as well as their juices) and cruciferous vegetables (Brussels sprouts, broccoli, cabbage, cauliflower) during the last 7 days prior to dosing.
12. Chronic infection with Hepatitis B (HBV) or Hepatitis C (HCV). A positive HBV surface antigen (HBsAg) test, or if standard local practice, a positive HBV core antigen test. Subjects with a positive HCV antibody test had HCV RNA levels measured. Subjects with positive HCV RNA were excluded.
13. History of drug abuse or unhealthy alcohol use within the 12 months prior to dosing, or evidence of such abuse as indicated by the laboratory assays conducted during screening and baseline.
14. History of recreational cannabis use within four weeks prior to dosing, or evidence of such use as indicated by the laboratory assays conducted during screening and baseline.
15. Use of any prescription drugs, herbal supplements, prescribed medicinal use of cannabis/marijuana, within four weeks prior to initial dosing, and/or over-the-counter (OTC) medication, dietary supplements (vitamins included) within two weeks prior to initial dosing.
16. Donation or loss of 400 mL or more of blood within 2 months prior to initial dosing or donation or loss of 200 mL or more of blood within 1 month prior to initial dosing or donation of component blood within 2 weeks prior to initial dosing.
17. Smokers (use of tobacco/nicotine products in the previous 3 months). Urine cotinine levels of ≥500 ng/mL measured at screening and baseline.
18. History of significant skin rash related to drug exposure or significant drug allergy that required chronic medication including steroids, history of atopic allergy (i.e. asthma, urticaria, eczematous dermatitis).

19. Hemoglobin levels below 13.4 g/dL at baseline.
20. Sexually active males unwilling to use a condom during intercourse while taking investigational drug and for 12 weeks after stopping investigational drug.
21. Participation in strenuous physical exercise (e.g. weight training, aerobics, football) for 4 days prior to dosing until study completion.

7.6.3. Determination of Total Radioactivity

Blood, plasma, urine, and feces samples were obtained and evaluated in all subjects. Total concentration of Compound 1 and metabolites was determined by [14C] concentrations in whole blood and plasma by a validated liquid scintillation counting (LSC) method and combustion analyses. If the co-efficient of variation of replicate radioactivity measurements was >20%, the sample was re-homogenized and/or reanalyzed.

Multiple-dose PK parameters (Cmax, Tmax, AUClast, Vz/F, CLss/F, under steady state conditions), presented below, for Compound 1 and metabolites were derived from plasma concentration versus sampling time data.

Single-dose blood and plasma PK parameters (Cmax, Tmax, AUClast and AUCinf), for total radioactivity were derived from plasma and blood concentration versus sampling time data. PK parameters were determined using non-compartmental method(s) with Phoenix WinNonLin (Version 6.4) for total radioactivity.

[14C]-radioactivity data, which was based on LSC analyses, for excreta was used to calculate percentage of dose excreted via urine or feces as well as a total percent of dose recovered.

Profiles of radioactive metabolites in urine and feces pools representing more than 90% of total radioactivity in the collected excreta of individual subjects were specified as dose proportion (%) per metabolite.

7.6.3.1. Radiolabeled [14C]Compound 1

Radiolabeled [14C]Compound 1 has the following structural formula:

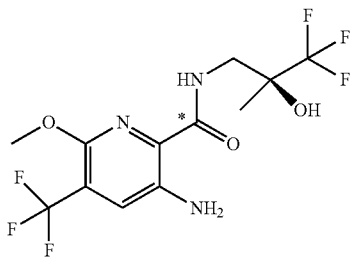

*: position of 14C-label

The chemical and radiochemical purity of the [14C] Compound 1 was >99%. The specific radioactivity of the [14C]Compound 1 was 9.15 kBq/mg (free base).

The single oral dose of 400 mg of [14C]Compound 1 contained 3.7 MBq of carbon-14 per subject. The estimated effective radiation burden after a single oral radioactivity dose of 3.7 MBq of [14C]Compound 1 was 0.22 mSv.

7.6.4. Analysis of Compound 1 and Metabolites

Pharmacokinetic samples were obtained and evaluated in all subjects. Compound 1 was determined in plasma by a validated liquid chromatography with tandem mass spectrometry (LC-MS/MS) method using electrospray ionization. A non-validated method was used to analyze metabolites of Compound 1.

The PK parameters were based on the actual recorded sampling times and non-compartmental method(s) with Phoenix WinNonLin (Version 6.4). The terminal rate constant ($\lambda z$) was determined from automated (WinNonlin algorithm) linear regression of at least the last three points with non-zero concentrations in the terminal phase of the log-transformed concentration-time profile.

7.6.5. Study Results

A total of six subjects were enrolled, of which six subjects completed in the study. The multiple-dose oral administration of 400 mg of Compound 1 as well as a single oral dose of 400 mg of radiolabeled [14C]Compound 1 were safe and well tolerated safe in healthy subjects. None of the subjects discontinued the study due to an AE. There were no clinically significant abnormalities in laboratory evaluations (hematology, clinical chemistry, urinalysis), vital signs and ECG denoting a safe drug profile. That is, no safety concerns were identified in the study.

Peak concentrations of Compound 1 and total radiolabeled components (radioactivity) after oral dosing of 400 mg [14C]Compound 1 showed substantial systemic availability of Compound 1. After oral administration of [14C]Compound 1 on Day 5 (morning dose) at a steady state of Compound 1, the radioactivity was detected in blood and plasma for up to 48 hours and 96 hours post-dose respectively, and thereafter, radioactivity levels were below the limit of quantification. Maximum concentrations (Cmax) of total radioactivity and Compound 1 in plasma and blood were reached at median (min–max) Tmax of 4.0 hours (range: 1.0 hour-4.0 hours). PK parameters of radioactivity and Compound 1 are presented in Table 25.

TABLE 25

| Pharmacokinetic parameters of radioactivity and Compound 1 in blood and plasma | | | |
|---|---|---|---|
| PK Parameter (unit) | Blood radioactivity | Plasma radioactivity | Plasma Compound 1[f] |
| Tmax (h) (median; range) | 4; 1-4 | 4; 1-4 | 4; 1-4 |
| Cmax (ng/mL)[a] | 2670 (509) | 4280 (838) | 1680 (568) |
| Tlast (h) (range) | 24-48 | 48-96 | 12 |
| AUC (last) (ng*h/mL)[b, c] | 24700 (5290) | 45600 (7830) | 8170 (3270) |

TABLE 25-continued

Pharmacokinetic parameters of radioactivity and Compound 1 in blood and plasma

| PK Parameter (unit) | Blood radioactivity | Plasma radioactivity | Plasma Compound 1[f] |
|---|---|---|---|
| T1/2 (h) | 15.4 (5.79) | 20.6 (9.55) | — |
| Typical time interval (h) | 8-48 | 24-96 | — |
| AUC (inf)[d] (ng*h/mL)[b, c] | 27900 (4610) | 48300 (8120) | — |
| (% of 14C-AUCinf plasma) | 57.9 (2.91) | — | 16.6 (5.06) |
| AUC % Extrap (% of AUCinf) | 12.2 (6.21) | 5.74 (2.53) | — |
| Vz/F (L)[g] | — | — | 335 (161) |
| CL/F (L/h) | — | — | 56.8 (25.6) |

Means[e] (SD) of N = 6 subjects, based on non-compartmental analysis
[a]: for radioactivity: [ng-eq/mL].
[b]: for radioactivity: [ng-eq·h/mL].
[c]: AUClast were calculated using the linear trapezoidal rule.
[d]: AUCinf = AUClast + AUCt-inf; AUCt-inf = Clast*T1/2/ln2.
[e]: mean values are arithmetic means of individual values.
[f]: Day 5, 0-12 hours
[g]: Mean of N = 5 (One subject had Rsq adjusted <0.75, hence Vz/F impacted by Rsq adjusted was excluded from summary of PK parameters of Compound 1)
—: not calculable, not meaningful.

After oral dosing of 400 mg [14C]Compound 1 at steady state Compound 1, the extent of oral absorption was estimated to be 93.4% (N=6, range: 89.7%-97.40%). Parent Compound 1 represented a main proportion of radioactivity in plasma (18.5% of the plasma 14C-AUC0-48 h, metabolite pattern analysis).

Compound 1 was extensively metabolized. The metabolic reactions included mainly N-glucuronidation, O-glucuronidation and/or O-demethylation. Additionally N-dealkylation, N-oxidation, oxygenation, formation of a carboxylic acid, sulfation and acetylation contributed to the biotransformation of Compound 1. The M8 and M9 metabolites (formed by N-glucuronidation and O-glucuronidation of Compound 1, respectively) were the most prominent metabolites in plasma. Metabolite M8 amounted to 5.3 of the plasma 14C-AUC0-48 h and metabolite M9 to 14.5 of the plasma 14C-AUC0-48 h. Another major metabolite M5 (formed by O-demethylation and glucuronidation) accounted for 10.7% of the plasma 14C-AUC0-48 h. Compound 1 and its metabolites in plasma based on metabolite pattern analysis are presented in Table 26. A scheme of the major biotransformation pathways of Compound 1 in humans is shown in FIG. 11. The minor biotransformation pathways of Compound in humans is shown in FIG. 12.

TABLE 26

AUC0-48 h, AUCinf and T½ of Compound 1 and its metabolites in plasma

| Peak* | Compound/Metabolite | AUC0-48 h (nmol*h/L) | %[b] | AUCinf[c] (nmol*h/L) | %[b] | T½ (h) |
|---|---|---|---|---|---|---|
| M5 | O-demethylation, glucuronidation | 12800 | 10.7 | 13800 | 10.7 | 12.1 |
| M8 | N-glucuronidation | 42200 | 35.3 | 44100 | 33.9 | 11.2 |
| M9 | O-glucuronidation | 17300 | 14.5 | 18100 | 13.9 | 11.6 |
| M10 | C-hydroxylation | 2310 | 1.93 | 2840[d] | 2.19 | — |
| M14 | O-demethylation | 1790 | 1.50 | 2000 | 1.54 | 16.8 |
| M17 | N-dealkylation | 3630 | 3.04 | 3840 | 2.96 | 10.7 |
| Compound 1 | Parent drug | 22100 | 18.5 | 22700 | 17.5 | 11.2 |
| | Sum of minor identified metabolites (ea. ≤ 1%) | 7930 | 6.63 | — | — | — |
| | Sum of unknown trace metabolites (ea. ≤ 0.3%) | 515 | 0.430 | — | — | — |
| | Lost during sample processing and HPLC | 8870 | 7.42 | — | — | — |
| Total 14C (total of radiolabeled components) | | 120000 | 100 | 130000 | 100 | 14.2 | a: plasma time pools of N = 6 subjects, calculated using the linear trapezoidal method
[b]Percent of total radiolabeled components AUC0-48 h and AUCinf in original sample, respectively.
[c]AUCinf = AUClast + AUCt-inf; AUCt-inf = Clast*T½/ln2
[d]Calculated using T½ of the total 14C based on metabolite pattern analysis
—: not meaningful, not calculated
*listed according to appearance in chromatogram, concentrations were provided with three significant digits The apparent volume of distribution (Vz/F) of Compound 1 was moderate (mean: 335 L and CV %: 48.1%). Total Compound 1-related radioactivity was mainly confined within the blood to the plasma compartment (Fp: 93.3±3.35%). From the ratio of compound-related radioactivity between blood and plasma; no special affinity of Compound 1 and/or its metabolites to erythrocytes could be concluded. The PK parameters of radioactivity and Compound 1 in plasma and blood displayed low to moderate variability in terms of Cmax and AUC.

The mean steady state plasma clearance (CLss/F) of Compound 1 was moderate (mean: 56.8 L/h and CV %: 45.1%). The mean terminal half-lives of total radiolabeled components (radioactivity) in blood and plasma were 15.4 and 20.6 hours, respectively. Compound 1 was eliminated from the systemic circulation mainly due to metabolism, and subsequent renal excretion. Renal excretion of radioactivity was mainly in the form of metabolites (92.3±4.2% of the dose). Only minor amounts of Compound 1 were detected in urine (3.35% of the dose within 0-96 hours). The bulk of the radioactive dose was recovered within 96 hours in feces and urine (>95% of dose). Excretion of radioactivity was complete after 9 days (mean: 97.6% and range 93.4%-99.1%). The samples collected after 96 hours post-dose of [14C] Compound 1 contained less than 3% of the dose. Excretion of radioactivity in urine and feces is presented in Table 27.

TABLE 27

Mean excretion of radioactivity in urine and feces

| Time period (h) | 14C-Excretion (% of dose) | | |
|---|---|---|---|
| | Urine | Feces | Total |
| 0-216 | 92.3 (4.2) | 5.2 (2.1) | 97.6 (2.1) |

What is claimed is:

1. A pharmaceutical composition comprising,
   a. (S)-3-amino-6-methoxy-N-(3,3,3-trifluoro-2-hydroxy-2-methylpropyl)-5-(trifluoromethyl)picolinamide having the following structure

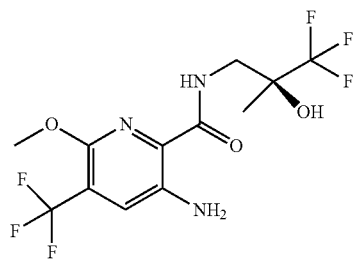 [SMILES: COc1nc(C(=O)NC[C@](C)(O)C(F)(F)F)c(N)cc1C(F)(F)F]

or a pharmaceutically acceptable salt, polymorph, or co-crystal thereof,
   b. sodium starch glycolate, and
   c. sodium stearyl fumarate.

2. A pharmaceutical composition comprising,
   a. (S)-3-amino-6-methoxy-N-(3,3,3-trifluoro-2-hydroxy-2-methylpropyl)-5-(trifluoromethyl)picolinamide having the following structure

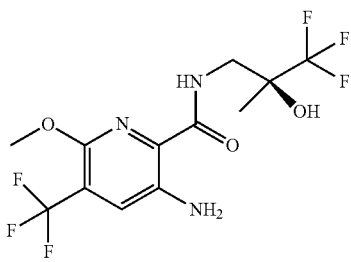 [SMILES: COc1nc(C(=O)NC[C@](C)(O)C(F)(F)F)c(N)cc1C(F)(F)F]

or a pharmaceutically acceptable salt, polymorph, or co-crystal thereof,
   b. crospovidone, and
   c. sodium stearyl fumarate.

3. A method for the treatment of bronchiectasis, chronic obstructive pulmonary disorder, cystic fibrosis, chronic bronchitis or asthma, comprising administering the pharmaceutical composition of claim 1 to a subject in need thereof.

4. A method for promoting mucus clearance in a subject with bronchiectasis, chronic obstructive pulmonary disorder, cystic fibrosis, chronic bronchitis or asthma comprising administering the pharmaceutical composition of any one of claim 1 to a subject in need thereof.

5. A process for the manufacture of the pharmaceutical composition according to claim 1 comprising the steps of: (a) blending (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof together with sodium starch glycolate and optionally at least one pharmaceutically acceptable carrier to form a material, (b) wet milling the material to form a plurality of granules, (c) blending the granules with sodium stearyl fumarate and sodium starch glycolate and optionally at least one pharmaceutically acceptable carrier to form a final blend, and (d) compressing the final blend into a tablet.

6. A process for the manufacture of the pharmaceutical composition according to claim 2 comprising the steps of: (a) blending (S)-3-amino-6-methoxy-N-(3,3,3-trifluoro-2-hydroxy-2-methylpropyl)-5-(trifluoromethyl)picolinamide or a pharmaceutically acceptable salt, polymorph or co-crystal thereof together with crospovidone and optionally at least one pharmaceutically acceptable carrier to form a material, (b) wet milling the material to form a plurality of granules, (c) blending the granules with sodium stearyl fumarate and crospovidone, and optionally at least one pharmaceutically acceptable carrier to form a final blend, and (d) compressing the final blend into a tablet.

7. A pharmaceutical composition produced by the process of claim 5.

8. A pharmaceutical composition produced by the process of claim 6.

9. A method for the treatment of bronchiectasis, chronic obstructive pulmonary disorder, cystic fibrosis, chronic bronchitis or asthma, comprising administering the pharmaceutical composition of claim 2 to a subject in need thereof.

10. A method for promoting mucus clearance in a subject with bronchiectasis, chronic obstructive pulmonary disorder, cystic fibrosis, chronic bronchitis or asthma comprising administering the pharmaceutical composition of claim 2 to a subject in need thereof.

* * * * *